US012600787B2

(12) United States Patent
Sherman et al.

(10) Patent No.: US 12,600,787 B2
(45) Date of Patent: Apr. 14, 2026

(54) METHODS FOR THE TREATMENT OF THYROID EYE DISEASE

(71) Applicant: Horizon Therapeutics Ireland DAC, Dublin (IE)

(72) Inventors: Jeffrey W. Sherman, Lincolnshire, IL (US); Dennis A. Bennett, Rio Grande, PR (US); Srini Ramanathan, Lake Forest, IL (US); Yan Xin, San Carlos, CA (US); Elizabeth Thompson, Lake Forest, IL (US); Elizabeth O'Neill, San Francisco, CA (US)

(73) Assignee: Horizon Therapeutics Ireland DAC, Dublin (IE)

( * ) Notice: Subject to any disclaimer, the term of this patent is extended or adjusted under 35 U.S.C. 154(b) by 0 days.

(21) Appl. No.: 17/654,318

(22) Filed: Mar. 10, 2022

(65) Prior Publication Data

US 2022/0356257 A1 Nov. 10, 2022

Related U.S. Application Data

(63) Continuation of application No. 17/191,651, filed on Mar. 3, 2021, now abandoned, which is a continuation-in-part of application No. PCT/US2020/048350, filed on Aug. 28, 2020.

(60) Provisional application No. 62/892,849, filed on Aug. 28, 2019.

(51) Int. Cl.
*C07K 16/28* (2006.01)
*A61K 39/00* (2006.01)
*A61P 27/02* (2006.01)

(52) U.S. Cl.
CPC .......... *C07K 16/2863* (2013.01); *A61P 27/02* (2018.01); *A61K 2039/505* (2013.01); *A61K 2039/545* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 2,373,192 | A | 4/1945 | Lauer | |
| 4,567,253 | A | 1/1986 | Durst et al. | |
| 7,037,498 | B2 | 5/2006 | Cohen et al. | |
| 7,081,454 | B2 | 7/2006 | Wittman et al. | |
| 7,317,091 | B2 | 1/2008 | Lazar et al. | |
| 7,326,699 | B2 | 2/2008 | Capraro et al. | |
| 7,534,792 | B2 | 5/2009 | Wittman et al. | |
| 7,572,897 | B2 | 8/2009 | Graus et al. | |
| 7,579,157 | B2 | 8/2009 | Graus et al. | |
| 7,605,272 | B2 | 10/2009 | Kanda et al. | |
| 7,612,178 | B2 | 11/2009 | Hariharan et al. | |
| 7,638,605 | B2 | 12/2009 | Ludwig | |
| 7,772,231 | B2 | 8/2010 | Sheppard et al. | |
| 7,939,637 | B2 | 5/2011 | Raeber et al. | |
| 7,981,903 | B2 | 7/2011 | Chamberlain et al. | |
| 8,063,225 | B2 | 11/2011 | Gregor et al. | |
| 8,084,582 | B2 | 12/2011 | Dahiyat et al. | |
| 8,093,239 | B2 | 1/2012 | Kuntz et al. | |
| 8,101,613 | B2 | 1/2012 | Arnold et al. | |
| 8,101,720 | B2 | 1/2012 | Lazar et al. | |
| 8,153,121 | B2 | 4/2012 | Smith et al. | |
| 8,188,231 | B2 | 5/2012 | Lazar et al. | |
| 8,367,805 | B2 | 2/2013 | Chamberlain et al. | |
| 8,461,170 | B2 | 6/2013 | Aquila et al. | |
| 8,476,409 | B2 | 7/2013 | Baum et al. | |
| 8,546,443 | B2 | 10/2013 | Treu et al. | |
| 8,546,543 | B2 | 10/2013 | Lazar | |
| 9,150,578 | B2 | 10/2015 | Treu | |
| 10,414,769 | B2 | 9/2019 | Treu et al. | |
| 10,457,740 | B1 * | 10/2019 | Kahvejian | A61K 31/713 |
| 11,208,489 | B2 * | 12/2021 | Madden | A61P 27/02 |
| 11,208,490 | B2 * | 12/2021 | Madden | C07K 16/241 |
| 12,209,130 | B2 | 1/2025 | Madden | |
| 12,286,481 | B2 | 4/2025 | Madden | |
| 2007/0218514 | A1 | 9/2007 | Smith | |
| 2009/0092614 | A1 | 4/2009 | Demarest et al. | |
| 2009/0232828 | A1 | 9/2009 | Zhang | |
| 2016/0287611 | A1 | 10/2016 | Dobak | |
| 2019/0225696 | A1 | 7/2019 | Madden et al. | |
| 2019/0270820 | A1 | 9/2019 | Madden et al. | |
| 2021/0253719 | A1 | 8/2021 | Sherman et al. | |
| 2021/0284741 | A1 * | 9/2021 | Madden | A61K 45/06 |
| 2022/0324985 | A1 * | 10/2022 | Madden | A61K 45/06 |

(Continued)

FOREIGN PATENT DOCUMENTS

| | | | |
|---|---|---|---|
| WO | WO-9524190 | A2 | 9/1995 |
| WO | WO-03106621 | A2 | 12/2003 |
| WO | WO-2005058967 | A2 | 6/2005 |

(Continued)

OTHER PUBLICATIONS

Xu et al., Eye Science, 27(2):64-68, 2012.*

(Continued)

*Primary Examiner* — Marianne P Allen
(74) *Attorney, Agent, or Firm* — Angela L. Purcell

(57) ABSTRACT

Provided herein are methods of treating or reducing the severity of thyroid eye disease (TED), also known as thyroid-associated ophthalmopathy (TAO), or Graves' ophthalmopathy or orbitopathy (GO), as well as antibodies, or antigen binding fragments thereof, and pharmaceutical compositions comprising them, useful in the methods.

19 Claims, No Drawings

Specification includes a Sequence Listing.

(56) References Cited

U.S. PATENT DOCUMENTS

2022/0340667 A1* 10/2022 Madden ............... A61K 9/0019
2024/0301072 A1* 9/2024 Madden .................. A61P 27/02

FOREIGN PATENT DOCUMENTS

| | | | |
|---|---|---|---|
| WO | 2006013472 | A2 | 2/2006 |
| WO | WO-2006069202 | A2 | 6/2006 |
| WO | WO-2006080450 | A1 | 8/2006 |
| WO | WO-2007079164 | A2 | 7/2007 |
| WO | WO-2011158931 | A1 | 12/2011 |
| WO | WO-2012007926 | A1 | 1/2012 |
| WO | WO-2012145471 | A1 | 10/2012 |
| WO | WO-2014135611 | A1 | 9/2014 |
| WO | WO-2016064716 | A1 | 4/2016 |
| WO | WO-2019173352 | A1 | 9/2019 |
| WO | WO-2021041773 | A1 | 3/2021 |

OTHER PUBLICATIONS

NCT06248619, May 22, 2025 version, accessed Jun. 16, 2025.*

Bartalena et al., Consensus statement of the European Group on Graves' orbitopathy (EUGOGO) on management of GO. Eur J Endocrinol 158(No. 3):273-285 (2008).

Degorce et al. Discovery of a Potent Selective Orally Bioavailable and Efficacious Novel 2-(Pyrazol-4-ylamino)-pyrimidine Inhibitor of the Insulin-like Growth Factor-1 Receptor (IGF-1R) J Med Chem 59(10):4859-4866 (2016).

Dolman et al., VISA Classification for Graves orbitopathy. Ophthalmic Plast Reconstr Surg 22(No. 5):319-324 (2006).

Dolman., Evaluating Graves' orbitopathy. Best Pract Res Clin Endocrinol Metab 26(No. 3):229-248 (2012).

Douglas et al., Teprotumumab for the Treatment of Active Thyroid Eye Disease. N Engl J Med 2020; 382:341-52 (2020).

Douglas., Teprotumumab, an Insulin-Like Growth Factor-1 Receptor Antagonist Antibody, in the Treatment of Active Thyroid Eye Disease: A Focus on Proptosis. Eye (Lond) 33(2):183-90 (2019).

Gupta., Intention-to-treat concept: A review. Perspect Clin Res. 2(3):109-112 (2011).

Kabat et al. Sequences of Proteins of Immunological Interest. NIH Pub. No. 91-3242. Public Health Service, National Institutes of Health. 1:647-669 (1991).

Kahaly et al. Highlighted Oral 2, abstract presented at the American Thyroid Association (ATA) 88th Annual Meeting, Washington, DC, Oct. 3-8, 2018.

Mourits et al., Clinical activity score as a guide in the management of patients with Graves' ophthalmopathy. Clin Endocrinol (Oxf) 47(No. 1):9-14 (1997).

Mourits et al., Clinical criteria for the assessment of disease activity in Graves' ophthalmopathy: a novel approach. Br J Ophthalmol 73(No. 8):639-644 (1989).

PCT/US2020/048350 International Search Report and Written Opinion dated Feb. 3, 2021.

Piantanida et al., Teprotumumab: A New Avenue for the Management of Moderate-to-Severe and Active Graves' Orbitopathy? J Endocrinol Invest., 40(8):885-7 (2017).

Sanderson et al. BI 885578 a Novel IGF1R/INSR Tyrosine Kinase Inhibitor with Pharmacokinetic Properties That Dissociate Antitumor Efficacy and Perturbation of Glucose Homeostasis. Mol Cancer Ther 14(12):2762-72 (2015).

Smith et al., Teprotumumab for Thyroid-Associated Ophthalmopathy. N Engl J Med., 376(18):1748-61 (2017).

Titze et al. An allometric pharmacokinetic/pharmacodynamics model for BI 893923 a novel IGF-1 receptor inhibitor. Cancer Chemother Pharmacol 79(3):545-558 (2017).

U.S. Appl. No. 17/191,651 Office Action dated May 24, 2021.

U.S. Appl. No. 17/191,651 Office Action dated Sep. 10, 2021.

Werner., Classification of the eye changes of Graves' disease. Am J Ophthalmol 68(No. 4):646-648 (1969).

Werner., Modification of the classification of the eye changes of Graves' disease. Am J Ophthalmol 83(No. 5):725-727 (1977).

Douglas et al., "Efficacy and Safety of Teprotumumab in Patients With Thyroid Eye Disease of Long Duration and Low Disease Activity," The Journal of Clinical Endocrinology & Metabolism, vol. 109(1), pp. 25-35 (2024).

Patel et al., "A New Era in the Treatment of Thyroid Eye Disease," American Journal of Ophthalmology, vol. 208: pp. 281-288 (2019).

Ma et al., "The adverse events profile of anti-IGF-1R monoclonal antibodies in cancer therapy," Br. J. Clin. Pharmacol., vol. 77(6), pp. 917-928 (2013).

Smith et al., "Role of IGF-1 pathway in the pathogenesis of Graves' orbitopathy," Best Pract. Res. Clin. Endocrinol. Metab., vol. 26(3), pp. 291-302 (2012).

Xue et al., "Insulin-like growth factor-1 receptor (IGF-1R) kinase inhibitors in cancer therapy: advances and perspectives," Curr. Pharm. Des., vol. 18(20), pp. 2901-2913 (2012).

Bagatell et al., "Pharmacokinetically Guided Phase 1 Trial of the IGF-1 Receptor Antagonist RG1507 in Children with Recurrent or Refractory Solid Tumors," Clin. Cancer Res., vol. 17(3), pp. 611-619 (2011).

Bahn, "Current Insights into the Pathogenesis of Graves' Ophthalmopathy," Horm Metab Res., vol. 47(10), pp. 773-778 (2015).

Bahn, "Graves' ophthalmopathy," N. Engl. J. Med., vol. 8, pp. 726-738 (2010).

Bartalena et al., "Efficacy and safety of three different cumulative doses of intravenous methylprednisolone for moderate to severe and active Graves' orbitopathy," J. Clin. Endocrinol. Metab., vol. 97(12), pp. 4454-4463 (2012).

Chen et al., "Effects and Its Mechanism of IGF-1R on the Synthesis of Hyaluronic Acid in Orbital Fibroblasts of Thyroid Associated Ophthalmopathy," Sichuan Da Xue Xue Bao Yi Xue Ban, vol. 48(5), pp. 727-731 (2017).

Chen et al., "Teprotumumab, an IGF-1R blocking monoclonal antibody inhibits TSH and IGF-1 action in fibrocytes," J Clin Endocrinol Metab., vol. 99(9), pp. E1635-E1640 (2014).

Clinical Trials No. NCT01868997. Teprotumumab (RV 001) Treatment in Patients With Active Thyroid Eye Disease, Version 21. Reported date submitted: Aug. 10, 2017. Date publicly available: Unknown. Date accessed: May 24, 2024.

Douglas et al., "Aberrant expression of the insulin-like growth factor-1 receptor by T cells from patients with Graves' disease may carry functional consequences for disease pathogenesis," J. Immunol., vol. 178(5), pp. 3281-3287 (2007).

Douglas et al., "B cells from patients with Graves' disease aberrantly express the IGF-1 receptor: implications for disease pathogenesis," J. Immunol., vol. 181(8), pp. 5768-5774 (2008).

Douglas et al., "Increased generation of fibrocytes in thyroid-associated ophthalmopathy," J. Clin. Endrocrinol. Metab., vol. 95(1), pp. 430-438 (2010).

Ezra et al., "Genome Level Microarray Expression Profiling Implicates IGF-1 and Wnt Signalling Dysregulation in the Pathogenesis of Thyroid Associated Ophthalmopathy," ARVO Annual Meeting Scientific Abstracts, Invest. Ophthalmol. Vis. Sci., vol. 52, 5100, pp. 1-2 (2011).

Gianoukakis et al., "Immunoglobulin G from patients with Graves' disease induces interleukin-16 and RANTES expression in cultured human thyrocytes: a putative mechanism for T-cell infiltration of the thyroid in autoimmune disease," Endocrinology, vol. 147(4), pp. 1941-1949 (2006).

Görtz et al., "Pathogenic Phenotype of Adipogenesis and Hyaluronan in Orbital Fibroblasts from Female Graves' Orbitopathy Mouse Model," Endocrinology, vol. 157(10), pp. 3771-3778 (2016).

Hansson, "Aspects of growth factors in exophthalmos," Acta Endocrinologica (Cophen), vol. 121 (Suppl 2), pp. 107-111 (1989).

Hoa et al., "Nuclear Targeting of IGF-1 Receptor in Orbital Fibroblasts from Graves' Disease: Apparent Role of ADAM17," PLoS One, vol. 7(4), e34173, pp. 1-9 (2012).

Hwang et al., "Orbital fibroblasts from patients with thyroid-associated ophthalmopathy overexpress CD40: CD154 hyperinduces IL-6, IL-8, and MCP-1," Invest. Ophthalmol. Vis. Sci., vol. 50(5), pp. 2262-2268 (2008).

(56) References Cited

OTHER PUBLICATIONS

Imai et al., "Effect of growth factors on hyaluronan and proteoglycan synthesis by retroocular tissue fibroblasts of Graves' ophthalmopathy in culture," Acta Endocrinol (Copenh), vol. 126(6), pp. 541-552 (1992).
Khong et al., "Pathogenesis of thyroid eye disease: review and update on molecular mechanisms," Br. J. Ophthalmol., vol. 100(1), pp. 142-150 (2016).
Khoo et al., "Pathogenesis of Graves' Ophthalmopathy: The Role of Autoantibodies," Thyroid, vol. 17(10), pp. 1013-1018 (2007).
Krieger et al., "Thyroid Stimulating Hormone (TSH)/Insulin-like Growth Factor 1 (IGF1) Receptor Cross-talk in Human Cells," Curr. Opin. Endocr. Metab. Res., vol. 2, pp. 29-33 (2018).
Krieger et al., "TSH/IGF-1 Receptor Cross-Talk Rapidly Activates Extracellular Signal-Regulated Kinases in Multiple Cell Types," Endocrinology, vol. 158(10), pp. 3676-3683 (2017).
Krieger et al., "TSHR/IGF-1R Cross-Talk, Not IGF-R Stimulating Antibodies, Mediates Graves' Ophthalmopathy Pathogenesis," Thyroid, vol. 27(5), pp. 746-747 (2017).
Kumar et al., "A stimulatory thyrotropin receptor antibody enhances hyaluronic acid synthesis in graves' orbital fibroblasts: inhibition by an IGF-I receptor blocking antibody," J Clin Endocrinol Metab., vol. 97(5), pp. 1681-1687 (2012).
Kumar et al., "Forkhead Transcription Factor FOXO1 Is Regulated by Both a Stimulatory Thyrotropin Receptor Antibody and Insulin-Like Growth Factor-1 in Orbital Fibroblasts from Patients with Graves' Ophthalmopathy," Thyroid, vol. 25(10), pp. 1145-1150 (2015).
Kurzrock et al., "A Phase I Study of Weekly R1507, a Human Monoclonal Antibody Insulin-like Growth Factor-I Receptor Antagonist, in Patients with Advanced Solid Tumors," Clin. Cancer Res., vol. 16(8), pp. 2458-2465 (2010).
Marcus-Samuels, "Evidence That Graves' Ophthalmopathy Immunoglobulins Do Not Directly Activate IGF-1 Receptors," Thyroid, vol. 28(5), pp. 650-655 (2018).
Naik et al., "Immunopathogenesis of thyroid eye disease: emerging paradigms," Surv. Ophthalmol., vol. 55(3), pp. 215-226 (2010).
Palowski et al., "Decreased Frequencies of Peripheral Blood CD4+ CD25+CD127-Foxp3+ in Patients with Graves' Disease and Graves' Orbitopathy: Enhancing Effect of Insulin Growth Factor-1 on Treg Cells, " Horm. Metab. Res., vol. 49(3), pp. 185-191 (2017).
Pappo et al., "R1507, a Monoclonal Antibody to the Insulin-Like Growth Factor 1 Receptor, in Patients With Recurrent or Refractory Ewing Sarcoma Family of Tumors: Results of a Phase II Sarcoma Alliance for Research Through Collaboration Study," J. Clin. Oncol., vol. 29(34), pp. 4541-4547 (2011).
Place et al., "Inhibiting thyrotropin/insulin-like growth factor 1 receptor crosstalk to treat Graves' ophthalmopathy: studies in orbital fibroblasts in vitro," Br. J. Pharmacol., vol. 174(4), pp. 328-340 (2017).
Pritchard et al., "Igs from patients with Graves' disease induce the expression of T cell chemoattractants in their fibroblasts," J. Immunol., vol. 168(2), pp. 942-950 (2002).
Pritchard et al., "Immunoglobulin activation of T cell chemoattractant expression in fibroblasts from patients with Graves' disease is mediated through the insulin-like growth factor I receptor pathway," J. Immunol., vol. 170(12), pp. 6348-6354 (2003).
Ramalingam et al., "Randomized Phase II Study of Erlotinib in Combination with Placebo or R1507, a Monoclonal Antibody to Insulin-Like Growth Factor-1 Receptor, for Advanced-Stage Non-Small-Cell Lung Cancer," J. Clin. Oncol., 29(34), pp. 4574-4580 (2011).
Salvi et al., "Efficacy of B-cell targeted therapy with rituximab in patients with active moderate to severe Graves' obitopathy: a randomized controlled study," J. Clin. Endocrinol. Metab., vol. 100(2), pp. 422-431 (2015).
Salvi, "Immunotherapy for Graves' ophthalmopathy," Curr. Opin. Endocrinol. Diabetes Obes., vol. 21(5), pp. 409-414 (2014).
Smith et al., "Building the Case for Insulin-Like Growth Factor Receptor-I Involvement in Thyroid-Associated Ophthalmopathy," Frontiers in Endocrinology, vol. 7(167), pp. 1-8 (2017).
Smith et al., "Immunoglobulins from Patients with Graves' Disease Induce Hyaluronan Synthesis in Their Orbital Fibroblasts through the Self-Antigen, Insulin-Like Growth Factor-I Receptor," J Clin Endocrinol Metab., vol. 89(10), pp. 5076-5080 (2004).
Smith et al., "Insulin-Like Growth Factor-I Regulation of Immune Function: A Potential Therapeutic Target in Autoimmune Diseases?" Pharmacological Rev., vol. 62(2), pp. 199-236 (2010).
Smith et al., "New Advances in Understanding Thyroid-Associated Ophthalmopathy and the Potential Role for Insulin-Like Growth Factor-I Receptor [version 1; referees: 2 approved]," F1000 Research 2018, 7(F1000 Faculty Rev): 134, pp. 1-9 (Last Updated Feb. 1, 2018).
Smith et al., "Pathogenesis of Graves' orbitopathy: A 2010 update," J. Endocrinol. Invest., vol. 33(6), pp. 414-421 (2010).
Smith et al., "Unique attributes of orbital fibroblasts and global alterations in IGF-1 receptor signaling could explain thyroid-associated ophthalmopathy," Thyroid, vol. 18(9), pp. 983-988 (2008).
Smith, "Recognizing the Putative Role for TSH Receptor Expressing Fibrocytes in Thyroid-Associated Ophthalmopathy may solve several mysteries," Nat. Rev. Endocrinol., vol. 11(3), pp. 171-181 (2015).
Song et al. "Locally produced insulin-like growth factor-1 by orbital fibroblasts as implicative pathogenic factor rather than systemically circulated IGF-1 for patients with thyroid-associated ophthalmopathy," Graefes Arch Clin Exp Ophthalmol., vol. 250(3), pp. 433-440 (2012).
Stan et al., "Randomized controlled trial of rituximab in patients with Graves' orbitopathy," J. Clin. Endocrinol. Metab., vol. 100(2), pp. 432-431 (2015).
Terwee et al., "Development of a disease specific quality of life questionnaire for patients with Graves' ophthalmopathy: the GO-QOL," Br. J. Ophthalmopathy, vol. 82, pp. 773-779 (1998).
Tsui et al., "Evidence for an association between thyroid-stimulating hormone and insulin-like growth factor 1 receptors: a tale of two antigens implicated in Graves' disease," J. Immunol., vol. 181(6), pp. 4397-4405 (2008).
Varewijck et al., "Circulating IgGs may modulate IGF-I receptor stimulating activity in a subset of patients with Graves' ophthalmopathy," J. Clin. Endocrinol. Metab., vol. 98(2), pp. 769-776 (2013).
Weightman et al., "Autoantibodies to IGF-1 binding sites in thyroid associated ophthalmopathy," Autoimmunity, vol. 16(4), pp. 251-257 (1993).
Wiersinga et al., "Clinical assessment of patients with Graves' orbitopathy: the European Group on Graves' Orbitopathy recommendations to generalists, specialists and clinical researchers," European Journal of Endocrinology, vol. 155, pp. 387-389 (2006).
Wiersinga, "Management of Graves' ophthalmopathy," Endocrinology & Metabolism, vol. 3(5), pp. 396-404 (2007).
Xu et al., "Comparative Efficacy of Medical Treatments for Thyroid Eye Disease: A Network Meta-Analysis," J. Ophthalmol., vol. 2018, 7184163, pp. 1-10 (2018).
Zhang et al., "Possible Targets for Nonimmunosuppressive Therapy of Graves' Orbitopathy," J. Clin. Endocrinol. Metab., vol. 99(7), pp. E1183-E1190 (2014).
Zhao et al., "Insulin-like growth factor 1 promotes to the proliferation and adipogenesis of orbital adipose-derived stromal cells in thyroid-associated ophthalmopathy," Exp. Eye Res., vol. 107, pp. 65-73 (2013).
Bartalena et al., "The 2016 European Thyroid Association/European Group on Graves' Orbitopathy Guidelines for the Management of Graves' Orbitopathy," Eur. Thyroid J., vol. 5(1), pp. 9-26 (2016).
Calzone et al., "Epitope-Specific Mechanisms of IGF1R Inhibition by Ganitumab," PLoS One, vol. 8(2), e55135, pp. 1-15 (2013).
Chen et al., "IGF-1R as an anti-cancer target—trials and tribulations," Chin. J. Cancer, vol. 32(5), pp. 242-252 (2013).
Crudden et al., "Below the Surface: IGF-1R Therapeutic Targeting and Its Endocytic Journey," Cells, vol. 8(10), 1223, pp. 1-23 (2019).
Doern et al., "Characterization of inhibitory anti-insulin-like growth factor receptor antibodies with different epitope specificity and

(56) References Cited

OTHER PUBLICATIONS ligand-blocking properties: implications for mechanism of action in vivo," J. Biol. Chem., vol. 284(15), pp. 10254-10267 (2009).
Kuenkele et al., "Abstract LB-397: Functional characterization of IGF-1R antibodies and possible implications for clinical safety and efficacy," Cancer Res., vol. 71 (8 Suppl), Abstract LB-391 (2011).
Mao et al., "Polyubiquitination of insulin-like growth factor I receptor (IGF-IR) activation loop promotes antibody-induced receptor internalization and down-regulation," J. Biol. Chem., vol. 286(48), pp. 41852-41861 (2011).
Martins et al., "IGF1R Signaling in Ewing Sarcoma Is Shaped by Clathrin-/Caveolin-Dependent Endocytosis," PLoS One, vol. 6(5), e19846, pp. 1-12 (2011).
Sanofi-Aventis Group, "Uncontrolled, multicenter, dose finding, safety and pharmacokinetic study of AVE 1642, an anti-insulin-like Growth Factor-1 Receptor (IGF-1R/CD221) monoclonal antibody, administered as single agent and in combination with anticancer therapies in patients with advanced solid tumors," Synopsis Style Clinical Study Report dated Mar. 4, 2011.
Solomon-Zemler et al., "Nuclear insulin-like growth factor-1 receptor (IGF1R) displays proliferative and regulatory activities in non-malignant cells," PLoS One, vol. 12(9), e0185164, pp. 1-14 (2017).
Third-Party Observations filed in European Patent Application No. 20858844.2 (Oct. 2, 2025).
Von Mehren et al., "A phase 1, open-label, dose-escalation study of BIIB022 (anti-IGF-1R monoclonal antibody) in subjects with relapsed or refractory solid tumors," Invest. New Drugs, vol. 32(3), pp. 518-525 (2014).
Wang et al., "Drugging IGF-1R in cancer: New insights and emerging opportunities," Genes Dis., vol. 10(1), pp. 199-211 (2022).
Werner, "The IGF1 Signaling Pathway: From Basic Concepts to Therapeutic Opportunities," Int. J. Mol. Sci., vol. 24 (19), 14882, pp. 1-13 (2023).
Clinical Trial No. NCT04583735. A Study Evaluating TEPEZZAR Treatment in Patients With Chronic (Inactive) Thyroid Eye Disease, Version 1. Reported date submitted: Oct. 6, 2020. Reported date first posted: Oct. 12, 2020-. Date accessed: Sep. 28, 2025.
Clinical Trial No. NCT04583735. A Study Evaluating TEPEZZAR Treatment in Patients With Chronic (Inactive) Thyroid Eye Disease, Version 2. Reported date submitted: Aug. 5, 2021. Reported date update posted: Aug. 6, 2021. Date accessed: Sep. 28, 2025.

* cited by examiner

METHODS FOR THE TREATMENT OF THYROID EYE DISEASE

This application is a continuation of U.S. application Ser. No. 17/191,651, filed Mar. 3, 2021, which is a continuation in part of International Application No. PCT/US2020/048350, filed Aug. 28, 2020, which claims the benefit of U.S. Provisional Application No. 62/892,849, filed Aug. 28, 2019, the disclosures of which are hereby incorporated by reference as if written herein in their entireties.

DESCRIPTION OF THE TEXT FILE SUBMITTED ELECTRONICALLY

The present application contains a Sequence Listing, which has been submitted electronically in TXT format and is hereby incorporated by reference in its entirety. The computer readable format copy of the Sequence Listing, which was created Jan. 5, 2026, is named 10791-US03-CNT_SubSequence_Listing_ST25 and is 78,728 bytes in size.

Thyroid eye disease (TED), also known as thyroid-associated ophthalmopathy (TAO), Graves' ophthalmopathy or orbitopathy (GO), thyrotoxic exophthalmos, dysthyroid ophthalmopathy, and several other terms, is orbitopathy associated with thyroid dysfunction. TAO is divided into two types. Active TED, which typically lasts 1-3 years, is characterized by an ongoing autoimmune/inflammatory response in the soft tissues of the orbit. Active TED is responsible for the expansion and remodeling of the ocular soft tissues. The autoimmune/inflammatory response of active, or acute, TED spontaneously resolves and the condition transitions into inactive TED. Inactive, or chronic, TED is the term used to describe the long-term/permanent sequelae of active TED.

BACKGROUND OF THE DISCLOSURE

The cause of TED is unknown. TED is typically associated with Graves' hyperthyroidism but can also occur as part of other autoimmune conditions that affect the thyroid gland and produce pathology in orbital and periorbital tissue, and, rarely, the pretibial skin (pretibial myxedema) or digits (thyroid acropachy). TED is an autoimmune orbitopathy in which the orbital and periocular soft tissues are primarily affected with secondary effects on the eye and vision. In TED, as a result of inflammation and expansion of orbital soft tissues, primarily eye muscles and adipose, the eyes are forced forward (bulge) out of their sockets—a phenomenon termed proptosis or exoplthalnos.

The annual incidence rate of TED has been estimated at 16 cases per 100,000 women and 2.9 cases per 100,000 men from a study based in one largely rural Minnesota community. There appears to be a female preponderance in which women are affected 2.5-6 times more frequently than men; however, severe cases occur more often in men than in women. In addition, most patients are aged 30-50 years, with severe cases appearing to be more frequent in those older than 50 years. Although most cases of TED do not result in loss of vision, this condition can cause vision-threatening exposure keratopathy, troublesome diplopia (double vision), and compressive dysthyroid optic neuropathy.

TED may precede, coincide with, or follow the systemic complications of dysthyroidism. The ocular manifestations of TED include upper eyelid retraction, lid lag, swelling, redness (erythema), conjunctivitis, and bulging eyes (exophthalmos or proptosis), chemosis, periorbital edema, and altered ocular motility with significant functional, social, and cosmetic consequences.

Many of the signs and symptoms of TED, including proptosis and ocular congestion, result from expansion of the orbital adipose tissue and periocular muscles. The adipose tissue volume increases owing in part to new fat cell development (adipogenesis) within the orbital fat. The accumulation of hydrophilic glycosaminoglycans, primarily hyaluronic acid, within the orbital adipose tissue and the perimysial connective tissue between the extraocular muscle fibers, further expands the fat compartments and enlarges the extraocular muscle bodies. Hyaluronic acid is produced by fibroblasts residing within the orbital fat and extraocular muscles, and its synthesis in vitro is stimulated by several cytokines and growth factors, including IL-1β, interferon-γ, platelet-derived growth factor, thyroid stimulating hormone (TSH) and insulin-like growth factor I (IGF-I).

TED is commonly considered to be the autoimmune orbital manifestation of Graves' Disease (GD). However, only approximately 30% f patients with Graves' hyperthyroidism manifest clinically relevant ocular pathology indicating there is mechanistic heterogeneity and differentiation between the conditions. The molecular mechanisms underlying TED remain unclear. It is accepted that the generation of autoantibodies that act as agonists on the thyroid-stimulating hormone receptor (TSHR) is responsible for Graves' hyperthyroidism. Pathogenic overstimulation of TSHR, leads to overproduction of thyroid hormones (T3 and T4) and accelerated metabolism of many tissues.

In active TED, autoantibodies trigger connective tissue and fat to expand, in part from stimulating excessive synthesis of hyaluronan. The expanded tissues are infiltrated with T and B cells, become inflamed, and are extensively remodeled. It has been suggested that TSHR might have some pathogenic role in the development of active TED. Indeed, a positive correlation has been found between anti-TSHR antibodies and the degree of TED activity. However, no definitive link has been established, and a proportion of TED patients remain euthyroid throughout the course of their disease.

Antibodies that activate the insulin-like growth factor I receptor (IGF-IR) have also been detected and implicated in active TED. Without being bound to any theory, it is believed that TSHR and IGF-IR form a physical and functional complex in orbital fibroblasts, and that blocking IGF-IR appears to attenuate both IGF-I and TSH-dependent signaling. It has been suggested that blocking IGF-IR using an antibody antagonist might reduce both TSHR- and IGF-I-dependent signaling and therefore interrupt the pathological activities of autoantibodies acting as agonists on either receptor.

IGF-IR is a widely expressed heterotetrameric protein involved in the regulation of proliferation and metabolic function of many cell types. It is a tyrosine kinase receptor comprising two subunits. IGF-IRα contains a ligand-binding domain while IGF-IRP is involved in signaling and contains tyrosine phosphorylation sites. Monoclonal antibodies directed against IGF-IR have been developed and assessed as a therapeutic strategy for several types of solid tumors and lymphomas.

Management of hyperthyroidism due to Graves' disease is imperfect because therapies targeting the specific underlying pathogenic autoimmune mechanisms of the disease are lacking. Even more complex is the treatment of moderate-to-severe active TED. Although recent years have witnessed a better understanding of its pathogenesis, TED remains a therapeutic challenge and dilemma. There are no approved drugs to treat active TED. Intravenous glucocorticoids (ivGCs) and oral glucocorticoids are used to treat patients with moderate-to-severe active TED, but results are seldom satisfactory. Partial responses are frequent and relapses (rebound) after drug withdrawal are not uncommon. Adverse events do occur and many patients eventually require rehabilitative surgery conducted when their condition has transitioned to inactive TED.

Recently, attention has been focused on the use of biologicals, which might specifically intervene on the pathogenic mechanisms of TED. In 2015 two small, monocenter, randomized clinical trials (RCTs) investigated the effects of rituximab, a CD20+ B cell-depleting agent, versus placebo or ivGCs, respectively. The results from the two trials were conflicting; they were negative (no differences with placebo) in the first trial, but positive (beneficial effects comparable to ivGCs) in the second one. The effectiveness of rituximab for moderate-to-severe active TED therefore remains to be determined. The recent guidelines published by the European Thyroid Association/European Group on Graves' Orbitopathy (EUGOGO) indicate rituximab as a possible second-line treatment for patients poorly responsive to a first course of ivGCs. As with rituximab, there is no dependable evidence concerning other potential therapeutic agents, such as adalimumab, etanercept, infliximab, or monoclonals or small molecules blocking the TSH receptor. The use of the interleukin-6 receptor monoclonal antibody, tocilizumab, based on an ongoing RCT also remains to be determined.

As stated above, medical therapies for moderate-to-severe TED that have proved to be effective and safe in adequately powered, prospective, placebo-controlled trials are lacking. Previous clinical trials, which were rarely placebo-controlled, suggest that high dose glucocorticoids, alone, or with radiotherapy, can reduce inflammation-related signs and symptoms in patients with active ophthalmopathy, but only minimally affect proptosis and can cause dose-limiting adverse reactions.

Immunoglobulins that activate IGF-IR signaling have been detected in patients with GD and TED. Furthermore, IGF-I synergistically enhances the actions of thyrotropin. IGF-IR, a membrane-spanning tyrosine kinase receptor with roles in development and metabolism, also stimulates immune function and thus might be targeted therapeutically in autoimmune diseases. IGF-IR is overexpressed by orbital fibroblasts and by T cells and B cells in persons with GD and TED. It forms a signaling complex with TSHR through which it is transactivated. In vitro studies of orbital fibroblasts and fibrocytes show that IGF-IR-inhibitory antibodies can attenuate the actions of IGF-I, thyrotropin, thyroid-stimulating immunoglobulins, and immunoglobulins isolated from patients with GD and TED. These observations prompted a trial of teprotumumab, a fully human IGF-IR-inhibitory monoclonal antibody, in patients with active, moderate-to-severe TED.

SUMMARY OF THE DISCLOSURE

Provided herein are methods of treating or reducing the severity of thyroid eye disease (TED), and achieving specific treatment endpoints in the treatment of TED, such as reducing proptosis, diplopia, TED clinical activity score and subsets and individual measures thereof, and of improving the quality of life of TED patients, comprising administering to the subject with TED an effective amount of an insulin like growth factor-I receptor (IGF 1R) inhibitor.

Certain IGF-1R inhibitors are able to decrease TSHR and IGF-IR display by orbital fibroblasts and fibrocytes and attenuate the actions of IGF-I, TSH, thyroid-stimulating immunoglobulins, and immunoglobulins isolated from patients with TED (TAO or GO).

As described above, TED (TAO or GO) remains inadequately treated. Prior to the approval of teprotumumab (TEPEZZA™), medical therapies, which primarily consisted of glucocorticoids, had limited efficacy and presented safety concerns. It is well known that broad immunosuppressive treatments for ED, e.g. glucocorticoids and rituximab, cause a limited reduction in exophthalmos. In the largest RCT using three different cumulative doses of ivGCs (2.25 g, 4.98 g. 7.47 g of methylprednisolone), the mean reduction in proptosis was 0.6 mm, even using the highest dose. Results were not different using rituximab. Further, advanced cases of TED (TAO or GO) usually called for more invasive surgical treatment such as orbital decompression. Previous therapies for the treatment of TED (TAO or GO) had, as stated above, not only limited efficacy, but also safety concerns. Teprotumumab, an IGF-IR inhibiting monoclonal antibody, has proven to be effective in the treatment of TED.

As stated by one of skill in the art, "[t]he most striking and unexpected effect of teprotumumab is the treatment-related decrease in exophthalmos [i.e., proptosis]." It is well known that immunosuppressive treatments for GO cause a limited reduction in exophthalmos, but with the methods disclosed herein] exophthalmos decreased by an average of 2.46 mm (vs. 0.15 mm in the placebo group) . . . . These results, never achieved with whatsoever medical treatment, are comparable to those obtained with orbital decompression" (Piantanida, E. and Bartalena, L. *J Endocrinol Invest,* 2017, 40, 885-887).

Although teprotumumab is effective for the treatment of TED, for various reasons, not all patients benefit from treatment with teprotumumab. There is still unmet medical need for alternate therapies for TED, e.g. for different drugs that may be administered via alternate modes and on alternate schedules.

DETAILED DESCRIPTION

Provided herein are methods and compositions for the treatment of thyroid eye disease and related conditions, as illustrated by the following embodiments.

EMBODIMENTS

Embodiment 1. A method of treating thyroid eye disease (TED), comprising administering to the subject an effective amount of an insulin like growth factor-I receptor (IGF-1R) inhibitor.

Embodiment 2. A method of reducing proptosis by at least 2 mm in a subject with thyroid eye disease (TED), comprising administering to the subject an effective amount of an IGF-IR inhibitor.

Embodiment 3. The method of Embodiment 2, wherein proptosis is reduced by at least 3 mm.

Embodiment 4. The method of Embodiment 3, wherein proptosis is reduced by at least 4 mm.

Embodiment 5. The method of Embodiment 2, wherein the method additionally comprises reducing the clinical activity score (CAS) in the subject with TED.

Embodiment 6. The method of Embodiment 5, wherein CAS is reduced by at least 2 points.

Embodiment 7. The method of Embodiment 6, wherein CAS is reduced by at least 3 points.

Embodiment 8. The method of Embodiment 7, wherein proptosis is reduced by at least 3 mm and CAS is reduced by at least 3 points.

Embodiment 9. A method of treating or reducing the severity of diplopia in a subject with thyroid eye disease (TED), comprising administering to the subject an effective amount of an insulin like growth factor-I receptor (IGF-1R) inhibitor.

Embodiment 10. The method of Embodiment 9, wherein the diplopia is constant diplopia.

Embodiment 11. The method of Embodiment 9, wherein the diplopia is intermittent diplopia.

Embodiment 12. The method of Embodiment 9, wherein the diplopia is inconstant diplopia Embodiment 13. The method of any of Embodiments 9-12, wherein the improvement in or reduction in severity of diplopia is sustained at least 20 weeks after discontinuation of inhibitor administration.

Embodiment 14. The method of any of Embodiments 9-12, wherein the improvement in or reduction in severity of diplopia is sustained at least 50 weeks after discontinuation of inhibitor administration.

Embodiment 15. A method of treating or reducing the severity of thyroid eye disease (TED), or a symptom thereof, in a subject with TED, comprising administering to the subject an effective amount of an insulin like growth factor-I receptor (IGF-1R) inhibitor.

Embodiment 16. A method of reducing proptosis in an eye in a subject with thyroid eye disease (TED) in a subject with TED, comprising administering to the subject an effective amount of an insulin like growth factor-I receptor (IGF-1R) inhibitor.

Embodiment 17. A method of reducing Clinical Activity Score (CAS) of thyroid eye disease (TED) in a subject with TED, comprising administering to the subject an effective amount of an insulin like growth factor-I receptor (IGF-1R) inhibitor.

Embodiment 18. A method of a) reducing proptosis by at least 2 mm and b) reducing the clinical activity score (CAS) in a subject with thyroid eye disease (TED), comprising administering to the subject an effective amount of an insulin like growth factor-I receptor (IGF-1R) inhibitor.

Embodiment 19. The method of any of Embodiments 15, 16, and 18, wherein proptosis is reduced by at least 2 mm.

Embodiment 20. The method of Embodiment 19, wherein proptosis is reduced by at least 3 mm.

Embodiment 21. The method of Embodiment 20, wherein proptosis is reduced by at least 4 mm.

Embodiment 22. The method of any of Embodiments 15-21, wherein the clinical activity score (CAS) of the subject is reduced by at least 2 points.

Embodiment 23. The method of Embodiment 22, wherein the clinical activity score (CAS) of the subject is reduced to one (1).

Embodiment 24. The method of Embodiment 23, wherein the clinical activity score (CAS) of the subject is reduced to zero (0).

Embodiment 25. A method of improving the quality of life in a subject with thyroid eye disease (TED) comprising administering to the subject an effective amount of an insulin like growth factor-I receptor (IGF-1R) inhibitor.

Embodiment 26. The method of Embodiment 25, wherein the quality of life is measured by the Graves' Ophthalmopathy Quality of Life (GO-QoL) assessment, or either the Visual Functioning or Appearance subscale thereof.

Embodiment 27. The method of Embodiment 26, wherein the treatment results in an improvement of ≥8 points on the GO-QoL.

Embodiment 28. The method of Embodiment 26, wherein the treatment results in an improvement on the Functioning subscale of the GO-QoL.

Embodiment 29. The method of Embodiment 26, wherein the treatment results in an improvement on the Appearance subscale of the GO-QoL.

Embodiment 30. The method of any of Embodiments 1-29, wherein the TED is moderate-to-severe TED.

Embodiment 31. The method of any of Embodiments 1-30, wherein the TED is active/acute TED.

Embodiment 32. The method of any of Embodiments 1-30, wherein the TED is inactive/chronic TED.

Embodiment 33. The method of any of Embodiments 1-32, wherein the subject is a subject who has undergone prior treatment with an IGF-1R inhibitor and either did not respond to said prior treatment or relapsed after said prior treatment.

Embodiment 34. The method of any of Embodiments 1-33, wherein the treatment is efficacious for at least 20 weeks beyond the last administered dose.

Embodiment 35. The method of Embodiment 34, wherein the treatment is efficacious for at least 50 weeks beyond the last administered dose.

Embodiment 36. The method of any of Embodiments 1-35 wherein said IGF-1R inhibitor is an antibody or small molecule, with the proviso that the antibody is not teprotumumab.

Embodiment 37. The method of Embodiment 36 wherein said IGF-1R inhibitor is chosen from ganitumab, figitumumab, MEDI-573, cixutumumab, dalotuzumab, robatumumab, AVE1642, BIIB022, xentuzumab, istiratumab, linsitinib, picropodophyllin, BMS-754807, BMS-536924, BMS-554417, GSK1838705A, GSK1904529A, NVP-AEW541, NVP-ADW742, GTx-134, AG1024, KW-2450, PL-2258, NVP-AEW541, NSM-18, AZD3463, AZD9362, B1I885578, B1893923, TT-100, XL-228, and A-928605.

Embodiment 38. The method of Embodiment 36 wherein said IGF-1R inhibitor is an antibody.

Embodiment 39. The method of Embodiment 37 wherein said IGF-1R inhibitor is a human, chimeric human, or humanized monoclonal antibody suitable for human therapy.

Embodiment 40. The method of Embodiment 38 wherein the antibody is administered intravenously (IV) or subcutaneously (SC).

Embodiment 41. The method of Embodiment 39 wherein the antibody is administered IV.

Embodiment 42. The method of Embodiment 40 wherein said antibody is chosen from ganitumab, figitumumab, MEDI-573, cixutumumab, dalotuzumab, robatumumab, AVE1642, BIIB022, xentuzumab, and istiratumab.

Embodiment 43. The method of Embodiment 42 wherein the antibody is ganitumab.

Embodiment 44. The method of Embodiment 43 wherein the ganitumab is dosed at:

a) 1-60 mg/kg or 75-4500 mg IV every 3 weeks; or
b) 0.6-40 mg/kg or 45-3000 mg IV every 2 weeks; or
c) 0.3-20 mg/kg; or 22-1500 mg IV weekly.

Embodiment 45. The method of Embodiment 42 wherein the antibody is figitumumab.

Embodiment 46. The method of Embodiment 45 wherein the figitumumab is dosed at:

a) 1-60 mg/kg or 75-4500 mg IV every 3 weeks; or
b) 0.6-40 mg/kg or 45-3000 mg IV every 2 weeks; or
c) 0.3-20 mg/kg or 22-1500 mg IV weekly.

Embodiment 47. The method of Embodiment 42 wherein the antibody is cixutumumab.

Embodiment 48. The method of Embodiment 47 wherein the cixutumumab is dosed at:

a) 1-45 mg/kg or 75-3400 mg IV every 3 weeks; or
b) 0.6-30 mg/kg or 45-2300 mg IV every 2 weeks; or
c) 0.3-15 mg/kg Or 22-1200 mg IV weekly.

Embodiment 49. The method of Embodiment 42 wherein the antibody is dalotuzumab.

Embodiment 50. The method of Embodiment 49 wherein the dalotuzumab is dosed at:

a) 1-90 mg/kg or 75-6800 mg IV every 3 weeks; or
b) 0.6-60 mg/kg or 45-4500 mg IV every 2 weeks; or
c) 0.3-30 mg/kg or 22-2300 mg IV weekly.

Embodiment 51. The method of Embodiment 42 wherein the antibody is robatumumab.

Embodiment 52. The method of Embodiment 51 wherein the robatumumab is dosed at:

a) 1-75 mg/kg or 75-5700 mg IV every 3 weeks; or
b) 0.6-50 mg/kg or 45-3800 mg IV every 2 weeks; or
c) 0.3-25 mg/kg or 22-1900 mg IV weekly.

Embodiment 53. The method of Embodiment 42 wherein the antibody is xentuzumab.

Embodiment 54. The method of Embodiment 53 wherein the xentuzumab is dosed at:

a) 1-112 mg/kg or 75-8400 mg IV every 3 weeks; or
b) 0.6-75 mg/kg or 45-5700 mg IV every 2 weeks; or
c) 0.3-38 mg/kg or 22-2900 mg IV weekly.

Embodiment 55. The method of Embodiment 42 wherein the antibody is istiratumab.

Embodiment 56. The method of Embodiment 55 wherein the istiratumab is dosed at:

a) 1-112 mg/kg or 75-8400 mg IV every 3 weeks; or
b) 0.6-75 mg/kg or 45-5700 mg IV every 2 weeks; or
c) 0.3-38 mg/kg or 22-2900 mg IV weekly.

Embodiment 57. The method of Embodiment 42 wherein the antibody is AVE1642.

Embodiment 58. The method of Embodiment 57 wherein the AVE1642 is dosed at:

a) 1-60 mg/kg or 75-4500 mg IV every 3 weeks; or
b) 0.6-40 mg/kg or 45-3000 mg IV every 2 weeks; or
c) 0.3-20 mg/kg or 22-1500 mg IV weekly.

Embodiment 59. The method of Embodiment 42 wherein the antibody is BIIB022.

Embodiment 60. The method of Embodiment 59 wherein the BIIB022 is dosed at:

a) 1-75 mg/kg or 75-5700 mg IV every 3 weeks; or
b) 0.6-50 mg/kg; or 45-3800 mg IV every 2 weeks; or
c) 0.3-25 mg/kg or 22-1900 mg IV weekly.

Embodiment 61. The method of Embodiment 48 wherein said IGF-1R inhibitor antibody comprises at least one heavy chain and at least one light chain selected from the selected from the group consisting of:

a) a heavy chain comprising the amino acid sequence of SEQ ID NO:7 and a light chain comprising the amino acid sequence SEQ ID NO:8;
b) a heavy chain comprising the amino acid sequence of SEQ ID NO:15 and a light chain comprising the amino acid sequence SEQ ID NO:16;
c) a heavy chain comprising the amino acid sequence of SEQ ID NO:23 and a light chain comprising the amino acid sequence SEQ ID NO:24;
d) a heavy chain comprising the amino acid sequence of SEQ ID NO:31 and a light chain comprising the amino acid sequence SEQ ID NO:32;
e) a heavy chain comprising the amino acid sequence of SEQ ID NO:39 and a light chain comprising the amino acid sequence SEQ ID NO:40;
f) a heavy chain comprising the amino acid sequence of SEQ ID NO:47 and a light chain comprising the amino acid sequence SEQ ID NO:48;
g) a heavy chain comprising the amino acid sequence of SEQ ID NO:55 and a light chain comprising the amino acid sequence SEQ ID NO:56;
h) a heavy chain comprising the amino acid sequence of SEQ ID NO:63 and a light chain comprising the amino acid sequence SEQ ID NO:64;
i) a heavy chain comprising the amino acid sequence of SEQ ID NO:65 and a light chain comprising the amino acid sequence SEQ ID NO:66; and
j) a heavy chain comprising the amino acid sequence of SEQ ID NO:73 and a light chain comprising the amino acid sequence SEQ ID NO:74.

Embodiment 62. The method of Embodiment 36 wherein said IGF-1R inhibitor is a small molecule.

Embodiment 63. The method of Embodiment 61 wherein said IGF-1R inhibitor is dosed orally.

Embodiment 64. The method of Embodiment 63 wherein said IGF-1R inhibitor is chosen from linsitinib, picropodophyllin, BMS-754807, BMS-536924, BMS-554417, GSK1838705A, GSK1904529A, NVP-AEW541, NVP-ADW742, GTx-134, AG1024, KW-2450, PL-2258, NVP-AEW541, NSM-18, AZD3463, AZD9362, BI885578, BI893923, TT-100, XL-228, and A-928605.

Embodiment 65. The method of Embodiment 64 wherein the IGF-1R inhibitor is linsitinib.

Embodiment 66. The method of Embodiment 65 wherein the linsitinib is dosed at:

a) 10-750 mg orally once daily continuous dosing or 10-1500 mg/day for once daily intermittent dosing (for up to 7 days of every 14 days); or
b) 6-500 mg orally twice daily continuous dosing or 6-1000 mg for twice daily intermittent dosing (for up to 7 days of every 14 days); or
c) 3-250 mg orally three-times daily continuous dosing or 3-500 mg for three-times daily intermittent dosing (for up to 7 days of every 14 days).

Embodiment 67. The method of Embodiment 64 wherein the IGF-1R inhibitor is picropodophyllin.

Embodiment 68. The method of Embodiment 67 wherein the picropodophyllin is dosed:

a) orally once daily at 20-2000 mg; or
b) orally twice daily at 13-1400 mg; or
c) orally three times daily at 6-700 mg.

Embodiment 69. The method of Embodiment 64 wherein the IGF-1R inhibitor is BMS-754807.

Embodiment 70. The method of Embodiment 69 wherein the BMS-754807 is dosed:

a) once daily at 5-600 mg orally; or
b) twice daily at 3-400 mg orally; or
c) three times daily at 1-200 mg.

Embodiment 71. The method of Embodiment 64 wherein the IGF-1R inhibitor is BMS-536924.

Embodiment 72. The method of Embodiment 64 wherein the IGF-1R inhibitor is BMS-554417.

Embodiment 73. The method of Embodiment 64 wherein the IGF-1R inhibitor is GSK1838705A.

Embodiment 74. The method of Embodiment 64 wherein the IGF-1R inhibitor is GSK1904529A.

Embodiment 75. The method of Embodiment 64 wherein the IGF-1R inhibitor is NVP-AEW541.

Embodiment 76. The method of Embodiment 64 wherein the IGF-1R inhibitor is NVP-ADW742.

Embodiment 77. The method of Embodiment 64 wherein the IGF-1R inhibitor is GTx-134.

Embodiment 78. The method of Embodiment 64 wherein the IGF-1R inhibitor is AG1024.

Embodiment 79. The method of Embodiment 64 wherein the IGF-1R inhibitor is PL-2258.

Embodiment 80. The method of Embodiment 64 wherein the IGF-1R inhibitor is NVP-AEW541.

Embodiment 81. The method of Embodiment 64 wherein the IGF-1R inhibitor is NSM-18.

Embodiment 82. The method of Embodiment 64 wherein the IGF-1R inhibitor is AZD3463.

Embodiment 83. The method of Embodiment 64 wherein the IGF-1R inhibitor is AZD9362.

Embodiment 84. The method of Embodiment 64 wherein the IGF-1R inhibitor is BI885578.

Embodiment 85. The method of Embodiment 64 wherein the IGF-1R inhibitor is BI893923.

Embodiment 86. The method of Embodiment 64 wherein the IGF-1R inhibitor is TT-100.

Embodiment 87. The method of Embodiment 64 wherein the IGF-1R inhibitor is XL-228.

Embodiment 80. The method of Embodiment 64 wherein the IGF-1R inhibitor is A-928605.

Embodiment 88. The method of any of Embodiments 71-88 wherein the IGF-1R inhibitor is dosed:

a) once daily at 1-2000 mg orally; or
b) twice daily at 0.6-1400 mg orally; or
c) three times daily at 0.3-700 mg orally.

Embodiment 89. The method of Embodiment 64 wherein the IGF-1R inhibitor is KW-2450.

Embodiment 90. The method of Embodiment 90 wherein the KW-2450 is dosed:

a) once daily at 1-100 mg orally; or
b) twice daily at 0.6-70 mg orally; or
c) three times daily at 0.3-30 mg orally.

Embodiment 91. The method of any of Embodiments 1-30 and 33-35, wherein the TED is inactive/chronic TED, and wherein the IGF-1R inhibitor is teprotumumab.

Also provided herein are pharmaceutical compositions for the treatment of TED comprising an IGF-1R inhibitor.

Embodiment 92. A pharmaceutical composition comprising an amount of an insulin like growth factor-I receptor (IGF-1R) inhibitor that is therapeutically effective:

for treating or reducing the severity of thyroid eye disease (TED) or a symptom thereof,
for reducing proptosis by at least 2 mm in a subject with thyroid eye disease (TED)
for treating or reducing the severity of diplopia in a subject with thyroid eye disease (TED);
for reducing Clinical Activity Score (CAS) of thyroid eye disease (TED);
for a) reducing proptosis by at least 2 mm and b) reducing the clinical activity score (CAS) in a subject with thyroid eye disease (TED); and/or
for improving the quality of life in a subject with thyroid eye disease (TED) wherein the quality of life is measured by the Graves' Ophthalmopathy Quality of Life (GO-QoL) assessment, or either the Visual Functioning or Appearance subscale thereof.

Embodiment 93. The pharmaceutical composition of Embodiment 92, wherein the IGF-1R inhibitor is ganitumab, formulated for administration:

a) 1-60 mg/kg or 75-4500 mg IV every 3 weeks; or
b) 0.6-40 mg/kg or 45-3000 mg IV every 2 weeks; or
c) 0.3-20 mg/kg; or 22-1500 mg IV weekly.

Embodiment 94. The pharmaceutical composition of Embodiment 92, wherein the IGF-1R inhibitor is figitumumab, formulated for administration:

a) 1-60 mg/kg or 75-4500 mg IV every 3 weeks; or
b) 0.6-40 mg/kg or 45-3000 mg IV every 2 weeks; or
c) 0.3-20 mg/kg or 22-1500 mg IV weekly.

Embodiment 95. The pharmaceutical composition of Embodiment 92, wherein the IGF-1R inhibitor is cixutumumab, formulated for administration:

a) 1-45 mg/kg or 75-3400 mg IV every 3 weeks; or
b) 0.6-30 mg/kg or 45-2300 mg IV every 2 weeks; or
c) 0.3-15 mg/kg Or 22-1200 mg IV weekly.

Embodiment 96. The pharmaceutical composition of Embodiment 92, wherein the IGF-1R inhibitor is dalotuzumab, formulated for administration:

a) 1-90 mg/kg or 75-6800 mg IV every 3 weeks; or
b) 0.6-60 mg/kg or 45-4500 mg IV every 2 weeks; or
c) 0.3-30 mg/kg or 22-2300 mg IV weekly.

Embodiment 97. The pharmaceutical composition of Embodiment 92, wherein the IGF-1R inhibitor is robatumumab, formulated for administration:

a) 1-75 mg/kg or 75-5700 mg IV every 3 weeks; or
b) 0.6-50 mg/kg or 45-3800 mg IV every 2 weeks; or
c) 0.3-25 mg/kg or 22-1900 mg IV weekly.

Embodiment 98. The pharmaceutical composition of Embodiment 92, wherein the IGF-1R inhibitor is xentuzumab, formulated for administration:

a) 1-112 mg/kg or 75-8400 mg IV every 3 weeks; or
b) 0.6-75 mg/kg or 45-5700 mg IV every 2 weeks; or
c) 0.3-38 mg/kg or 22-2900 mg IV weekly.

Embodiment 99. The pharmaceutical composition of Embodiment 92, wherein the IGF-1R inhibitor is istiratumab, formulated for administration:

a) 1-112 mg/kg or 75-8400 mg IV every 3 weeks; or
b) 0.6-75 mg/kg or 45-5700 mg IV every 2 weeks; or
c) 0.3-38 mg/kg or 22-2900 mg IV weekly.

Embodiment 100. The pharmaceutical composition of Embodiment 92, wherein the IGF-1R inhibitor is AVE1642, formulated for administration:

a) 1-60 mg/kg or 75-4500 mg IV every 3 weeks; or
b) 0.6-40 mg/kg or 45-3000 mg IV every 2 weeks; or
c) 0.3-20 mg/kg or 22-1500 mg IV weekly.

Embodiment 101. The pharmaceutical composition of Embodiment 92, wherein the IGF-1R inhibitor is BIIB022, formulated for administration at:

a) 1-75 mg/kg or 75-5700 mg IV every 3 weeks; or
b) 0.6-50 mg/kg; or 45-3800 mg IV every 2 weeks; or
c) 0.3-25 mg/kg or 22-1900 mg IV weekly.

Embodiment 102. The pharmaceutical composition of Embodiment 92, wherein the IGF-1R inhibitor is linsitinib, formulated for administration at:

a) 10-750 mg orally once daily continuous dosing or 10-1500 mg/day for once daily intermittent dosing (for up to 7 days of every 14 days); or
b) 6-500 mg orally twice daily continuous dosing or 6-1000 mg for twice daily intermittent dosing (for up to 7 days of every 14 days); or
c) 3-250 mg orally three-times daily continuous dosing or 3-500 mg for three-times daily intermittent dosing (for up to 7 days of every 14 days).

Embodiment 103. The pharmaceutical composition of Embodiment 92, wherein the IGF-1R inhibitor is picropodophyllin, formulated for administration:

a) orally once daily at 20-2000 mg; or
b) orally twice daily at 13-1400 mg; or
c) orally three times daily at 6-700 mg.

Embodiment 104. The pharmaceutical composition of Embodiment 92, wherein the IGF-1R inhibitor is BMS-754807, formulated for administration:

a) once daily at 5-600 mg orally; or b) twice daily at 3-400 mg orally; or c) three times daily at 1-200 mg orally.

Embodiment 105. The pharmaceutical composition of Embodiment 92, wherein the IGF-1R inhibitor is chosen from BMS-536924, BMS-554417, GSK1838705A, GSK1904529A, NVP-AEW541, NVP-ADW742, GTx-134, AG1024, PL-2258, NVP-AEW541, NSM-18, AZD3463, AZD9362, BI885578, BI893923, TT-100, XL-228, and A-928605, formulated for administration:

a) once daily at 1-2000 mg orally; or b) twice daily at 0.6-1400 mg orally; or c) three times daily at 0.3-700 mg orally.

Embodiment 106. The pharmaceutical composition of Embodiment 92, wherein the IGF-1R inhibitor is KW-2450, formulated for administration;

a) once daily at 1-100 mg orally; or b) twice daily at 0.6-70 mg orally; or c) three times daily at 0.3-30 mg orally.

Embodiment 107. The method of Embodiment 57, wherein the AVE1642 antibody comprises a HCDR1 comprising the amino acid sequence of SEQ ID NO:25, a HCDR2 comprising the amino acid sequence of SEQ ID NO:76, a HCDR3 comprising the amino acid sequence of SEQ ID NO:27, a LCDR1 comprising the amino acid sequence of SEQ ID NO:28, a LCDR2 comprising the amino acid sequence of SEQ ID NO:29, and a LCDR3 comprising the amino acid sequence of SEQ ID NO:30.

Embodiment 108. The method of Embodiment 107, wherein the antibody comprises a heavy chain variable domain comprising SEQ ID NO:31 or 78 or 79, and a light chain variable domain comprising SEQ ID NO:32 or 80 or 81 or 82 or 83.

Embodiment 109. The method of Embodiment 108, wherein the antibody comprises a heavy chain variable domain comprising SEQ ID NO:78 and a light chain variable domain comprising SEQ ID NO:80 or 81 or 82 or 83.

Embodiment 110. The method of Embodiment 109, wherein the antibody comprises the light chain variable domain comprising SEQ ID NO:80.

Embodiment 111. The method of Embodiment 109, wherein the antibody comprises the light chain variable domain comprising SEQ ID NO:81.

Embodiment 112. The method of Embodiment 109, wherein the antibody comprises the light chain variable domain comprising SEQ ID NO:82.

Embodiment 113. The method of Embodiment 109, wherein the antibody comprises the light chain variable domain comprising SEQ ID NO:83.

Embodiment 114. The method of any of Embodiments 107-113, wherein the therapeutically effective amount of the AVE1642 antibody comprises a dosage of 1-60 mg/kg or 75-4500 mg IV Q3W; or 0.6-40 mg/kg or 45-3000 mg IV Q2W; or 0.3-20 mg/kg or 22-1500 mg IV QW.

Embodiment 115. The method of any of Embodiments of 107-113, wherein the therapeutically effective amount of the AVE1642 antibody comprises a dosage of 1-10 mg/kg.

Embodiment 116. The method of Embodiment 115, wherein the therapeutically effective amount of the AVE1642 antibody comprises a dosage of 1-5 mg/kg.

Embodiment 117. The method of Embodiment 116, wherein the therapeutically effective amount of the AVE1642 antibody comprises a dosage of about 1 mg/kg, or about 2 mg/kg, or about 3 mg/kg, or about 4 mg/kg, or about 5 mg/kg.

Embodiment 118. The method of any of Embodiments 115-117, wherein the therapeutically effective amount of the AVE1642 antibody is administered every 1, 2, 3, 4, or 5 weeks (i.e., QW, Q2W, Q3W, Q4W, or Q5W).

Embodiment 119. The method of Embodiment 118, wherein the AVE1642 antibody is administered intravenously (IV) or subcutaneously (SC).

Embodiment 120. The method of any of Embodiments 107-113, wherein the therapeutically effective amount of the AVE1642 antibody comprises a dosage of 1-5 mg/kg or 75-375 mg IV Q3W; or 0.6-4 mg/kg or 45-300 mg IV Q2W; or 0.3-3 mg/kg or 22-225 mg IV QW.

Embodiment 121. The method of any of Embodiments 107-120, wherein the AVE1642 antibody further comprises a variant Fc region comprising mutations that substitute a methionine at position 428 with a leucine (Met428Leu) and substitute an asparagine at position 434 with a serine (Asn434Ser), wherein the amino acid substitution numbering is EU as in Kabat.

Embodiment 122. The method of any Embodiments 115-117, wherein the AVE1642 antibody further comprises a variant Fc region comprising mutations that substitute a methionine at position 428 with a leucine (Met428Leu) and substitute an asparagine at position 434 with a serine (Asn434Ser), wherein the amino acid substitution numbering is EU as in Kabat.

Embodiment 123. The method of Embodiment 122, wherein the therapeutically effective amount of the AVE1642 antibody is administered every 1, 2, 3, 4, 5, 6, 7, 8, 9, 10, 11, or 12 weeks (i.e., QW, Q2W, Q3W, Q4W, Q5W, Q6W, Q7W, Q8W, Q9W, Q10W, Q11W, or Q12W).

Embodiment 124. The method of Embodiment 123, wherein the AVE1642 antibody is administered intravenously (IV) or subcutaneously (SC).

Also provided herein are the following embodiments.

Provided herein are methods of treating or reducing the severity of thyroid eye disease (TED), comprising administering to the subject an effective amount of an insulin like growth factor-I receptor (IGF 1R) inhibitor.

In some embodiments, said IGF-1R inhibitor is an antibody.

In some embodiments, said antibody IGF-1R inhibitor is chosen from ganitumab, figitumumab, dusigitumab, cixutumumab, dalotuzumab, robatumumab, AVE1642, BIIB022, and xentuzumab.

In some embodiments, said IGF-1R inhibitor is a small molecule.

In some embodiments, said small molecule IGF-1R inhibitor is chosen from linsitinib, picropodophyllin, BMS-754807, BMS-536924, BMS-554417, GSK1838705A, NVP-AEW541, GTx-134, and AG1024.

Also provided herein is a method of reducing proptosis (e.g., by at least 2 mm) in a subject with thyroid-associated ophthalmopathy thyroid eye disease (TED) comprising administering to the subject an effective amount of an IGF-1R inhibitor.

Also provided herein is a method of reducing proptosis (e.g., by at least 2 mm) and reducing the clinical activity score (CAS) in a subject with thyroid-associated ophthalmopathy thyroid eye disease (TED) comprising administering to the subject an effective amount of an IGF-1R inhibitor.

Also provided herein is a method of treating or reducing the severity of thyroid eye disease (TED) comprising administering to a subject in need thereof, an effective amount of an IGF-1R inhibitor, and wherein the IGF-1R inhibitor (i) reduces proptosis by at least 2 mm; and (ii) reduces the CAS in the subject by at least 2 points (on the 7-point version of the scale—as described below).

Also provided herein is a method of reducing proptosis by at least 4 mm in a subject with thyroid eye disease (TED) comprising administering to the subject an effective amount of an IGF-1R inhibitor.

Also provided herein is a method of treating or reducing the severity of thyroid eye disease (TED) comprising administering to a subject in need thereof an effective amount of an IGF-1R inhibitor, and wherein the IGF-1R inhibitor reduces proptosis by at least 4 mm.

Also provided herein is a method of treating or reducing the severity of diplopia in a subject with thyroid eye disease (TED), comprising administering to the subject an effective amount of an IGF-1R inhibitor.

Also provided herein is a method of reducing the severity of thyroid eye disease (TED) comprising administering to a subject in need thereof an effective amount of a pharmaceutical composition comprising an IGF-1R inhibitor, and a pharmaceutically acceptable excipient or diluent or carrier.

Accordingly, provided herein is a method of reducing proptosis by at least 2 mm in a subject with TED (TAO or GO). The method comprises administering to the subject an effective amount of an IGF-1R inhibitor.

Also provided herein is a method of reducing proptosis by at least 2 mm and reducing the clinical activity score (CAS) in a subject with TED (TAO or GO), comprising administering to the subject an effective amount of an IGF-1R inhibitor.

Also provided herein is a method of treating or reducing the severity of TED (TAO or GO). The method comprises administering to a subject in need thereof, an effective amount of an IGF-1R inhibitor, and wherein the IGF-1R inhibitor (i) reduces proptosis by at least 2 mm; and (ii) reduces the CAS in the subject by at least 2 points (on the 7-point version of the scale).

In some embodiments, the reduction in proptosis or exophthalmos could be greater than 2 mm, for example, 2.2 mm, 2.4 mm, 2.5 mm, 2.6 mm. 2.8 mm, 3 mm, 3.2 mm, 3.4 mm, 3.5 mm, 3.6 mm, 3.8 mm, 4 mm, 4.1 mm, 4.2 mm, 4.3 mm, 4.4 mm, 4.5 mm, 4.6 mm, 4.7 mm, 4.8 mm, 4.9 mm, 5 mm or more than 5 mm.

In some embodiments, the reduction in CAS is by 2 points or more, for example, by 3, 4, 5, 6, or 7 points. In one embodiment, the reduction in CAS is by 2 or more points. In another embodiment, it is by 3 or more points. In yet another embodiment, the reduction in CAS is by 4 or more points.

Also provided herein is a method of reducing proptosis by at least 4 mm in a subject with TED (TAO or GO). The method comprises administering to the subject an effective amount of an IGF-1R inhibitor.

Also provided herein is a method of treating or reducing the severity of TED. The method comprises administering to a subject in need thereof an effective amount of an IGF-1R inhibitor, and wherein the IGF-1R inhibitor reduces proptosis or exophthalmos by at least 3 mm. Also provided herein is a method of treating or reducing the severity of TED. The method comprises administering to a subject in need thereof, an effective amount of an IGF-1R inhibitor, and wherein the IGF-1R inhibitor reduces proptosis or exophthalmos by at least 4 mm.

Also provided herein is a method of treating or reducing the severity of diplopia associated with TED (in a subject with TED and diplopia), comprising administering to the subject, an effective amount of an IGF-1R inhibitor.

Also provided herein is a method of treating or reducing the severity of diplopia in a subject with thyroid eye disease (TED), comprising administering to the subject an effective amount of an IGF-1R inhibitor.

When TED is severe, this active autoimmune disease, characterized by orbital tissue remodeling from activation of TSH and IGF-1 receptors, results in excess extracellular matrix and proptosis/diplopia, a major quality of life (QoL) issue for TED patients.

Also provided herein is a method of treating or reducing the severity of constant diplopia (CD) in a subject with thyroid eye disease (TED), comprising administering to the subject, an effective amount of an IGF-1R inhibitor. Also provided herein is a method of treatment of diplopia comprising administering to the subject, an effective amount of an IGF-1R inhibitor, that results in improved diplopia relative to placebo.

It should be noted that not all subjects respond to administration of the IGF-1R inhibitor in the same manner. When administered to a population of patients, about 20%, 25%, 30%, 35%, 40%, 45%, 50%, 55%, 60%, 65%, 70%, 75%, 80%, 85%, 90%, 95% r 100% f the patients may respond with a reduction in proptosis or exophthalmos by at least 2 mm and a reduction in the CAS by at least 2 points. In some embodiments, the response is seen in at least 20%, or at least 25%, or at least 30%, or at least 35%, or at least 40%, or at least 45%, or at least 50%, or at least 55%, or at least 60%, or at least 65%, or at least 70%, or at least 80% f the patients.

In some embodiments, the IGF-1R inhibitor reduces proptosis by at least 3 mm in at least 25%, 30%, 35%, 40%, 45% 50%, 55%, 60%, 65%, 70%, 75%, 80%, or 85% f the subjects. In some embodiments, the IGF-1R inhibitor reduces proptosis by at least 3.5 mm in at least 25%, 30%, 35%, 40%, 45% 50%, 55%, 60%, 65%, 70%, 75%, 80%, or 85% f the subjects. In some embodiments, the IGF-1R inhibitor reduces proptosis by at least 4 mm in at least 25%, 30%, 35%, 40%, 45% 50%, 55%, 60%, 65%, 70%, 75%, 80%, or 85% f the subjects. In some embodiments, the IGF-1R inhibitor reduces proptosis by at least 4 mm in about 40% f the subjects.

Also provided herein is a method of reducing proptosis in an eye in a subject with thyroid eye disease (TED), thyroid-associated ophthalmopathy (TAO), or Graves' ophthalmopathy (GO) who has previously undergone prior treatment with an IGF-1R inhibitor and either did not respond to said prior treatment or responded to said prior treatment and later relapsed, comprising administering to said subject an effective amount of the IGF-1R inhibitor.

Also provided herein is a method of reducing proptosis by at least 2 mm in an eye without a deterioration of 2 mm or more in the other (or fellow eye) in a subject with TED comprising administering to said subject an effective amount of an IGF-1R inhibitor. The subject is one who has undergone prior treatment with said IGF-1R inhibitor, and either did not respond to said prior treatment or relapsed after said prior treatment.

In some embodiments, the reduction in proptosis or exophthalmos could be greater than 2 mm, for example, 2.2 mm, 2.4 mm, 2.5 mm, 2.6 mm. 2.8 mm, 3 mm, 3.2 mm, 3.4 mm, 3.5 mm, 3.6 mm, 3.8 mm, 4 mm, 4.1 mm, 4.2 mm, 4.3 mm, 4.4 mm, 4.5 mm, 4.6 mm, 4.7 mm, 4.8 mm, 4.9 mm, 5 mm or more than 5 mm.

Also provided herein is a method of reducing Clinical Activity Score (CAS) of thyroid eye disease (TED) in a subject who has undergone prior treatment with an IGF-1R inhibitor, and either did not respond to said prior treatment or relapsed after said prior treatment, comprising administering to a subject in need thereof an effective amount of an IGF-1R inhibitor.

In some embodiments, CAS is reduced in said subject to either one (1) or zero (0) (on the 7-point version of the CAS scale—as described below).

In some embodiments, the reduction in CAS is by 2 points or more, for example, by 3, 4, 5, 6, or 7 points. In one embodiment, the reduction in CAS is by 2 or more points. In another embodiment, it is by 3 or more points. In yet another embodiment, the reduction in CAS is by 4 or more points. In yet another embodiment, the reduction in CAS is by 5 or more points.

In one embodiment, as a result of the treatment, the CAS is reduced to one (1). In another embodiment, as a result of the treatment, the CAS is reduced to zero (0).

Also provided herein is a method of treating or reducing the severity of thyroid eye disease (TED) comprising administering to a subject who has undergone prior treatment with an IGF-1R inhibitor, and either did not respond to said prior treatment or responded to said prior treatment and later relapsed, IGF-1R inhibitor.

Also provided herein is a method of treating or reducing the severity of thyroid eye disease (TED) in a subject who has undergone prior treatment with an IGF-1R inhibitor and either did not respond to said prior treatment or relapsed after said prior treatment comprising administering to a subject in need thereof an effective amount of an IGF-1R inhibitor, and wherein said IGF-1R inhibitor (i) reduces proptosis by at least 2 mm in an eye; (ii) is not accompanied by a deterioration of 2 mm or more in the other (or fellow eye); and (iii) reduces the CAS in said subject to either one (1) or zero (0) (on the 7-point version of the scale—as described below.

Also provided herein is a method of treating or reducing the severity of thyroid eye disease (TED; TAO or GO) comprising administering to a subject in need thereof an effective amount of an IGF-1R inhibitor, wherein said antibody reduces proptosis by at least 2 mm as well as reduces the CAS to either one (1) or zero (0). As stated above, the subject is one who has undergone prior treatment with said IGF-1R inhibitor, and either did not respond to said prior treatment or relapsed after said prior treatment.

Also provided herein is a method of treating or reducing the severity of thyroid eye disease (TED; TAO or GO) in a subject with TED who has previously undergone prior treatment with an IGF-1R inhibitor and either did not respond to said prior treatment or responded to said prior treatment and later relapsed, comprising administering to a subject in need thereof an effective amount of a pharmaceutical composition comprising an IGF-1R inhibitor and a pharmaceutically acceptable excipient or diluent or carrier.

Also provided herein is a method of reducing proptosis in an eye in a subject with thyroid eye disease (TED; TAO or GO) who has previously undergone prior treatment with an IGF-1R inhibitor and either did not respond to said prior treatment or responded to said prior treatment and later relapsed, comprising administering to said subject an effective amount of the IGF-1R inhibitor.

Also provided herein is a method of treating or reducing the severity of thyroid eye disease (TED; TAO or GO) comprising administering to a subject who has undergone prior treatment with an IGF-1R inhibitor, and either did not respond to said prior treatment or responded to said prior treatment and later relapsed, the IGF-1R inhibitor.

Also provided herein is a method of improving the quality of life in a subject with thyroid eye disease (TED; TAO or GO) who has undergone prior treatment with an IGF-1R inhibitor, and either did not respond to said prior treatment or responded to said prior treatment and later relapsed, comprising administering to the subject an effective amount of an IGF-1R inhibitor.

Also provided herein is a method of treating or reducing diplopia or the severity of diplopia in a subject with thyroid eye disease (TED; TAO or GO) who has undergone prior treatment with an IGF-1R inhibitor, and either did not respond to said prior treatment or responded to said prior treatment and later relapsed, comprising administering to the subject an effective amount of an IGF-1R inhibitor.

In some embodiments, the diplopia is constant diplopia. In some embodiments, the diplopia is inconstant diplopia. In some embodiments, the diplopia is intermittent diplopia.

In some embodiments, the improvement in or reduction in severity of diplopia is sustained at least 20, 30, 40, or 50 weeks after discontinuation of IGF-1R inhibitor administration. In some embodiments, the improvement in or reduction in severity of diplopia is sustained 20-30, 30-40, 40-50, or 50-60 weeks after discontinuation of IGF-1R inhibitor administration. In some embodiments, the improvement in or reduction in severity of diplopia is sustained at least 20 weeks after discontinuation of IGF-1R inhibitor administration. In some embodiments, the improvement in or reduction in severity of diplopia is sustained at least 50 weeks after discontinuation of IGF-1R inhibitor administration.

Also provided herein is a method of treating or reducing the severity of constant diplopia (CD) in a subject with thyroid eye disease (TED; TAO or GO) who has undergone prior treatment with an IGF-1R inhibitor, and either did not respond to said prior treatment or responded to said prior treatment and later relapsed, comprising administering to the subject an effective amount of an IGF-1R inhibitor. In some embodiments, the treatment with the IGF-1R inhibitor improves the CD QoL in patients with severe TED.

Also provided herein is a method of treating or reducing the severity of diplopia in a subject with thyroid eye disease (TED; TAO or GO) who has undergone prior treatment with an IGF-1R inhibitor, and either did not respond to said prior treatment or responded to said prior treatment and later relapsed, comprising administering to the subject an effective amount of an IGF-1R inhibitor, that results in improved diplopia relative to placebo which is sustained out to 51 weeks after drug discontinuation.

The IGF-1R inhibitor can be administered in a single dose or in multiple doses. In one embodiment, the IGF-1R inhibitor is administered to the subject in a single dose. In another embodiment, the IGF-1R inhibitor is administered to the subject in multiple doses, spread out over the course of a few days, weeks or months. In some embodiments the IGF-1R inhibitor is administered every week or every 2 weeks or every 3 weeks or every 4 weeks or every 5 weeks or every 6 weeks or every 7 weeks or every 8 weeks or every month or every 2 months or every 3 months.

In some embodiments the IGF-1R inhibitor is administered in multiple doses and the dosage is the same each time. In some embodiments the IGF-1R inhibitor is administered in multiple doses and the dosage at the time of first administration is different (could be higher or lower) from those at subsequent times. In some embodiments the IGF-1R inhibitor is administered in multiple doses and the dosage is adjusted at each administration based on the subject's response to the therapy.

The dosage may further vary between patients, based on different factors such as the age, gender, race, and body weight of each patient. In one embodiment, the dosage varies by body weight of the patient. The dosage could range from about 1 mg of the IGF-1R inhibitor per kilogram of body weight to about 100 mg of the IGF-1R inhibitor per kilogram of body weight. The dosage, could for example, be 1 mg, 2 mg, 3 mg, 5 mg, 7 mg, 10 mg, 12 mg, 15 mg, 17 mg, 20 mg, 22 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg, of the IGF-1R inhibitor per kilogram of body weight.

In some embodiments, the dosage is about 1 mg/kg to about 5 mg/kg of the IGF-1R inhibitor. In some embodiments, the dosage is about 5 mg/kg to about 10 mg/kg of the IGF-1R inhibitor. In some embodiments, the dosage is about 10 mg/kg to about 15 mg/kg of the IGF-1R inhibitor. In some embodiments, the dosage is about 15 mg/kg to about 20 mg/kg of the IGF-1R inhibitor.

In some embodiments where the IGF-1R inhibitor is administered in multiple doses and the dosage at the time of first administration is different from those at subsequent times, the dosage at the time of first administration is about 1 mg/kg to about 5 mg/kg of the IGF-1R inhibitor; or about 5 mg/kg to about 10 mg/kg of the IGF-1R inhibitor; or about 10 mg/kg to about 15 mg/kg of the IGF-1R inhibitor; or about 15 mg/kg to about 20 mg/kg of the IGF-1R inhibitor; or about 20 mg/kg to about 25 mg/kg of the IGF-1R inhibitor. The subsequent dose(s) could be higher or lower than the first dose. In some embodiments, the subsequent dose is about 1 mg/kg to about 5 mg/kg of the IGF-1R inhibitor; or about 5 mg/kg to about 10 mg/kg of the IGF-1R inhibitor; or about 10 mg/kg to about 15 mg/kg of IGF-1R inhibitor; or about 15 mg/kg to about 20 mg/kg of the IGF-1R inhibitor; or about 20 mg/kg to about 25 mg/kg of the IGF-1R inhibitor.

The duration of the treatment would depend on the subject's response to the therapy and can range from about one month or 4 weeks to about 2 years or 100 weeks. In different embodiments, the treatment may be provided over a total duration of about 1 month, 2 months, 3 months, 4 months, 5 months, 6 months, 7 months, 8 months, 9 months, 10 months, 11 months, 1 year, 14 months, 16 months, 18 months, 20 months, 22 months or 2 years. In other embodiments, the treatment may be provided over a total duration of 4, 6, 8, 10, 12, 14, 16, 20, 22, 24, 26, 28, 30, 32, 34, 36, 38, 40, 42, 44, 46, 48, 50, 52 weeks, or extended to 56, 64, 72, 80, 88, 96 or 104 weeks.

The IGF-1R inhibitor may be administered by any suitable route including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions disclosed herein. Solid forms suitable for solution in, or suspension in, liquid vehicles prior to injection may also be used.

Also provided are embodiments wherein any embodiment above may be combined with any one or more of these embodiments, provided the combination is not mutually exclusive. As used herein, two embodiments are "mutually exclusive" when one is defined to be something which is different than the other.

Definitions

To facilitate understanding of the disclosure, a number of terms and abbreviations as used herein are defined below as follows:

As used herein, the term "antibody" encompasses the various forms of antibodies including but not being limited to whole antibodies, monoclonal antibodies, antibody fragments, human antibodies, humanized antibodies, chimeric antibodies and genetically engineered antibodies as long as the characteristic properties such as specificity and IGF-IR inhibitory are retained.

As used herein, the terms "antigen binding fragment," "fragment," and "antibody fragment" are used interchangeably to refer to any fragment that comprises a portion of a full length antibody, generally at least the antigen binding portion or the variable region thereof. Examples of antibody fragments include, but are not limited to, diabodies, single-chain antibody molecules, multispecific antibodies, Fab, Fab', $F(ab')_2$, Fv or scFv. Further, the term "antibody" as used herein includes both antibodies and antigen binding fragments thereof. In addition, antibody fragments comprise single chain polypeptides having the characteristics of a VH chain, namely being able to assemble together with a VL chain or of a VL chain binding to IGF-IR, namely being able to assemble together with a VH chain to a functional antigen binding pocket and thereby providing the property of inhibiting the binding of IGF-I and IGF-II to IGF-IR.

The terms "monoclonal antibody" or "monoclonal antibody composition," as used herein refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light human chain transgene fused to an immortalized cell.

The term "human antibody" as used herein, is intended to include antibodies having variable and constant regions derived from human germline immunoglobulin sequences. The term "humanized antibody" as used herein refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody."

The term "recombinant human antibody," as used herein, is intended to include all human antibodies that are prepared, expressed, created or isolated by recombinant means, such as antibodies isolated from a host cell such as an SP2-0, NS0 or CHO cell or from an animal (e.g., a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

The term "variable region" (variable region of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure.

The CDRs in each chain are held in their three-dimensional structure by the framework regions and form together with the CDRs from the other chain the antigen binding site. The antibody heavy and light chain CDR3 regions play an important role in the binding specificity/affinity of antibodies.

The terms "complementarity determining region," "CDR," "hypervariable region," or "antigen-binding portion of an antibody" are used interchangeably herein and refer to the amino acid residues of an antibody which are responsible for antigen-binding. The hypervariable region comprises amino acid residues from the complementarity determining regions or CDRs. "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. Especially, CDR3 of the heavy chain is the region which contributes most to antigen binding. CDR and FR regions are determined according to the standard definition of Kabat et al., Sequences of Proteins of Immunological Interest, 5th Ed. Public Health Service, National Institutes of Health, Bethesda, MD (1991)) and/or those residues from a "hypervariable loop."

The terms "binding to IGF-IR" or "specific binding to IGF-IR" are used interchangeably herein and mean the binding of the antibody to IGF-IR in an in vitro assay, preferably in a binding assay in which the antibody is bound to a surface and binding of IGF-IR is measured by Surface Plasmon Resonance (SPR). Binding means a binding affinity ($K_D$) of $10^{-8}$ M or less, preferably $10^{-13}$ to $10^{-9}$ M. Binding to IGF-IR can be investigated by a BIAcore assay (Pharmacia Biosensor AB, Uppsala, Sweden). The affinity of the binding is defined by the terms ka (rate constant for the association of the antibody from the antibody/antigen complex), kd (dissociation constant), and $K_D$ (kd/ka). The antibodies used in the methods disclose herein typically show a $K_D$ of about $10^{-9}$ M or less.

The antibodies, or antigen binding fragments thereof, used in the methods disclosed herein inhibit the binding of IGF-I and IGF-II to IGF-IR. The inhibition is measured as $IC_{50}$ in an assay for binding of IGF-I/IGF-II to IGF-IR on cells. Such an assay is known to one of skill in the art and is described, for example, U.S. Pat. No. 7,579,157, which is incorporated herein in its entirety. The $IC_{50}$ values of the antibodies used in the methods disclosed herein for the binding of IGF-I and IGF-II to IGF-IR typically are no more than 2 nM. $IC_{50}$ values are measured as average or median values of at least three independent measurements. Single $IC_{50}$ values may be excluded from the scope.

The term "inhibiting the binding of IGF-I and IGF-II to IGF-IR" as used herein refers to inhibiting the binding of $I^{125}$-labeled IGF-I or IGF-II to IGF-IR presented on the surface of cells in an in vitro assay. Inhibiting means an $IC_{50}$ value of 2 nM or lower.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a subject or patient is intended to include prevention, prophylaxis, attenuation, amelioration and therapy. Treatment may also include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The terms "subject" and "patient" are used interchangeably herein to mean all mammals including humans. Examples of subjects include, but are not limited to, humans, monkeys, dogs, cats, horses, cows, goats, sheep, pigs, and rabbits. In one embodiment, the subject or patient is a human.

The terms "affected with a disease or disorder," "afflicted with a disease or disorder," or "having a disease or disorder" are used interchangeably herein and refer to a subject or patient with any disease, disorder, syndrome or condition. No increased or decreased level of severity of the disorder is implied by the use of one the terms as compared to the other.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

When introducing elements of the present disclosure or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e., A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein in relation to a numerical value x means x±10%.

The term "comprising" encompasses "including" as well as "consisting" e.g., a composition "comprising" X may consist exclusively of X or may include something additional e.g., X+Y.

The word "substantially" does not exclude "completely" e.g., a composition which is "substantially free" from Y may be completely free from Y. Where necessary, the word "substantially" may optionally be omitted where used herein.

An "intention-to-treat" population includes all clinical trial subjects who are randomized according to randomized treatment assignment. Randomized controlled trials often suffer from two major complications, i.e., noncompliance and missing outcomes. One potential solution to this problem is a statistical concept called intention-to-treat (ITT) analysis. ITT analysis ignores noncompliance, protocol deviations, withdrawal, and anything that happens after randomization. ITT analysis maintains prognostic balance generated from the original random treatment allocation. In ITT analysis, estimate of treatment effect is generally conservative. A better application of the ITT approach is possible if complete outcome data are available for all randomized subjects. Per-protocol population is defined as a subset of the ITT population who completed the study without any major protocol violations. See, e.g., Gupta SK, Intention-to-treat concept: A review, Perspect Clin Res. 2011 July-September; 2(3): 109-112.

As used herein, "Thyroid Eye Disease" (TED), "Thyroid-associated Ophthalmopathy" (TAO), "Thyroid Inflammatory Eye Disease (TIED)," "Graves' Ophthalmopathy" (GO) or "Graves' Orbitopathy" (GO) refer to the same disorder or condition and are used interchangeably. They all refer to the inflammatory orbital pathology associated with some autoimmune thyroid disorders, most commonly with "Graves' Disease" (GD), but sometimes with other diseases, e.g. Hashimoto's thyroiditis.

The terms "proptosis" and "exophthalmos" (also known as exophthalmus, exophthalmia, or exorbitism) refer to the forward projection, displacement, bulging, or protrusion of an organ. As used herein, the terms refer to the forward projection, displacement, bulging, or protrusion of the eye anteriorly out of the orbit. Proptosis and exophthalmos are considered by some of skill in the art to have the same meaning and are often used interchangeably, while others attribute subtle differences to their meanings. Exophthalmos is used by some to refer to severe proptosis; or to refer to endocrine-related proptosis. Yet others use the term exophthalmos when describing proptosis associated with the eye, in, for example, subjects with TED (TAO or GO).

As used herein, the terms "proptosis" and "exophthalmos" are used interchangeably and refer to the forward projection, displacement, bulging, or protrusion of the eye anteriorly out of the orbit. Owing to the rigid bony structure of the orbit with only anterior opening for expansion, any increase in orbital soft tissue contents taking place from the side or from behind will displace the eyeball forward. Proptosis or exophthalmos can be the result of a several disease processes including infections, inflammations, tumors, trauma, metastases, endocrine lesions, vascular diseases & extra orbital lesions. TED (TAO or GO) is currently recognized as the most common cause of proptosis in adults. Exophthalmos can be either bilateral, as is often seen in TED (TAO or GO), or unilateral (as is often seen in an orbital tumor).

Measurement of the degree of exophthalmos can be performed using an exophthalmometer, an instrument used for measuring the degree of forward displacement of the eye. The device allows measurement of the forward distance of the lateral orbital rim to the front of the cornea.

Computed tomography (CT) scanning and Magnetic resonance imaging (MRI) may also be used in evaluating the degree of exophthalmos or proptosis. CT scanning is an excellent imaging modality for the diagnosis of TED (TAO or GO). In addition to allowing visualization of the enlarged extraocular muscles, CT scans provide the surgeon or clinician with depictions of the bony anatomy of the orbit when an orbital decompression is required. MRI, with its multiplanar and inherent contrast capabilities, provides excellent imaging of the orbital contents without the radiation exposure associated with CT scan studies. MRI provides better imaging of the optic nerve, orbital fat, and extraocular muscle, but CT scans provide better views of the bony architecture of the orbit.

Orbital ultrasonography can also be a used for the diagnosis and evaluation of TED (TAO or GO), because it can be performed quickly and with a high degree of confidence. High reflectivity and enlargement of the extraocular muscles are assessed easily, and serial ultrasonographic examinations can also be used to assess progression or stability of the ophthalmopathy.

Based on the technologies currently available, or that will become available in the future, one of skill in the art would be capable of determining the best modality for diagnosing and evaluating the extent of proptosis or exophthalmos.

Although it is generally accepted that the normal range of proptosis is 12-21 mm, it must be noted that the value for a normal person varies by age, gender and race. For example, in normal adult white males, the average distance of globe protrusion is 16.5 mm, with the upper limit of normal at 21.7 mm. In adult African Americans it averages 18.2 mm, with an upper normal limit of 24.1 mm in males and 22.7 mm in females. In Mexican adults, males averaged 15.2 mm and females averaged 14.8 mm and in Iran, for the age group of 20-70 years, the average was 14.7 mm. In Taiwanese adults, comparing normal subjects to those with Graves' Ophthalmopathy, the normal group had an average reading of 13.9 mm versus 18.3 mm for the TED group.

Even within a group of people, there can be variability. Four ethnic groups in Southern Thailand had exophthalmometry measurement averages ranging from 15.4 mm to 16.6 mm. In 2477 Turkish patients, the median measurement was 13 mm, with an upper limit of 17 mm; and in a Dutch study, the upper limit was 20 mm in males and 16 mm in females.

Although the average and upper limits for exophthalmos or proptosis vary widely, it is accepted in the field that a difference greater than 2 mm between the eyes is significant and not normal.

One of skill in the art, for example an ophthalmologist, surgeon or other clinician skilled in the knowledge and treatment of eye disorders would know what a normal value of proptosis is based on the age, gender and race of the subject and have the ability to diagnose or evaluate the presence or absence of proptosis as well as track its progression.

Activity Measures or Assessments

Several classification systems have been conceived to assess the clinical manifestations of TED (TAO or GO). In 1969, Werner reported the NOSPECS Classification (No physical signs or symptoms, Only signs, Soft tissue involvement, Proptosis, Extraocular muscle signs, Corneal involvement, and Sight loss) (Werner, S. C. *American Journal of Ophthalmology,* 1969, 68, no. 4, 646-648.)

The modified NOSPECS was also published by Werner in 1977 and has been broadly used since then (Werner, S. C. *American Journal of Ophthalmology,* 1977, 83, no. 5, 725-727). This classification grades for clinical severity and does not provide a means of distinguishing active TED (inflammatory progressive) from inactive TED (noninflammatory stationary). Therefore, the indication for treatments used to be based exclusively in the severity of symptoms without consideration whether the disease was active or inactive. In 1989, Mourits et al. described the Clinical Activity Score (CAS) (Mourits et al., *British Journal of Ophthalmology,* 1989, 73, no. 8, 639-644) as a way of assessing the degree of active disease. This score, based on the classical signs of acute inflammation (pain, redness, swelling, and impaired function) was proposed as a clinical classification to discriminate easily between active and inactive disease and was modified in 1997 (Mourits et al., *Clinical Endocrinology,* 1997. 47, no. 1, 9-14). This protocol is further described below.

As used herein, the term CAS refers to the protocol described and scored as disclosed below. According to this protocol, one point is given for the presence of each of the parameters assessed in the list below. The sum of all points defines clinical activity and provides the CAS. For patients assessed for the first time only items 1-7 are scored. A CAS≥3/7 indicates active GO. For patients that are assessed for the second or subsequent time (typically, 1-3 months later), items 8-10 are also scored; and a CAS≥4/10 indicates active disease. A ten-item CAS scale exists as well, but in clinical trials, the 7-item scale is generally used, being more amenable to longitudinal studies involving multiple assessments.

The CAS consists of seven components:

1. spontaneous retrobulbar pain,
2. pain on attempted eye movements (upward, side-to-side, and downward gazes),
3. conjunctival redness,
4. redness of the eyelids,
5. chemosis (conjunctival swelling/edema),
6. swelling of the caruncle/plica, and
7. swelling of the eyelids.

Each component is scored as present (1 point) or absent (0 points). The score at each efficacy assessment is the sum of all items present; giving a range of 0-γ, where 0 or 1 constitutes inactive disease and 7 severe active ophthalmopathy. A change of >2 points is considered clinically meaningful.

Item 1, spontaneous orbital pain could be a painful, or oppressive feeling on, or behind, the globe. This pain may be caused by the rise in intraorbital pressure, when the orbital tissues volume increases through excess synthesis of extracellular matrix, fluid accumulation, and cellular infiltration and expansion. Item 2, gaze evoked orbital pain, could be pain in the eyes when looking, or attempting to look, up, down or sideways, i.e., pain with upward, downward, or lateral eye movement, or when attempting upward, downward, or lateral gaze. This kind of pain could arise from the stretching of the inflamed muscle(s), especially on attempted up-gaze. The 'stretching pain' cannot be provoked by digital pressing on the eyeball, as would be expected if it were a manifestation of the raised intraorbital pressure. Both kinds of pain can be reduced after anti-inflammatory treatment. These kinds of pain are therefore considered to be directly related to autoimmune inflammation in the orbit and thus useful in assessing TED activity.

Swelling in TED (TAO or GO) is seen as chemosis (edema of the conjunctiva) and swelling of the caruncule and/or plica semilunaris. Both are signs of TED activity. Swollen eyelids can be caused by edema, fat prolapse through the orbital septum, or fibrotic degeneration. In addition to swelling, other symptoms indicative of active TED include redness and/or pain of the conjunctiva, eyelid, caruncule and/or plica semilunaris.

Other grading systems have also been developed for the assessment of TED (TAO or GO). The VISA Classification (vision, inflammation, strabismus, and appearance) (Dolman, P. J., and Rootman, J., *Ophthalmic Plastic and Reconstructive Surgery,* 2006, 22, no. 5, 319-324 and Dolman, P. J., *Best Practice & Research Clinical Endocrinology & Metabolism,* 2012, 26, no. 3, 229-248) and the European Group of Graves' Orbitopathy (EUGOGO) Classification (Bartalena, L., et al., *European Journal of Endocrinology,* 2008, 158, no. 3, 273-285) are two such examples. Both systems are grounded in the NO SPECS and CAS classifications and use indicators to assess the signs of activity and the degree of severity. More importantly, they allow the clinician to guide the treatment of the patient with GO. VISA is more commonly used in North America and Canada while EUGOGO is in Europe. Since the VISA and EUGOGO protocols are not interchangeable, only one of them should be employed as a reference in a specific patient.

Graves Ophthalmopathy Quality of Life (GO-QoL)

In addition to proptosis (or exophthalmos) and CAS, quality of life (QoL) was also evaluated with the use of the Graves' ophthalmopathy quality of life (GO-QoL) questionnaire. This questionnaire is designed to determine the improved quality of life after treatment. In some embodiments, questionnaire may determine the decreased or lack of side effects after being treated with an antibody, or an antigen binding fragment thereof, according to the methods disclosed herein, as compared to treatment with glucocorticoids.

The GO-QoL questionnaire has two self-assessment subscales. The first relates to the impact of visual function on daily activities, while the second relates to the impact of self-perceived appearance. Each subscale has 8 questions which are answered with: (i) yes—very much so; (ii) yes—a little; or (iii) no—not at all. Each question is scored 0-2, respectively, and the total raw score is then mathematically transformed to a 0-100 scale, where 0 represents the most negative impact on quality of life, and 100 represents no impact. A change of >8 points on the 0-100 scale is considered to be clinically meaningful. The combined score takes raw scores from both subscales and again transforms them to a single 0-100 scale.

Severity Measures

For lid aperture, the distance between the lid margins are measured (in mm) with the patient looking in the primary position, sitting relaxed, and with distant fixation.

For swelling of the eyelids, the measure/evaluation is either "absent/equivocal," "moderate," or "severe."

Redness of the eyelids is either absent or present.

Redness of the conjunctivae is either absent or present.

Conjunctival edema is either absent or present.

Inflammation of the caruncle or plica is either absent or present.

Exophthalmos was measured in millimeter using the same Hertel exophthalmometer and same intercanthal distance for an individual patient.

Subjective diplopia is scored from 0 to 3 (0=no diplopia; 1=intermittent, i.e., diplopia in primary position of gaze, when tired or when first awakening; 2=inconstant, i.e., diplopia at extremes of gaze; 3=constant, i.e., continuous diplopia in primary or reading position).

For eye muscle involvement, the ductions are measured in degrees.

Corneal involvement is either absent/punctate or keratopathy/ulcer.

For optic nerve involvement, .i.e., best-corrected visual acuity, color vision, optic disc, relative afferent pupillary defect, the condition is either absent or present. In addition, visual fields are checked if optic nerve compression was suspected.

Severity Classification

Sight-threatening thyroid eve disease: Patients with dysthyroid optic neuropathy (DON) and/or corneal breakdown. This category warranted immediate intervention.

Moderate-to-severe thyroid eye disease: Patients without sight-threatening disease whose eye disease had sufficient impact on daily life to justify the risks of immunosuppression (if active) or surgical intervention (if inactive). Patients with moderate-to-severe thyroid eye disease usually had any one or more of the following: lid retraction≥2 mm, moderate or severe soft tissue involvement, exophthalmos≥3 mm above normal for race and gender, inconstant or constant diplopia.

Mild thyroid eye disease: Patients whose features of thyroid eye disease have only a minor impact on daily life insufficient to justify immunosuppressive or surgical treatment. They usually have only one or more of the following: minor lid retraction (<2 mm), mild soft tissue involvement, exophthalmos<3 mm above normal for race and gender, transient or no diplopia, and corneal exposure responsive to lubricants.

Assessment of Gorman Grading of Diplopia

The Gorman assessment of subjective diplopia includes four categories: no diplopia (absent), diplopia when the patient is tired or awakening (intermittent), diplopia at extremes of gaze (inconstant), and continuous diplopia in the primary or reading position (constant). Patients are scored according to which grade of diplopia they are experiencing. An improvement of ≥1 grade is considered clinically meaningful.

Additional testing, including clinical trial protocols and criteria and the lead-in study, which can be performed to determine efficacy for the treatment of TED can be found in US20190225696A1, which is hereby incorporated by reference in its entirety.

Further, the IGR-1R inhibitors described herein may be useful for the treatment of TED in subjects who were either proptosis non-responders (<2 mm reduction in proptosis in the study eye) in the lead-in study or were proptosis responders in the lead-in study but meet the criteria for re-treatment due to relapse.

Antibodies

The sequences of the heavy chains and light chains of examples of antibodies that may be used in the methods disclosed herein, each comprising three CDRs on the heavy chain and three CDRs on the light chain are provided below. The sequences of the CDRs, heavy chains, light chains as well as the sequences of the nucleic acid molecules encoding the CDRs, heavy chains and light chains of the antibodies are disclosed in the sequence listing. The CDRs of the antibody heavy chains are referred to as CDRH1 (or HCDR1), CDRH2 (or HCDR2) and CDRH3 (or HCDR3), respectively. Similarly, the CDRs of the antibody light chains are referred to as CDRL1 (or LCDR1), CDRL2 (or LCDR2) and CDRL3 (or LCDR3), respectively.

Variant antibodies are also included within the scope of the disclosure. Thus, variants of the sequences recited in the application are also included within the scope of the disclosure. Such variants include natural variants generated by somatic mutation in vivo during the immune response or in vitro upon culture of immortalized B cell clones. Alternatively, variants may arise due to the degeneracy of the genetic code or may be produced due to errors in transcription or translation.

Further variants of the antibody sequences having improved affinity and/or potency may be obtained using methods known in the art and are included within the scope of the disclosure. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences disclosed herein are also within the scope of the disclosure.

In one embodiment variant antibody sequences may share 70% r more (i.e. 75%, 80%, 85%, 90%, 95%, 97%, 98%, 99% r more) amino acid sequence identity with the sequences recited in the application. In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Antibodies, or antigen binding fragments thereof, used with the methods disclosed herein can be of any isotype (e.g., IgA, IgG, IgM; i.e., an a, 7 or p heavy chain). In one embodiment the antibody is IgG. Within the IgG isotype, antibodies may be IgG1, IgG2, IgG3 or IgG4 subclass. The antibodies may have a κ or a λ light chain.

The antibodies, or an antigen binding fragments thereof, used with the methods disclosed herein can be administered by any route known to one of skill in the art.

Antibody Fc Variants and Half-Life

In immunoglobulins, such as IgG, a site in the Fc region of the heavy chain mediates interaction with the neonatal receptor (FcRn). Binding to FcRn recycles endocytosed antibody from the endosome back to the bloodstream and plays a key role in antibody transport. This process, coupled with preclusion of kidney filtration due to the large size of the full-length molecule, results in favorable antibody serum half-lives ranging from one to three weeks in vivo. Thus, the fidelity of this region on Fc is important for the clinical properties of antibodies.

Other properties of the antibody may determine its clearance rate (e.g. stability and half-life) in vivo. In addition to antibody binding to the FcRn receptor, other factors that contribute to clearance and half-life are serum aggregation, enzymatic degradation in the serum, inherent immunogenicity of the antibody leading to clearing by the immune system, antigen-mediated uptake, FcR (non-FcRn) mediated uptake and non-serum distribution (e.g. in different tissue compartments).

Accordingly, one means by which the pharmacokinetics (PK) and pharmacodynamics (PD) of a therapeutic antibody can by changed is by increasing the serum half-life of the antibody by altering the heavy constant domains within the Fc. In addition, due to the methodologies outlined herein, the possibility of immunogenicity resulting from the FcRn variants is significantly reduced by importing variants from different IgG isotypes such that serum half-life is increased without introducing significant immunogenicity.

The substitutions in the Fc domains are chosen such that the resultant proteins show improved serum half-life in vivo as compared to the wild type protein. In order to increase the retention of the Fc proteins in vivo, the increase in binding affinity must be at around pH 6 while maintaining lower affinity at around pH 7.4. Without being limited to theory, Fc regions are believed to have longer half-lives in vivo because binding to FcRn at pH 6 in an endosome sequesters the Fc. The endosomal compartment then recycles the Fc to the cell surface. Once the compartment opens to the extracellular space, the higher pH (~7.4) induces the release of Fc back into the blood. The increased affinity of Fc for FcRn at pH 7.4 is thought to forbid the release of the Fc back into the blood. As a result, Fc mutations that increase Fc's half-life in vivo generally increase FcRn binding at the lower pH while still allowing release of Fe at higher pH. The amino acid histidine changes its charge state in the pH range of 6.0 to 7.4. Therefore, it is not surprising to find histidine residues at important positions in the Fc/FcRn complex.

In some embodiments, the increase in FcRn binding over wild type specifically at lower pH (~6.0) facilitates Fc/FcRn binding in the endosome. In some embodiments, Fc variants with altered FcRn binding can have altered binding to another class of Fc receptors, the FcγR's (FcgammaR's) as differential binding to FcγR5, particularly increased binding to FcγRIIIb and decreased binding to FcγRIIb, has been shown to result in increased efficacy.

In some embodiments, importation of substitutions at particular positions from one IgG isotype into another can be achieved, thus reducing or eliminating the possibility of unwanted immunogenicity being introduced into the variants. That is, IgG1 is a common isotype for therapeutic antibodies for a variety of reasons, including high effector function. IgG2 residues at particular positions can be introduced into the IgG1 backbone to result in a protein that exhibits longer serum half-life.

In some embodiments, non-isotypic amino acid changes are made, to improve binding to FcRn and/or to increase in vivo serum half-life, and/or to allow accommodations in structure for stability, etc.

As will be appreciated by those in the art and described below, a number of factors contribute to the in vivo clearance, and thus the half-life, of antibodies in serum. One factor involves the antigen to which the antibody binds; that is, antibodies with identical constant regions but different variable regions (e.g., Fv domains), may have different half-lives due to differential ligand binding effects. However, the present disclosure demonstrates that while the absolute half-life of two different antibodies may differ due to these antigen specificity effects, the FcRn variants described herein, can transfer to different ligands to give the same trends of increasing half-life. That is, in general, the relative "order" of the FcRn binding/half-life increases will track to antibodies with the same variants of antibodies with different Fvs as is discussed herein.

Fc variants within a therapeutic antibody are made by introducing amino acid mutations into the parent molecule. "Mutations" in this context are usually amino acid substitutions, although as shown herein, deletions and insertions of amino acids can also be done and thus are defined as mutations.

The Fc variant antibodies of the disclosure show increased binding to FcRn and/or increased in vivo serum half-life. By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. In some cases, the FcRn variants bind to the human FcRn receptor, or it may be desirable to design variants that bind to rodent or primate receptors in addition, to facilitate clinical trials.

In some embodiments, the present disclosure provides compositions and methods of administering an antibody to a subject, where the antibody comprises a variant Fc region as compared to a parent Fc region, wherein the variant Fc region comprises a first mutation that is a leucine at position 428 and a second mutation that is a serine at position 434, where the antibody has increased serum half-life as compared to an antibody comprising the parent Fc region, and wherein numbering is according to the EU index. In some embodiments, the antibody disclosed herein comprises a variant Fc region comprising mutations that substitute a methionine at position 428 with a leucine (Met428Leu) and substitutes an asparagine at position 434 with a serine (Asn434Ser). Numbering is EU as in Kabat, and it is understood that the substitution is non-native to the starting molecule. As has been shown previously, these FcRn substitutions work in IgG1, IgG2 and IgG1/G2 hybrid backbones, and are specifically included for IgG3 and IgG4 backbones and derivatives of any IgG isoform as well.

The present disclosure includes variants of Fc domains, including those found in antibodies, Fc fusions, and immuno-adhesions, which have an increased binding to the FcRn receptor. As noted herein, binding to FcRn results in longer serum retention in vivo. A variety of such substitutions—including those related to M428L/N434S—are known and described in U.S. Pat. Nos. 7,317,091; 8,084,582; and 8,101,720; 8,188,231; 8,367,805; and 8,546,543, each of which is incorporated herein by reference in their entirety.

Dosing and Administration

The compound, antibody, or an antigen binding fragment thereof, can be administered in a single dose or in multiple doses. In some embodiments, the therapeutic antibody is administered to the subject in a single dose. In some embodiments, the therapeutic antibody is administered to the subject in multiple doses, spread out over the course of a few days, weeks or months. In some embodiments the antibody, or an antigen binding fragment thereof, is administered every week or every 2 weeks or every 3 weeks or every 4 weeks or every 5 weeks or every 6 weeks or every 7 weeks or every 8 weeks or every month or every 2 months or every 3 months.

In some embodiments the antibody, or an antigen binding fragment thereof, is administered in multiple doses and the dosage is the same each time. In some embodiments the antibody, or an antigen binding fragment thereof, is administered in multiple doses and the dosage at the time of first administration is different (could be higher or lower) from those at subsequent times. In some embodiments the antibody, or an antigen binding fragment thereof, is administered in multiple doses and the dosage is adjusted at each administration based on the subject's response to the therapy.

The dosage may further vary between patients, based on different factors such as the age, gender, race, and body weight of each patient. In some embodiments, the dosage varies by body weight of the patient. The dosage could range from about 1 mg of the antibody, or an antigen binding fragment thereof, per kilogram of body weight to about 100 mg of the antibody, or an antigen binding fragment thereof, per kilogram of body weight. The dosage, could for example, be 1 mg, 2 mg, 3 mg, 5 mg, 7 mg, 10 mg, 12 mg, 15 mg, 17 mg, 20 mg, 22 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg, of the antibody, or an antigen binding fragment thereof, per kilogram of body weight.

In some embodiments, the dose is about 0.3 mg/kg to about 10 mg/kg of the antibody, or an antigen binding fragment thereof. In some embodiments, the dosage is about 0.3 mg/kg to about 5 mg/kg of the antibody, or an antigen binding fragment thereof. In some embodiments, the dosage is about 0.3 mg/kg to about 1 mg/kg of the antibody, or an antigen binding fragment thereof. The dosage, could for example, be about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, 1.6 mg/kg, 1.7 mg/kg, 1.8 mg/kg, 1.9 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg, or any number of tenths of a mg/kg in between the foregoing, of the antibody, or an antigen binding fragment thereof. In some embodiments, the dose is administered every week.

In some embodiments, the dose is about 0.6 mg/kg to about 20 mg/kg of the antibody, or an antigen binding fragment thereof. In some embodiments, the dosage is about 0.6 mg/kg to about 5 mg/kg of the antibody, or an antigen binding fragment thereof. In some embodiments, the dosage is about 0.6 mg/kg to about 10 mg/kg of the antibody, or an antigen binding fragment thereof. The dosage, could for example, be about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, 1.6 mg/kg, 1.7 mg/kg, 1.8 mg/kg, 1.9 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg, or any number of tenths of a mg/kg in between the foregoing, of the antibody, or an antigen binding fragment thereof. In some embodiments, the dose is administered every two weeks.

In some embodiments, the dose is about 1 mg/kg to about 30 mg/kg of the antibody, or an antigen binding fragment thereof. In some embodiments, the dose is about 5 mg/kg to about 30 mg/kg of the antibody, or an antigen binding fragment thereof. In some embodiments, the dose is about 10 mg/kg to about 30 mg/kg of the antibody, or an antigen binding fragment thereof. The dosage, could for example, be about 1 mg/kg, about 2 mg/kg, about 3 mg/kg, about 5 mg/kg, about 7 mg/kg, about 10 mg/kg, about 12 mg/kg, about 15 mg/kg, about 17 mg/kg, about 20 mg/kg, about 22 mg/kg, about 25 mg/kg, or about 30 mg/kg, or any integer and/or number of tenths of a mg/kg in between the foregoing, of the antibody, or an antigen binding fragment thereof. In some embodiments, the dose is administered every three weeks.

In some embodiments, the dose is about 1.2 mg/kg to about 40 mg/kg of the antibody, or an antigen binding fragment thereof. In some embodiments, the dose is about 5 mg/kg to about 40 mg/kg of the antibody, or an antigen binding fragment thereof. In some embodiments, the dose is about 10 mg/kg to about 40 mg/kg of the antibody, or an antigen binding fragment thereof. In some embodiments, the dose is about 20 mg/kg to about 40 mg/kg of the antibody, or an antigen binding fragment thereof. In some embodiments, the dose is about 25 mg/kg to about 40 mg/kg of the antibody, or an antigen binding fragment thereof. The dosage, could for example, be about 1 mg/kg, about 2 mg/kg, about 3 mg/kg, about 5 mg/kg, about 7 mg/kg, about 10 mg/kg, about 12 mg/kg, about 15 mg/kg, about 17 mg/kg, about 20 mg/kg, about 22 mg/kg, about 25 mg/kg, about 27 mg/kg, about 30 mg/kg, about 32 mg/kg, about 35 mg/kg, about 37 mg/kg, or about 40 mg/kg, or any integer and/or number of tenths of a mg/kg in between the foregoing, of the antibody, or an antigen binding fragment thereof. In some embodiments, the dose is administered every four weeks.

In some embodiments, the dosage is about 1 mg/kg to about 5 mg/kg of the antibody, or an antigen binding fragment thereof. In some embodiments, the dosage is about 5 mg/kg to about 10 mg/kg of the antibody, or an antigen binding fragment thereof. In some embodiments, the dosage is about 10 mg/kg to about 15 mg/kg of the antibody, or an antigen binding fragment thereof. In some embodiments, the dosage is about 15 mg/kg to about 20 mg/kg of the antibody, or an antigen binding fragment thereof.

In some embodiments, the dosage is about 1 mg/kg to about 5 mg/kg of the antibody, or an antigen binding fragment thereof. In some embodiments, the dosage is about 5 mg/kg to about 10 mg/kg of the antibody, or an antigen binding fragment thereof. In some embodiments, the dosage is about 10 mg/kg to about 15 mg/kg of the antibody, or an antigen binding fragment thereof. In some embodiments, the dosage is about 15 mg/kg to about 20 mg/kg of the antibody, or an antigen binding fragment thereof.

In some embodiments the antibody, or an antigen binding fragment thereof, is administered in multiple doses and the dosage at the time of first administration is different from those at subsequent times, the dosage at the time of first administration is about 1 mg/kg to about 5 mg/kg of the antibody, or an antigen binding fragment thereof, or about 5 mg/kg to about 10 mg/kg of the antibody, or an antigen binding fragment thereof, or about 10 mg/kg to about 15 mg/kg of the antibody, or an antigen binding fragment thereof, or about 15 mg/kg to about 20 mg/kg of the antibody, or an antigen binding fragment thereof, or about 20 mg/kg to about 25 mg/kg of the antibody, or an antigen binding fragment thereof. The subsequent dose(s) could be higher or lower than the first dose. In some embodiments, the subsequent dose is about 1 mg/kg to about 5 mg/kg of the antibody, or an antigen binding fragment thereof, or about 5 mg/kg to about 10 mg/kg of the antibody, or an antigen binding fragment thereof, or about 10 mg/kg to about 15 mg/kg of the antibody, or an antigen binding fragment thereof, or about 15 mg/kg to about 20 mg/kg of the antibody, or an antigen binding fragment thereof, or about 20 mg/kg to about 25 mg/kg of the antibody, or an antigen binding fragment thereof.

Small molecule compounds may be administered orally, via injection, etc. at a dose of from 0.01 to 500 mg/kg per day and/or from 0.1 mg to 5 g per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, for example around 10 mg to 200 mg.

The amount of active ingredient that may be combined with the carrier materials to produce a single dosage form will vary depending upon the host treated and the particular mode of administration. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Additional dosage ranges are provided throughout this disclosure.

The duration of the treatment depends on the subject's response to the therapy and can range from about one month or 4 weeks to about 2 years or 100 weeks. In some embodiments, the treatment may be provided over a total duration of about 1 month, 2 months, 3 months, 4 months, 5 months, 6 months, 7 months, 8 months, 9 months, 10 months, 11 months, 1 year, 14 months, 16 months, 18 months, 20 months, 22 months or 2 years. In some embodiments, the treatment may be provided over a total duration of 4, 6, 8, 10, 12, 14, 16, 20, 22, 24, 26, 28, 30, 32, 34, 36, 38, 40, 42, 44, 46, 48, 50, 52 weeks, or extended to 56, 64, 72, 80, 88, 96 or 104 weeks.

In some embodiments, the antibody, or an antigen binding fragment thereof, is administered for a duration of 24 weeks at intervals of 3 weeks starting with an initial dose of 10 mg per kilogram of body weight, followed by 20 mg per kilogram for seven additional treatments. In some embodiments, the slam molecule compound is administered daily (QD), twice daily, (BID) or thrice daily (TID) for an appropriate duration, e.g., 24 weeks.

The compound, antibody, or an antigen binding fragment thereof, may be administered by any suitable route including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions disclosed herein. Typically, the therapeutic antibody may be prepared as a freeze-dried (lyophilized) powder or as an injectable, either as a liquid solution or suspension. Solid forms suitable for solution in, or suspension in, liquid vehicles prior to injection may also be used.

Pharmaceutical Compositions

The pharmaceutical compositions used in the methods disclosed herein comprise one or more of: the antibodies or antibody fragments described above and a pharmaceutically acceptable carrier or excipient. Although the carrier or excipient may facilitate administration, it should not itself induce the production of antibodies harmful to the subject or individual receiving the composition; nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles, and are known to one of skill in the art.

The antibodies, or an antigen binding fragments thereof, or pharmaceutical compositions used with the methods disclosed herein may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions disclosed herein. Typically, the therapeutic compositions may be prepared as injectables, either as liquid solutions or suspensions. Solid forms suitable for solution in, or suspension in, liquid vehicles prior to injection may also be prepared.

In one embodiment, the antibody, or an antigen binding fragment thereof, or pharmaceutical composition is administered intravenously. In another embodiment, the antibody, or an antigen binding fragment thereof, or pharmaceutical composition is administered by intravenous infusion.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation, but which release the antibody once it has been absorbed from the gastrointestinal tract.

For larger molecular weight moieties such as mAbs (~150 kDa), the SC capillaries have low passive permeability; absorption of mAbs into systemic circulation occurs via lymphatic uptake from the interstitial space, as well as via active transport by the neonatal Fc receptor (FcRn) across the capillary endothelia. The extracellular matrix of the subcutaneous tissue also limits the injection of larger volumes (>1-2 mL) SC generally; coformulation with a recombinant hyaluronidase or soluble fragment thereof such as rHuPH20 can permit higher bioavailability. Additionally, physiochemical properties of mAbs, including charge, hydrophobicity, and stability, affect the rate and extent of their SC absorption; for example, the combination of high positive charge and hydrophobic interaction can reduce the rate absorption.

In some embodiments, pharmaceutical compositions suitable for use in the methods disclosed herein are formulated for subcutaneous administration. Examples of formulations suitable for subcutaneous administration include, but are not limited to, solutions, suspensions, emulsions, and dry products that can be dissolved or suspended in a pharmaceutically acceptable carrier for injection. Antibodies have been, and may be, formulated for subcutaneous administration using methods known in the art.

Pharmaceutical compositions suitable for use in the methods disclose herein comprise one or more pharmaceutically acceptable carriers, such as those widely employed in the art of drug manufacturing, and particularly antibody drug manufacturing. Pharmaceutically acceptable carriers in particular are non-toxic and should not interfere with the efficacy of the active ingredient. The carrier may be a diluent, adjuvant, excipient, or vehicle with which the antibodies are administered. Such vehicles may be liquids, such as aqueous fluids, oils, and emulsions. For example, 0.4% saline and 0.3% glycine may be used. The solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies in such pharmaceutical formulation may vary and will be selected primarily based on required dose, fluid volumes, viscosities, etc., according to the particular mode of administration selected, and other concerns, such as protein aggregation.

Examples of pharmaceutically acceptable carriers are solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, permeation enhancers, or combinations thereof.

Examples of buffers that may be used are acetic acid, citric acid, formic acid, succinic acid, phosphoric acid, carbonic acid, malic acid, aspartic acid, histidine, boric acid, Tris buffers, HEPPSO and HEPES.

Examples of antioxidants that may be used are ascorbic acid, methionine, cysteine hydrochloride, sodium bisulfate, sodium metabi sulfite, sodium sulfite, lecithin, citric acid, ethylenediamine tetraacetic acid (EDTA), sorbitol and tartaric acid.

Examples of amino acids that may be used are histidine, isoleucine, methionine, glycine, arginine, lysine, L-leucine, tri-leucine, alanine, glutamic acid, L- threonine, and 2-phenylamine.

Examples of surfactants that may be used are polysorbates (e.g., polysorbate-20 or polysorbate-80); polyoxamers (e.g, poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g, lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N. J.), polyethyl glycol, polypropyl glycol, and copolymers of ethylene and propylene glycol (e.g., PLURONICS™, PF68, etc.).

Examples of preservatives that may be used are phenol, m-cresol, p-cresol, o-cresol, chlorocresol, benzyl alcohol, phenylmercuric nitrite, phenoxyethanol, formaldehyde, chlorobutanol, magnesium chloride, alkylparaben (methyl, ethyl, propyl, butyl and the like), benzalkonium chloride, benzethonium chloride, sodium dehydroacetate and thimerosal, or mixtures thereof.

Examples of saccharides that may be used are monosaccharides, disaccharides, trisaccharides, polysaccharides, sugar alcohols, reducing sugars, nonreducing sugars such as glucose, sucrose, trehalose, lactose, fructose, maltose, dextran, glycerin, dextran, erythritol, glycerol, arabitol, sylitol, sorbitol, mannitol, mellibiose, melezitose, raffmose, mannotriose, stachyose, maltose, lactulose, maltulose, glucitol, maltitol, lactitol or iso-maltulose.

Examples of permeation enhancers that may be used include recombinant hyaluronidase or soluble fragment thereof such as rHuPH20 (Halozyme). Liquid formulations for subcutaneous administration may comprise rHuPH20 or another soluble human hyaluronidase enzyme. rHuPH20 may be present in an amount sufficient to result in an increase in the dispersion of the antibodies contained in the same liquid formulation during subcutaneous administration.

The amounts of pharmaceutically acceptable carrier(s) in the pharmaceutical compositions may be determined experimentally based on the activities of the carrier(s) and the desired characteristics of the formulation, such as stability, bioavailability, and/or minimal oxidation.

The methods of the present disclosure can use an antibody, or an antigen binding fragment thereof, as described above, alone or in combination with other pharmaceutically active compounds, to treat conditions such as those disclosed hereinabove. The additional pharmaceutically active compound(s) can be administered simultaneously (either in the same dosage form or in separate dosage forms) or sequentially. Accordingly, in one embodiment, the present disclosure comprises methods for treating a condition by administering to the subject a therapeutically-effective amount of an antibody, or an antigen binding fragment thereof, of the present disclosure and one or more additional pharmaceutically active compounds.

In some embodiments, the antibody, or an antigen binding fragment thereof, of the present disclosure is used in combination with existing therapies, including, but not limited to, corticosteroids; rituximab and other anti-CD20 antibodies; tocilizumab and other anti-IL-6 antibodies; or selenium, infliximab and other anti-TNF-alpha antibodies. In some embodiments, the antibody, or an antigen binding fragment thereof, of the present disclosure is used in combination with TSHR inhibitors.

EXAMPLES

Exemplary embodiments are provided in the following Examples 1-X. The following examples are presented only by way of illustration and to assist one of ordinary skill in using the invention. The examples are not intended in any way to otherwise limit the scope of the invention. In some embodiments, said IGF-1R inhibitor is an antibody or a subset of antibodies chosen from amongst the Examples below. In some embodiments, said IGF-1R inhibitor is a small molecule or a subset of small molecules chosen from amongst the Examples below.

Example A

Teprotumumab

Provided first is teprotumumab (TEPEZZA), an IGF-1R inhibitor approved for the treatment of TED. Teprotumumab and other related IGF-1R inhibitor antibodies and their methods of preparation can be found in U.S. Pat. No. 7,572,897, US20190225696, and US20190270820, which are hereby incorporated by reference in their entireties. In certain embodiments, teprotumumab may be used as an active control in clinical trials of other IGF-1R inhibitors, e.g. as in Example 31.

TABLE A

Teprotumumab Sequences and SEQ ID Numbers

| SEQ ID NO | Description | Sequence |
|---|---|---|
| | Antibody 1 (teprotumumab) | |
| 84 | CDRH1 aa | Ser Tyr Gly Met His |
| 85 | CDRH2 aa | Ile Ile Trp Phe Asp Gly Ser Ser Thr Tyr Tyr Ala Asp Ser Val Arg Gly |
| 86 | CDRH3 aa | Glu Leu Gly Arg Arg Tyr Phe Asp Leu |
| 87 | CDRL1 aa | Arg Ala Ser Gln Ser Val Ser Ser Tyr Leu Ala |
| 88 | CDRL2 aa | Asp Ala Ser Lys Arg Ala Thr |
| 89 | CDRL3 aa | Gln Gln Arg Ser Lys Trp Pro Pro Trp Thr |
| 90 | VH aa | Gln Val Glu Leu Val Glu Ser Gly Gly Gly Val Val Gln Pro Gly Arg Ser Gln Arg Leu Ser Cys Ala Ala Ser Gly Phe Thr Phe Ser Ser Tyr Gly Met His Trp Val Arg Gln Ala Pro Gly Lys Gly Leu Glu Trp Val Ala Ile Ile Trp Phe Asp Gly Ser Ser Thr Tyr Tyr Ala Asp Ser Val Arg Gly Arg Phe Thr Ile Ser Arg Asp Asn Ser Lys Asn Thr Leu Tyr Leu Gln Met Asn Ser Leu Arg Ala Glu Asp Thr Ala Val Tyr Phe Cys Ala Arg Glu Leu Gly Arg Arg Tyr Phe Asp Leu Trp Gly Arg Gly Thr Leu Val Ser Val Ser Ser |
| 91 | VL aa | Glu Ile Val Leu Thr Gln Ser Pro Ala Thr Leu Ser Leu Ser Pro Gly Glu Arg Ala Thr Leu Ser Cys Arg Ala Ser Gln Ser Val Ser Ser Tyr Leu Ala Trp Tyr Gln Gln Lys Pro Gly Gln Ala Pro Arg Leu Leu Ile Tyr Asp Ala Ser Lys Arg Ala Thr Gly Ile Pro Ala Arg Phe Ser Gly Ser Gly Ser Gly Thr Asp Phe Thr Leu Thr Ile Ser Ser Leu Glu Pro Glu Asp Phe Ala Val Tyr Tyr Cys Gln Gln Arg Ser Lys Trp Pro Pro Trp Thr Phe Gly Gln Gly Thr Lys Val Glu Ser Lys |
| | Antibody 2 | |
| 84 | CDRH1 aa | Ser Tyr Gly Met His |
| 92 | CDRH2 aa | Ile Ile Trp Phe Asp Gly Ser Ser Lys Tyr Tyr Gly Asp Ser Val Lys Gly |
| 86 | CDRH3 aa | Glu Leu Gly Arg Arg Tyr Phe Asp Leu |
| 87 | CDRL1 aa | Arg Ala Ser Gln Ser Val Ser Ser Tyr Leu Ala |
| 93 | CDRL2 aa | Asp Ala Ser Asn Arg Ala Thr |
| 89 | CDRL3 aa | Gln Gln Arg Ser Lys Trp Pro Pro Trp Thr |
| 94 | VH aa | Gln Val Gln Leu Val Glu Ser Gly Gly Gly Val Val Gln Pro Gly Arg Ser Leu Arg Leu Ser Cys Ala Ala Ser Gly Phe Thr Phe Ser Ser Tyr Gly Met His Trp Val Arg Gln Ala Pro Gly Lys Gly Leu Glu Trp Met Ala Ile Ile Trp Phe Asp Gly Ser Ser Lys Tyr Tyr Gly Asp Ser Val Lys Gly Arg Phe Thr Ile Ser Arg Asp Asn Ser Lys Asn Thr Leu Tyr Leu Gln Met Asn Ser Leu Arg Ala Asp Asp Thr Ala Val Tyr Tyr Cys Ala Arg Glu Leu Gly Arg Arg Tyr Phe Asp Leu Trp Gly Arg Gly Thr Leu Val Thr Val Ser Ser |
| 95 | VL aa | Glu Ile Val Leu Thr Gln Ser Pro Ala Thr Leu Ser Leu Ser Pro Gly Glu Arg Ala Thr Leu Ser Cys Arg Ala Ser Gln Ser Val Ser Ser Tyr Leu Ala Trp Tyr Gln Gln Lys Pro Gly Gln Ala Pro Arg Leu Leu Ile Tyr Asp Ala Ser Asn Arg Ala Thr Gly Ile Pro Ala Arg Phe Ser Gly Ser Gly Ser Gly Thr Asp Phe Thr Leu Thr Ile Ser Ser Leu Glu Pro Glu Asp Phe Ala Val Tyr Tyr Cys Gln Gln Arg Ser Lys Trp Pro Pro Trp Thr Phe Gly Gln Gly Thr Lys Val Glu Ile Lys |

Example 1

Dalotuzumab

Dalotuzumab and other related IGF-1R inhibitor antibodies and their methods of preparation can be found in WO 2005/058967, which is hereby incorporated by reference in its entirety.

| Heavy Chain CDRs - Dalotuzumab | | |
|---|---|---|
| HCDR1 | HCDR2 | HCDR3 |
| GGYLWN (SEQ ID NO: 1) | YISYDGTNNYKPSLKD (SEQ ID NO: 2) | YGRVFFDY (SEQ ID NO: 3) |

| Light Chain CDRs - Dalotuzumab | | |
|---|---|---|
| LCDR1 | LCDR2 | LCDR3 |
| RSSQSIVHSNGNTYLQ (SEQ ID NO: 4) | KVSNRLY (SEQ ID NO: 5) | FQGSHVPWT (SEQ ID NO: 6) |

| | |
|---|---|
| Heavy Chain (HC) | QVQLQESGPGLVKPSETLSLTCTVSGYSITGGYLWNWIRQPPGKGLE WIGYISYDGTNNYKPSLKDRVTISRDTSKNQFSLKLSSVTAADTAVYY CARYGRVFFDYWGQGTLVTVSSASTKGPSVFPLAPSSKSTSGGTAAL GCLVKDYFPEPVTVSWNSGALTSGVHTFPAVLQSSGLYSLSSVVTVPS SSLGTQTYICNVNHKPSNTKVDKRVEPKSCDKTHTCPPCPAPELLGGP SVFLFPPKPKDTLMISRTPEVTCVVVDVSHEDPEVKFNWYVDGVEVH NAKTKPREEQYNSTYRVVSVLTVLHQDWLNGKEYKCKVSNKALPAP IEKTISKAKGQPREPQVYTLPPSREEMTKNQVSLTCLVKGFYPSDIAVE WESNGQPENNYKTTPPVLDSDGSFFLYSKLTVDKSRWQQGNVFSCSV MHEALHNHYTQKSLSLSPGK (SEQ ID NO: 7) |
| Light Chain (LC) | DIVMTQSPLSLPVTPGEPASISCRSSQSIVHSNGNTYLQWYLQKPGQSP QLLIYKVSNRLYGVPDRFSGSGSGTDFTLKISRVEAEDVGVYYCFQGS HVPWTFGQGTKVEIKRTVAAPSVFIFPPSDEQLKSGTASVVCLLNNFY PREAKVQWKVDNALQSGNSQESVTEQDSKDSTYSLSSTLTLSKADYE KHKVYACE VTHQGLSSPVTKSFNRGEC (SEQ ID NO: 8) |

Some embodiments of the disclosure are anti-IGF-1R inhibitor mAbs or antigen binding fragments thereof, comprising a heavy chain comprising a variable heavy chain CDR1, a variable heavy chain CDR2, and a variable heavy chain CDR3, wherein the variable heavy chain CDR1 comprises an amino acid sequence SEQ ID NO:1, the variable heavy chain CDR2 comprises an amino acid sequence SEQ ID NO:2; and the variable heavy chain CDR3 comprises an amino acid sequence SEQ ID NO:3 or at least a CDR with at least 80% f sequence identity after optimal alignment with SEQ ID NO:1, SEQ ID NO:2, and SEQ ID NO:3.

The anti-IGF-1R inhibitor mAbs or antibody or antigen binding fragment thereof may additionally comprise a light chain which is paired with the heavy chain to form an antigen binding domain. In some embodiments, the light chain comprises a variable light chain CDR1, a variable light chain CDR2, and a variable light chain CDR3, wherein the variable light chain CDR1 comprises an amino acid sequence SEQ ID NO:4, the variable light chain CDR2 comprises an amino acid sequence SEQ ID NO:5; and the variable light chain CDR3 comprises an amino acid sequence SEQ ID NO:6 or at least a CDR with at least 80% f homology after optimal alignment with SEQ ID NO:4, SEQ ID NO:5, and SEQ ID NO:6.

In some embodiments, the anti-IGF-1R inhibitor mAbs or antigen binding fragment thereof comprises a heavy chain amino acid sequence of SEQ ID NO:7 or at least a heavy chain with at least 85%, 90%, 95%, 97%, 98%, or 99% f sequence identity after optimal alignment with SEQ ID NO:7. Alternatively, or in addition, the anti-IGF-1R inhibitor mAbs or antigen binding fragment thereof may comprise a light chain having an amino acid sequence of SEQ ID NO:8 or at least a heavy chain with at least 85%, 90%, 95%, 97%, 98%, or 99% f sequence identity after optimal alignment with SEQ ID NO:8.

Example 2

Ganitumab

Ganitumab and other related IGF-1R inhibitor antibodies and their methods of preparation can be found in WO 2006/069202, which is hereby incorporated by reference in its entirety.

| Heavy Chain CDRs - Ganitumab | | |
|---|---|---|
| HCDR1 | HCDR2 | HCDR3 |
| SSNWWS (SEQ ID NO: 9) | EIYHSGSTNYNPSLKS (SEQ ID NO: 10) | WTGRTDAFDI (SEQ ID NO: 11) |
| **Light Chain CDRs - Ganitumab** | | |
| LCDR1 | LCDR2 | LCDR3 |
| ISCRSSQSLLHSNGYNYLD (SEQ ID NO: 12) | LGSNRAS (SEQ ID NO: 13) | MQGTHWPLT (SEQ ID NO: 14) |
| Heavy Chain (HC) | QVQLQESGPGLVKPSGTLSLTCAVSGGSISSSNWWSWVRQPPGKGLE WIGEIYHSGSTNYNPSLKSRVTSVDKSKNQFSLKLSSVTAAD TAVYYCARWTGRTDAFDIWGQGTMVTVSSASTKGPSVFPL APSSKSTSGGTAALGCLVKDYFPEPVTVSWNSGALTSGVH TFPAVLQSSGLYSLSSVVTVPSSSLGTQTYICNVNHKPSN TKVDKKVEPKSCDKTHTCPPCPAPELLGGPSVFLFPPKPK DTLMISRTPE VTCVVVDVSH EDPEVKFNWYVDGVEVHNAK TKPREEQYNSTYRVVSVLTVLHQDWLNGKEYKCKVSNKAL PAPIEKTISKAKGQPREPQVYTLPPSRDELTKNQVSLTCL VKGFYPSDIAVEWESNGQPENNYKTTPPVLDSDGSFFLYS KLTVDKSRWQQGNVFSCSVM HEALHNHYTQ KSLSLSPGK (SEQ ID NO: 15) | |
| Light Chain (LC) | DVVMTQSPLS LPVTPGEPASISCRSSQSLLHSNGYNYLDW YLQKPGQSPQLLIYLGSNRASGVPDRFSGSGSGTDFTLKI SRVEAEDVGVYYCMQGTHWPLTFGQGTKVE IKRTVAAPSV FIFPPSDEQL KSGTASVVCL LNNFYPREAKVQWKVDNALQ SGNSQESVTE QDSKDSTYSLSSTLTLSKADYEKHKVYACE VTHQGLSSPVTKSFNRGEC (SEQ ID NO: 16) | |

Some embodiments of the disclosure are anti-IGF-1R inhibitor mAbs or antigen binding fragments thereof, comprising a heavy chain comprising a variable heavy chain CDR1, a variable heavy chain CDR2, and a variable heavy chain CDR3, wherein the variable heavy chain CDR1 comprises an amino acid sequence SEQ ID NO:9, the variable heavy chain CDR2 comprises an amino acid sequence SEQ TD NO: 10; and the variable heavy chain CDR3 comprises an amino acid sequence SEQ ID NO:11 or at least a CDR with at least 80% f sequence identity after optimal alignment with SEQ ID NO:9, SEQ ID NO:10, and SEQ ID NO:11.

The anti-IGF-1R inhibitor mAbs or antibody or antigen binding fragment thereof may additionally comprise a light chain which is paired with the heavy chain to form an antigen binding domain. In some embodiments, the light chain comprises a variable light chain CDR1, a variable light chain CDR2, and a variable light chain CDR3, wherein the variable light chain CDR1 comprises an amino acid sequence SEQ ID NO:12, the variable light chain CDR2 comprises an amino acid sequence SEQ ID NO:13; and the variable light chain CDR3 comprises an amino acid sequence SEQ ID NO:14 or at least a CDR with at least 80% f homology after optimal alignment with SEQ ID NO:12, SEQ ID NO:13, and SEQ ID NO:14.

In some embodiments, the anti-IGF-1R inhibitor mAbs or antigen binding fragment thereof comprises a heavy chain amino acid sequence of SEQ ID NO:15 or at least a heavy chain with at least 85%, 90%, 95%, 97%, 98%, or 99% f sequence identity after optimal alignment with SEQ ID NO:15. Alternatively, or in addition, the anti-IGF-1R inhibitor mAbs or antigen binding fragment thereof may comprise a light chain having an amino acid sequence of SEQ ID NO:16 or at least a heavy chain with at least 85%, 90%, 95%, 97%, 98%, or 99% f sequence identity after optimal alignment with SEQ ID NO:16.

Example 3

Xentuzumab

Xentuzumab and other related IGF-1R inhibitor antibodies and their methods of preparation can be found in WO 2014/135611, which is hereby incorporated by reference in its entirety.

| Heavy Chain CDRs - Xentuzumab | | |
|---|---|---|
| HCDR1 | HCDR2 | HCDR3 |
| SYWMS (SEQ ID NO: 17) | SITSYGSFTYADSVK (SEQ ID NO: 18) | NMYTHFDS (SEQ ID NO: 19) |
| **Light Chain CDRs - Xentuzumab** | | |
| LCDR1 | LCDR2 | LCDR3 |
| SGSSSNIGSNSVS (SEQ ID NO: 20) QSRDTYGYYWV | DNSKRPS (SEQ ID NO: 21) | QSRDTYGYYWV (SEQ ID NO: 22) |
| Heavy Chain (HC) | QVELVESGGGLVQPGGSLRLSCAASGFTFTSYWMSWVRQA PGKGLELVSSITSYGSFTYYADSVKGRFTISRDNSKNTLY | |

-continued

| | |
|---|---|
| | LQMNSLRAEDTAVYYCARNMYTHFDSWGQGTLVTVSSAST KGPSVFPLAPSSKSTSGGTAALGCLVKDYFPEPVTVSWNS GALTSGVHTF PAVLQSSGLYSLSSVVTVPS SSLGTQTYIC NVNHKPSNTKVDKKVEPKSCDKTHTCPPCPAPELLGGPSV FLFPPKPKDTLMISRTPEVTCVVVDVSHEDPEVKFNWYVD GVEVHNAKTK PREEQYNSTYRVVSVLTVLHQDWLNGKEYK CKVSNKALPAPIEKTISKAKGQPREPQVYTLPPSRDELTK NQVSLTCLVK GFYPSDIAVEWESNGQPENNYKTTPPVLDS (SEQ ID NO: 23) |
| Light Chain (LC) | DIVLTQPPSVSGAPGQRVTISCSGSSSNIGSNSVSWYQQL PGTAPKLLIYDNSKRPSGVPDRFSGSKSGTSASLAITGLQ SEDEADYYCQSRDTYGYYWVFGGGTKLTVLGQPKAAPSVT LFPPSSEELQANKATLVCLI SDFYPGAVTVAWKGDSSPVK AGVETTTPSKQSNNKYAASSYLSLTPEQWKSHRSYSCQVT HEGSTVEKTVAPTECS (SEQ ID NO: 24) |

Some embodiments of the disclosure are anti-IGF-1R inhibitor mAbs or antigen binding fragments thereof, comprising a heavy chain comprising a variable heavy chain CDR1, a variable heavy chain CDR2, and a variable heavy chain CDR3, wherein the variable heavy chain CDR1 comprises an amino acid sequence SEQ ID NO:17, the variable heavy chain CDR2 comprises an amino acid sequence SEQ ID NO:18; and the variable heavy chain CDR3 comprises an amino acid sequence SEQ ID NO:19 or at least a CDR with at least 80% f sequence identity after optimal alignment with SEQ ID NO:17, SEQ ID NO:18, and SEQ ID NO:19.

The anti-IGF-1R inhibitor mAbs or antibody or antigen binding fragment thereof may additionally comprise a light chain which is paired with the heavy chain to form an antigen binding domain. In some embodiments, the light chain comprises a variable light chain CDR1, a variable light chain CDR2, and a variable light chain CDR3, wherein the variable light chain CDR1 comprises an amino acid sequence SEQ ID NO:20, the variable light chain CDR2 comprises an amino acid sequence SEQ ID NO:21; and the variable light chain CDR3 comprises an amino acid sequence SEQ ID NO:22 or at least a CDR with at least 80% f homology after optimal alignment with SEQ ID NO:20, SEQ ID NO:21, and SEQ ID NO:22.

In some embodiments, the anti-IGF-1R inhibitor mAbs or antigen binding fragment thereof comprises a heavy chain amino acid sequence of SEQ ID NO:23 or at least a heavy chain with at least 85%, 90%, 9500 9700 98%, or 9900 of sequence identity after optimal alignment with SEQ ID NO:23. Alternatively, or in addition, the anti-IGF-1R inhibitor mAbs or antigen binding fragment thereof may comprise a light chain having an amino acid sequence of SEQ TD NO:24 or at least a heavy chain with at least 850, 900, 950, 970, 98Q, or 99 of sequence identity after optimal alignment with SEQ ID NO:24.

Example 4

AVE1642

AVE1642 and other related IGF-1R inhibitor antibodies and their methods of preparation can be found in WO 2003/106621, which is hereby incorporated by reference in its entirety.

Heavy Chain CDRs - AVE1642

| HCDR1 | HCDR2 | HCDR3 |
|---|---|---|
| SYWMH (SEQ ID NO: 25) | EINPSNGRTNYNEKFKR (SEQ ID NO: 26) | GRPDYYGSSKWYFDV (SEQ ID NO: 27) |
| GYTFTSYWMH (SEQ ID NO: 75) | EINPSNGRTN (SEQ ID NO: 76) | GRPDYYGSSKWYFDV (SEQ ID NO: 27) |
| SYWMH (SEQ ID NO: 25) | EINPSNGRTN (SEQ ID NO: 76) | GRPDYYGSSKWYFDV (SEQ ID NO: 27) |
| SYWMH (SEQ ID NO: 25) | EINPSNGRTNYNQKFQG (SEQ ID NO: 77) | GRPDYYGSSKWYFDV (SEQ ID NO: 27) |
| GYTFTSYWMH (SEQ ID NO: 75) | EINPSNGRTNYNQKFQG (SEQ ID NO: 77) | GRPDYYGSSKWYFDV (SEQ ID NO: 27) |

Light Chain CDRs - AVE1642

| LCDR1 | LCDR2 | LCDR3 |
|---|---|---|
| RSSQSIVHSNVNTYLE (SEQ ID NO: 28) | KVSNRFS (SEQ ID NO: 29) | FQGSHVPPT (SEQ ID NO: 30) |

Variable Domains - AVE1642

| | |
|---|---|
| Heavy Chain (VH1) | QVQLQQSGAELVKPGASVKLSCKASGYTFTSYWMHWVKQRPGQGL EWIGEINPSNGRTNYNEKFKRKATLTVDKSSSTAYMQLSSLTSEDSAV YYFARGRPDYYGSSKWYFDVWGAGTTVTVSS (SEQ ID NO: 31) |

-continued

| | |
|---|---|
| Heavy Chain (VH2) | QVQLVQSGAEVVKPGASVKLSCKASGYTFTSYWMHWVKQRPGQGL EWIGEINPSNGRTNYNQKFQGKATLTVDKSSSTAYMQLSSLTSEDSAV YYFARGRPDYYGSSKWYFDVWGQGTTVTVSS (SEQ ID NO: 78) |
| Heavy Chain (VH3) | QVQLVQSGAEVVKPGASVKLSCKASGYTFTSYWMHWVKQRPGQGL EWIGEINPSNGRTNYNQKFQGKATLTVDKSSSTAYMQLSSLTSEDSAV YYFARGRPDYYGSSKWYFDVWGQGTTVTVS (SEQ ID NO: 79) |
| Light Chain (VL1) | DVLMTQTPLSLPVSLGDQASISCRSSQSIVHSNVNTYLEWYLQKPGQS PKLLIYKVSNRFSGVPDRFSGSGSGTDFTLRISRVEAEDLGIYYCFQGS HVPPTFGGGTKLEIKR (SEQ ID NO: 32) |
| Light Chain (VL2) | DVVMTQTPLSLPVSLGDPASISCRSSQSIVHSNVNTYLEWYLQKPGQS PRLLIYKVSNRFSGVPDRFSGSGAGTDFTLRISRVEAEDLGIYYCFQGS HVPPTFGGGTKLEIKR (SEQ ID NO: 80) |
| Light Chain (VL3) | DVLMTQTPLSLPVSLGDPASISCRSSQSIVHSNVNTYLEWYLQKPGQS PKLLIYKVSNRFSGVPDRFSGSGAGTDFTLRISRVEAEDLGIYYCFQGS HVPPTFGGGTKLEIKR (SEQ ID NO: 81) |
| Light Chain (VL4) | DVLMTQTPLSLPVSLGDPASISCRSSQSIVHSNVNTYLEWYLQKPGQS PRLLIYKVSNRFSGVPDRFSGSGAGTDFTLRISRVEAEDLGIYYCFQGS HVPPTFGGGTKLEIKR (SEQ ID NO: 82) |
| Light Chain (VL5) | DVVMTQTPLSLPVSLGDPASISCRSSQSIVHSNVNTYLEWYLQKPGQS PKLLIYKVSNRFSGVPDRFSGSGAGTDFTLRISRVEAEDLGIYYCFQGS HVPPTFGGGTKLEIKR (SEQ ID NO: 83) |

Some embodiments of the disclosure are anti-IGF-1R inhibitor mAbs or antigen binding fragments thereof, comprising a heavy chain comprising a variable heavy chain CDR1, a variable heavy chain CDR2, and a variable heavy chain CDR3, wherein the variable heavy chain CDR1 comprises an amino acid sequence SEQ ID NO:25, the variable heavy chain CDR2 comprises an amino acid sequence SEQ ID NO:26; and the variable heavy chain CDR3 comprises an amino acid sequence SEQ ID NO:27 or at least a CDR with at least 80% f sequence identity after optimal alignment with SEQ ID NO:25, SEQ ID NO:26, and SEQ ID NO:27.

The anti-IGF-1R inhibitor mAbs or antibody or antigen binding fragment thereof may additionally comprise a light chain which is paired with the heavy chain to form an antigen binding domain. In some embodiments, the light chain comprises a variable light chain CDR1, a variable light chain CDR2, and a variable light chain CDR3, wherein the variable light chain CDR1 comprises an amino acid sequence SEQ ID NO:28, the variable light chain CDR2 comprises an amino acid sequence SEQ ID NO:29; and the variable light chain CDR3 comprises an amino acid sequence SEQ ID NO:30 or at least a CDR with at least 80% f homology after optimal alignment with SEQ ID NO:28, SEQ ID NO:29, and SEQ ID NO:30.

In some embodiments, the anti-IGF-1R inhibitor mAbs or antigen binding fragment thereof comprises a heavy chain amino acid sequence of SEQ ID NO:31 or at least a heavy chain with at least 85%, 90%, 95%, 97%, 98%, or 99% f sequence identity after optimal alignment with SEQ ID NOs:31, 78, or 79. Alternatively, or in addition, the anti-IGF-1R inhibitor mAbs or antigen binding fragment thereof may comprise a light chain having an amino acid sequence of SEQ ID NO:32 or at least a heavy chain with at least 85%, 90%, 95%, 97%, 98%, or 99% f sequence identity after optimal alignment with SEQ ID NOs:32, 80, 81, 82, or 83.

Example 5

Figitumumab

Figitumumab and other related IGF-1R inhibitor antibodies and their methods of preparation can be found in U.S. Pat. No. 7,037,498 which is hereby incorporated by reference in its entirety.

| Heavy Chain CDRs - Figitumumab | | |
|---|---|---|
| HCDR1 | HCDR2 | HCDR3 |
| GFTFSSYAMN (SEQ ID NO: 33) | AISGSGGTTFYADSVKG (SEQ ID NO: 34) | DLGWSDSYYYYYGMDV (SEQ ID NO: 35) |
| **Light Chain CDRs - Figitumumab** | | |
| LCDR1 | LCDR2 | LCDR3 |
| RASQGIRNDLG (SEQ ID NO: 36) | AASRLHR (SEQ ID NO: 37) | LQHNSYPCS (SEQ ID NO: 38) |
| Heavy Chain (HC) | EVQLLESGGGLVQPGGSLRLSCTASGFTFSSYAMNWVRQA PGKGLEWVSAISGSGGTTFYADSVKGRFTISRDNSRTTLY LQMNSLRAEDTAVYYCAKDLGWSDSYYYYYGMDVWGQGTT VTVSSASTKGPSVFPLAPCS RSTSESTAALGCLVKDYFPE PVTVSWNSGALTSGVHTFPAVLQSSGLYSLSSVVTVPSSN FGTQTYTCNVDHKPSNTKVD KTVERKCCVECPPCPAPPVA | |

-continued

| | |
|---|---|
| | GPSVFLFPPKPKDTLMISRTPEVTCVVVDVSHEDPEVQFN<br>WYVDGVEVHNAKTKPREEQFNSTFRVVSVLTVVHQDWLNG<br>KEYKCKVSNKGLPAPIEKTI SKTKGQPREPQVYTLPPSRE<br>EMTKNQVSLTCLVKGFYPSDIAVEWESNGQPENNYKTTPP<br>MLDSDGSFFLYSKLTVDKSRWQQGNVFSCSVMHEALHNHY<br>TQKSLSLSPGK (SEQ ID NO: 39) |
| Light Chain (LC) | DIQMTQFPSSLSASVGDRVTITCRASQGIRNDLGWYQQKPGKAPKRLI<br>YAASRLHRGVPSRFSGSGSGTEFTLTISSLQPEDFATYYCLQHNSYPCS<br>FGQGTKLEIKRTVAAPSVFIFPPSDEQLKSGTASVVCLLNNFYPREAKV<br>QWKVDNALQSGNSQESVTEQDSKDSTYSLSSTLTLSKADYEKHKVY<br>ACEVTHQGLSSPVTKSFNRGEC (SEQ ID NO: 40) |

Some embodiments of the disclosure are anti-IGF-1R inhibitor mAbs or antigen binding fragments thereof, comprising a heavy chain comprising a variable heavy chain CDR1, a variable heavy chain CDR2, and a variable heavy chain CDR3, wherein the variable heavy chain CDR1 comprises an amino acid sequence SEQ ID NO:33, the variable heavy chain CDR2 comprises an amino acid sequence SEQ ID NO:34; and the variable heavy chain CDR3 comprises an amino acid sequence SEQ ID NO:35 or at least a CDR with at least 80% f sequence identity after optimal alignment with SEQ ID NO:33, SEQ ID NO:34, and SEQ ID NO:35.

The anti-IGF-1R inhibitor mAbs or antibody or antigen binding fragment thereof may additionally comprise a light chain which is paired with the heavy chain to form an antigen binding domain. In some embodiments, the light chain comprises a variable light chain CDR1, a variable light chain CDR2, and a variable light chain CDR3, wherein the variable light chain CDR1 comprises an amino acid sequence SEQ ID NO:36, the variable light chain CDR2 comprises an amino acid sequence SEQ ID NO:37; and the variable light chain CDR3 comprises an amino acid sequence SEQ ID NO:38 or at least a CDR with at least 80% f homology after optimal alignment with SEQ ID NO:36, SEQ ID NO:37, and SEQ ID NO:38.

In some embodiments, the anti-IGF-1R inhibitor mAbs or antigen binding fragment thereof comprises a heavy chain amino acid sequence of SEQ ID NO:39 or at least a heavy chain with at least 85%, 90%, 9500 9700 98%, or 9900 of sequence identity after optimal alignment with SEQ ID NO:39. Alternatively, or in addition, the anti-IGF-1R inhibitor mAbs or antigen binding fragment thereof may comprise a light chain having an amino acid sequence of SEQ TD NO:40 or at least a heavy chain with at least 8500, 9000, 9500, 9700, 98%, or 990% f sequence identity after optimal alignment with SEQ TD NO:40.

Example 6

Dusigitumab

Dusigitumab (MEDI-573) and other related IGF-1R inhibitor antibodies and their methods of preparation can be found in U.S. Pat. No. 7,939,637 which is hereby incorporated by reference in its entirety.

| Heavy Chain CDRs - Dusigitumab | | |
|---|---|---|
| HCDR1 | HCDR2 | HCDR3 |
| SYDIN (SEQ ID NO: 41) | WMNPNSGNTGYAQKFQG (SEQ ID NO: 42) | DPYYYYYGMDV (SEQ ID NO: 43) |
| **Light Chain CDRs - Dusigitumab** | | |
| LCDR1 | LCDR2 | LCDR3 |
| SGSSSNIENNHVS (SEQ ID NO: 44) | DNNKRPS (SEQ ID NO: 45) | ETWDTSLSAGRV (SEQ ID NO: 46) |
| Heavy Chain (HC) | QVQLVQSGAEVKKPGASVKVSCKASGYTFTSYDINWVRQA<br>TGQGLEWMGWMNPNSGNTGYAQKFQGRVTMTRNTSISTAYMELSS<br>LRSEDTAVYYCARDPYYYYYGMDVWGQGTTVTVSSASTKGPSVFP<br>LAPCSRSTSESTAALGCLVKDYFPEPVTVSWNSGALTSGVHTFPAVLQ<br>SSGLYSLSSVVTVPSSNFGTQTYTCNVDHKPSNTKVDKTVER<br>KCCVECPPCPAPPVAGPSVFLFPPKPKDTLMISRTPEVTC<br>VVVDVSHEDPEVQFNWYVDGVEVHNAKTKPREEQFNSTFR<br>VVSVLTVVHQDWLNGKEYKCKVSNKGLPAPIEKTISKTKG<br>QPREPQVYTLPPSREEMTKNQVSLTCLVKGFYPSDIAVEW<br>ESNGQPENNYKTTPPMLDSDGSFFLYSKLTVDKSRWQQGN<br>VFSCSVMHEALHNHYTQKSLSLSPGK (SEQ ID NO: 47) | |
| Light Chain (LC) | QSVLTQPPSVSAAPGQKVTISCSGSSSNIENNHVSWYQQL<br>PGTAPKLLIYDNNKRPSGIPDRFSGSKSGTSATLGITGLQTGDEADYYC<br>ETWDTSLSAGRVFGGGTKLTVLGQPKAAPSVTLFPPSSEEL<br>QANKATLVCLISDFYPGAVTVAWKADSSPVKAGVETTTPS<br>KQSNNKYAASSYLSLTPEQWKSHRSYSCQVTHEGSTVEKTVAPTECS<br>(SEQ ID NO: 48) | |

Some embodiments of the disclosure are anti-IGF-1R inhibitor mAbs or antigen binding fragments thereof, comprising a heavy chain comprising a variable heavy chain CDR1, a variable heavy chain CDR2, and a variable heavy chain CDR3, wherein the variable heavy chain CDR1 comprises an amino acid sequence SEQ ID NO:41, the variable heavy chain CDR2 comprises an amino acid sequence SEQ ID NO:42; and the variable heavy chain CDR3 comprises an amino acid sequence SEQ ID NO:43 or at least a CDR with at least 80% f sequence identity after optimal alignment with SEQ ID NO:41, SEQ ID NO:42, and SEQ ID NO:43.

The anti-IGF-1R inhibitor mAbs or antibody or antigen binding fragment thereof may additionally comprise a light chain which is paired with the heavy chain to form an antigen binding domain. In some embodiments, the light chain comprises a variable light chain CDR1, a variable light chain CDR2, and a variable light chain CDR3, wherein the variable light chain CDR1 comprises an amino acid sequence SEQ ID NO:44, the variable light chain CDR2 comprises an amino acid sequence SEQ ID NO:45; and the variable light chain CDR3 comprises an amino acid sequence SEQ ID NO:46 or at least a CDR with at least 80% f homology after optimal alignment with SEQ ID NO:44, SEQ ID NO:45, and SEQ ID NO:46.

In some embodiments, the anti-IGF-1R inhibitor mAbs or antigen binding fragment thereof comprises a heavy chain amino acid sequence of SEQ ID NO:39 or at least a heavy chain with at least 85%, 90%, 95%, 97%, 98%, or 99% f sequence identity after optimal alignment with SEQ ID NO:47. Alternatively, or in addition, the anti-IGF-1R inhibitor mAbs or antigen binding fragment thereof may comprise a light chain having an amino acid sequence of SEQ ID NO:40 or at least a heavy chain with at least 85%, 90%, 95%, 97%, 98%, or 99% f sequence identity after optimal alignment with SEQ ID NO:48.

Example 7

Cixutumumab

Cixutumumab and other related IGF-1R inhibitor antibodies and their methods of preparation can be found in U.S. Pat. No. 7,638,605 which is hereby incorporated by reference in its entirety.

| Heavy Chain CDRs - Cixutumumab | | |
|---|---|---|
| HCDR1 | HCDR2 | HCDR3 |
| SYAIS (SEQ ID NO: 49) | GIIPIFGTANYAQKFQ (SEQ ID NO: 50) | APLRFLEWSTQDHYYYYYMDV (SEQ ID NO: 51) |
| **Light Chain CDRs - Cixutumumab** | | |
| LCDR1 | LCDR2 | LCDR3 |
| QGDSLRSYYAT (SEQ ID NO: 52) | GENKRPS (SEQ ID NO: 53) | KSRDGSGQHLV (SEQ ID NO: 54) |
| Heavy Chain (HC) | EVQLVQSGAEVKKPGSSVKVSCKASGGTFSSYAISWVRQA PGQGLEWMGGIIPIFGTANYAQKFQGRVTITADKSTSTAY MELSSLRSEDTAVYYCARAPLRFLEWSTQDHYYYYYMDVW GKGTTVTVSSASTKGPSVFPLAPSSKSTSGGTAALGCLVK DYFPEPVTVSWNSGALTSGVHTFPAVLQSSGLYSLSSVVT VPSSSLGTQTYICNVNHKPSNTKVDKKVEPKSCDKTHTCP PCPAPELLGGPSVFLFPPKP KDTLMISRTPEVTCVVVDVS HEDPEVKFNWYVDGVEVHNAKTKPREEQYNSTYRVVSVLT VLHQDWLNGKEYKCKVSNKALPAPIEKTISKAKGQPREPQ VYTLPPSREEMTKNQVSLTCLVKGFYPSDIAVEWESNGQP ENNYKTTPPVLDSDGSFFLYSKLTVDKSRWQQGNVFSCSV MHEALHNHYTQKSLSLSPGK (SEQ ID NO: 55) | |
| Light Chain (LC) | SSELTQDPAVSVALGQTVRITCQGDSLRSYYATWYQQKPG QAPILVIYGENKRPSGIPDRFSGSSSGNTASLTITGAQAE DEADYYCKSRDGSGQHLVFGGGTKLTVLGQ PKAAPSVTLF PPSSEELQANKATLVCLISDFYPGAVTVAWKADSSPVKAGVETTTPSK QSNNKYAASSYLSLTPEQWKSHRSYSCQVTHEGSTVEKTVAPAECS (SEQ ID NO: 56) | |

Some embodiments of the disclosure are anti-IGF-1R inhibitor mAbs or antigen binding fragments thereof, comprising a heavy chain comprising a variable heavy chain CDR1, a variable heavy chain CDR2, and a variable heavy chain CDR3, wherein the variable heavy chain CDR1 comprises an amino acid sequence SEQ ID NO:49, the variable heavy chain CDR2 comprises an amino acid sequence SEQ ID NO:50; and the variable heavy chain CDR3 comprises an amino acid sequence SEQ ID NO:51 or at least a CDR with at least 80% f sequence identity after optimal alignment with SEQ ID NO:49, SEQ ID NO:50, and SEQ ID NO:51.

The anti-IGF-1R inhibitor mAbs or antibody or antigen binding fragment thereof may additionally comprise a light chain which is paired with the heavy chain to form an antigen binding domain. In some embodiments, the light chain comprises a variable light chain CDR1, a variable light chain CDR2, and a variable light chain CDR3, wherein the variable light chain CDR1 comprises an amino acid sequence SEQ ID NO:52, the variable light chain CDR2 comprises an amino acid sequence SEQ ID NO:53; and the variable light chain CDR3 comprises an amino acid sequence SEQ ID NO:54 or at least a CDR with at least 80% f homology after optimal alignment with SEQ ID NO:52, SEQ ID NO:53, and SEQ ID NO:54.

In some embodiments, the anti-IGF-1R inhibitor mAbs or antigen binding fragment thereof comprises a heavy chain amino acid sequence of SEQ ID NO:55 or at least a heavy chain with at least 85%, 90%, 95%, 97%, 98%, or 99% f sequence identity after optimal alignment with SEQ ID NO:55. Alternatively, or in addition, the anti-IGF-1R inhibitor mAbs or antigen binding fragment thereof may comprise a light chain having an amino acid sequence of SEQ ID NO:56 or at least a heavy chain with at least 85%, 90%, 95%, 97%, 98%, or 99% f sequence identity after optimal alignment with SEQ ID NO:56.

Example 8

BIIB022

BIIB022 and other related IGF-1R inhibitor antibodies and their methods of preparation can be found in U.S. Pat. No. 7,612,178 which is hereby incorporated by reference in its entirety.

| Heavy Chain CDRs - BIIB022 | | |
|---|---|---|
| HCDR1 | HCDR2 | HCDR3 |
| IYRMQ<br>(SEQ ID NO: 57) | GISPSGGTTWYADSVKG<br>(SEQ ID NO: 58) | WSGGSGYAFDI (SEQ ID NO: 59) |
| **Light Chain CDRs - BIIB022** | | |
| LCDR1 | LCDR2 | LCDR3 |
| QASRDIRNYN<br>(SEQ ID NO: 60) | DASSLQT<br>(SEQ ID NO: 61) | QQFDSLPHT<br>(SEQ ID NO: 62) |
| Heavy Chain (HC) | EVQLLESGGGLVQPGGSLRLSCAASGFTFSIYRMQWVRQAPGKGLEW<br>VSGISPSGGTTWYADSVKGRFTISRDNSKNTLYLQMNSLRAEDTAVY<br>YCARWSGGSGYAFDIWGQGTMVTVSS (SEQ ID NO: 63) | |
| Light Chain (LC) | DIQMTQSPLSLSASVGDRVTITCQASRDIRNYLNWYQQKPGKAPKLLI<br>YDASSLQTGVPSRFGGSGSGTDFSFTIGSLQPEDIATYYCQQFDSLPHT<br>FGQGTKLEIK (SEQ ID NO: 64) | |

Some embodiments of the disclosure are anti-IGF-1R inhibitor mAbs or antigen binding fragments thereof, comprising a heavy chain comprising a variable heavy chain CDR1, a variable heavy chain CDR2, and a variable heavy chain CDR3, wherein the variable heavy chain CDR1 comprises an amino acid sequence SEQ ID NO:57, the variable heavy chain CDR2 comprises an amino acid sequence SEQ ID NO:58; and the variable heavy chain CDR3 comprises an amino acid sequence SEQ ID NO:59 or at least a CDR with at least 80% f sequence identity after optimal alignment with SEQ ID NO:57, SEQ ID NO:58, and SEQ ID NO:59.

The anti-IGF-1R inhibitor mAbs or antibody or antigen binding fragment thereof may additionally comprise a light chain which is paired with the heavy chain to form an antigen binding domain. In some embodiments, the light chain comprises a variable light chain CDR1, a variable light chain CDR2, and a variable light chain CDR3, wherein the variable light chain CDR1 comprises an amino acid sequence SEQ ID NO:60, the variable light chain CDR2 comprises an amino acid sequence SEQ ID NO:61; and the variable light chain CDR3 comprises an amino acid sequence SEQ ID NO:62 or at least a CDR with at least 80% f homology after optimal alignment with SEQ ID NO:60, SEQ ID NO:61, and SEQ ID NO:62.

In some embodiments, the anti-IGF-1R inhibitor mAbs or antigen binding fragment thereof comprises a heavy chain amino acid sequence of SEQ ID NO:63 or at least a heavy chain with at least 85%, 90%, 95%, 97%, 98%, or 99% f sequence identity after optimal alignment with SEQ ID NO:63. Alternatively, or in addition, the anti-IGF-1R inhibitor mAbs or antigen binding fragment thereof may comprise a light chain having an amino acid sequence of SEQ ID NO:64 or at least a heavy chain with at least 85%, 90%, 95%, 97%, 98%, or 99% f sequence identity after optimal alignment with SEQ ID NO:64.

Example 9

| Robatumumab<br>Heavy Chain (HC) and Light Chain (LC) for<br>Robatumumab | |
|---|---|
| Heavy Chain | EVQLVQSGGG LVKPGGSLRL SCAASGFTFS SFAMHWVRQA<br>PGKGLEWISV IDTRGATYYADSVKGRFTIS RDNAKNSLYL |

-continued

| Robatumumab<br>Heavy Chain (HC) and Light Chain (LC) for<br>Robatumumab | |
|---|---|
| (HC) | QMNSLRAEDT AVYYCARLGN FYYGMDVWGQ GTTVTVSSAS<br>TKGPSVFPLA PSSKSTSGGT AALGCLVKDY FPEPVTVSWN<br>SGALTSGVHT FPAVLQSSGLYSLSSVVTVP SSSLGTQTYI<br>CNVNHKPSNT KVDKKVEPKS CDKTHTCPPC PAPELLGGPS<br>VFLFPPKPKD TLMISRTPEV TCVVVDVSHE DPEVKFNWYV<br>DGVEVHNAKT KPREEQYNSTYRVVSVLTVL HQDWLNGKEY<br>KCKVSNKALP APIEKTISKA KGQPREPQVY TLPPSRDELT<br>KNQVSLTCLV KGFYPSDIAV EWESNGQPEN NYKTTPPVLD<br>SDGSFFLYSK LTVDKSRWQQGNVFSCSVMH EALHNHYTQK<br>SLSLSPGK (SEQ ID NO: 65) |
| Light Chain (LC) | EIVLTQSPGTLSVSPGERATLSCRASQSIGSSLHWYQQKPGQA<br>PRLLIKYASQSLSGIPDRFSGSGSGTDFTLTISRLEPEDFAVY<br>YCHQSSRLPHTFGQGTKVEIKRTVAAPSVFIFPPSDEQLKSGT<br>ASVVCLLNNFYPREAKVQWKVDNALQSGNSQESVTEQDSKDST<br>YSLSSTLTLSKADYEKHKVYACEVTHQGLSSPVTKSFNRGEC<br>(SEQ ID NO: 66) |

In some embodiments, the anti-IGF-1R inhibitor mAbs or antigen binding fragment thereof comprises a heavy chain amino acid sequence of SEQ ID NO:65 or at least a heavy chain with at least 85%, 90%, 95%, 97%, 98%, or 99% f sequence identity after optimal alignment with SEQ ID NO:65. Alternatively, or in addition, the anti-IGF-1R inhibitor mAbs or antigen binding fragment thereof may comprise a light chain having an amino acid sequence of SEQ ID NO:66 or at least a heavy chain with at least 85%, 90%, 95%, 97%, 98%, or 99% f sequence identity after optimal alignment with SEQ ID NO:66.

In some embodiments, said IGF-1R inhibitor is a small molecule.

Example 10

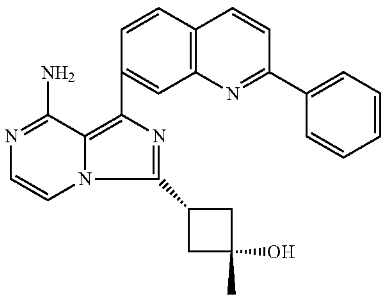

Linsitinib

Linsitinib and other related IGF-1R inhibitor small molecules and their methods of preparation can be found in U.S. Pat. No. 8,101,613, which is hereby incorporated by reference in its entirety. Linsitinib and the other IGF-1R inhibitors described therein are predicted to have activity in the activity measures or assessments for the treatment of TED described herein.

Example 11

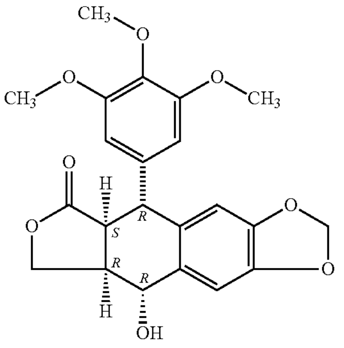

Picropodophyllin

Picropodophyllin (AXL1717) and other related IGF-1R inhibitor small molecules and their methods of preparation can be found in US U.S. Pat. No. 4,567,253, which is hereby incorporated by reference in its entirety. Picropodophyllin and the other IGF-1R inhibitors described therein are predicted to have activity in the activity measures or assessments for the treatment of TED described herein.

Example 12

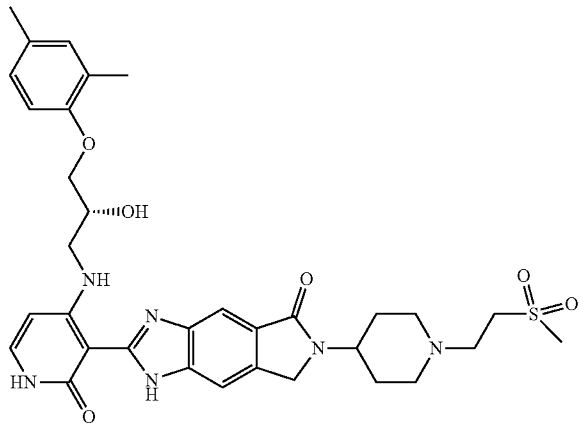

GTX-134

GTX-134 and other related IGF-1R inhibitor small molecules and their methods of preparation can be found in U.S. Pat. No. 8,063,225, which is hereby incorporated by reference in its entirety. GTX-134 and the other IGF-1R inhibitors described therein are predicted to have activity in the activity measures or assessments for the treatment of TED described herein.

Example 13

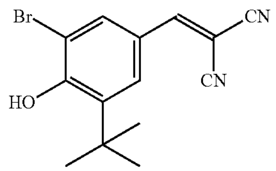

AG1024

AG1024 and other related IGF-1R inhibitor small molecules and their methods of preparation can be found in WO1995024190, which is hereby incorporated by reference in its entirety. AG1024 and the other IGF-1R inhibitors described therein are predicted to have activity in the activity measures or assessments for the treatment of TED described herein.

Example 14

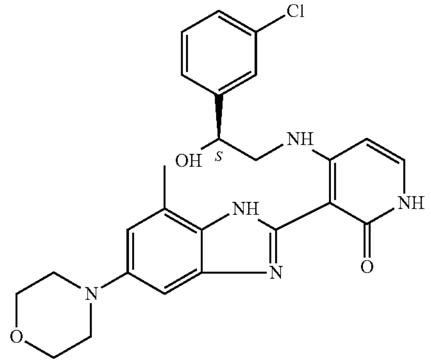

BMS-536924

BMS-536924 and other related IGF-1R inhibitor small molecules and their methods of preparation can be found in U.S. Pat. No. 7,081,454, which is hereby incorporated by reference in its entirety. BMS-536924 and the other IGF-1R inhibitors described therein are predicted to have activity in the activity measures or assessments for the treatment of TED described herein.

Example 15

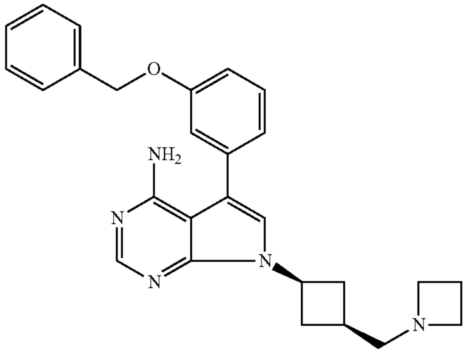

NVP-AEW541

NVP-AEW541 and other related IGF-1R inhibitor small molecules and their methods of preparation can be found in U.S. Pat. No. 7,326,699, which is hereby incorporated by reference in its entirety. NVP-AEW541 and the other IGF-1R inhibitors described therein are predicted to have activity in the activity measures or assessments for the treatment of TED described herein.

Example 16

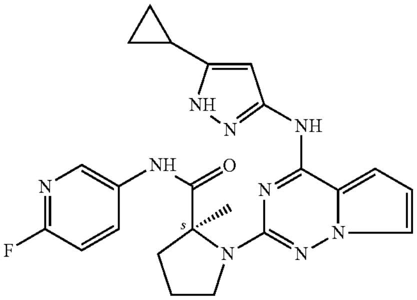

BMS-754807

BMS-754807 and other related IGF-1R inhibitor small molecules and their methods of preparation can be found in U.S. Pat. No. 7,534,792, which is hereby incorporated by reference in its entirety. BMS-754807 and the other IGF-1R inhibitors described therein are predicted to have activity in the activity measures or assessments for the treatment of TED described herein.

Example 17

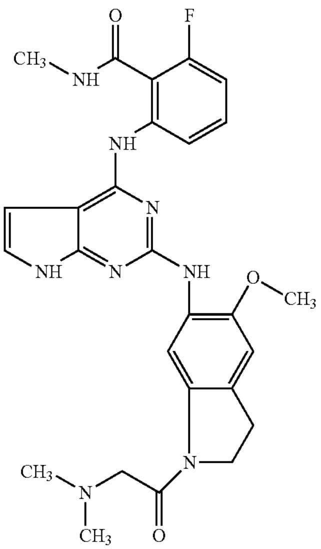

GSK1838705A

GSK1838705A and other related IGF-1R inhibitor small molecules and their methods of preparation can be found in U.S. Pat. No. 7,981,903, which is hereby incorporated by reference in its entirety. GSK1838705A and the other IGF-1R inhibitors described therein are predicted to have activity in the activity measures or assessments for the treatment of TED described herein.

Example 18

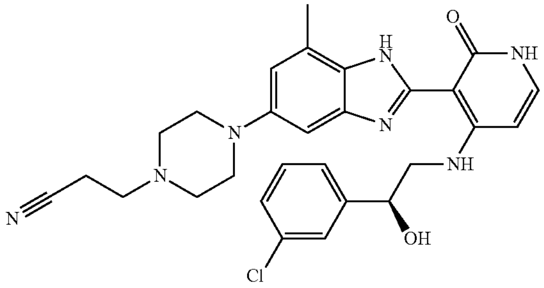

BMS-554417

BMS-554417 and other related IGF-1R inhibitor small molecules and their methods of preparation can be found in U.S. Pat. No. 7,081,454, which is hereby incorporated by reference in its entirety. BMS-554417 and the other IGF-1R inhibitors described therein are predicted to have activity in the activity measures or assessments for the treatment of TED described herein.

Example 19

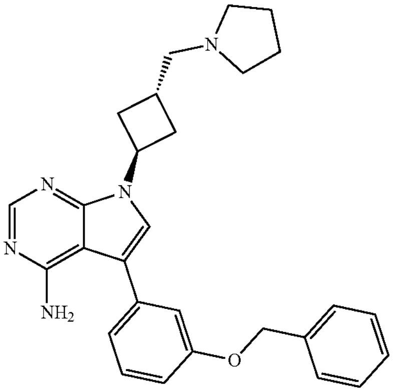

NVP-ADW742

NVP-ADW742 and other related IGF-1R inhibitor small molecules and their methods of preparation can be found in U.S. Pat. No. 7,326,699, which is hereby incorporated by reference in its entirety. NVP-ADW742 and the other IGF-1R inhibitors described therein are predicted to have activity in the activity measures or assessments for the treatment of TED described herein.

Example 20

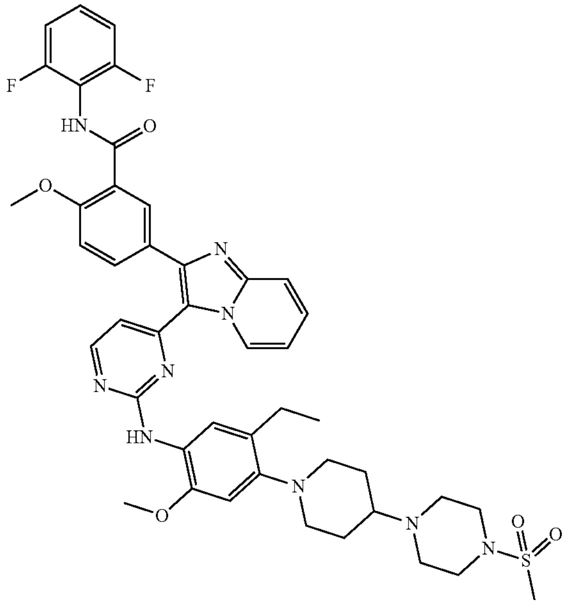

GSK1904529A

GSK1904529A and other related IGF-1R inhibitor small molecules and their methods of preparation can be found in U.S. Pat. No. 8,093,239, which is hereby incorporated by reference in its entirety. GSK1904529A and the other IGF-1R inhibitors described therein are predicted to have activity in the activity measures or assessments for the treatment of TED described herein.

Example 21

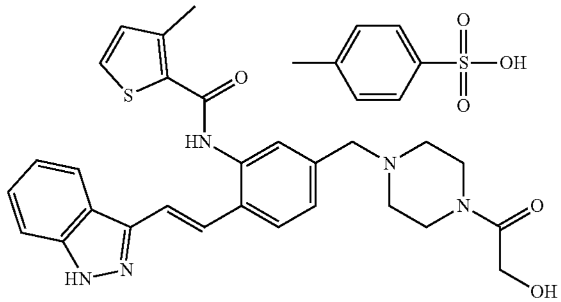

KW-2450

KW-2450, shown above as the tosylate salt but not limited thereto, and other related IGF-1R inhibitor small molecules and their methods of preparation can be found in WO2006080450, U.S. Pat. No. 7,605,272, and WO2011158931, which are hereby incorporated by reference in their entireties. KW-2450 and the other IGF-1R inhibitors described herein are predicted to have activity in the activity measures or assessments for the treatment of TED described herein.

Example 22

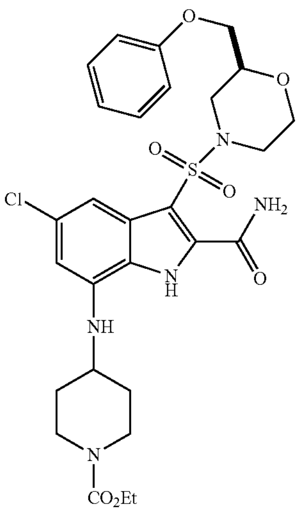

PL-225B

PL-225B and other related IGF-1R inhibitor small molecules and their methods of preparation can be found in WO2012145471 and WO2012007926, which is hereby incorporated by reference in its entirety. PL225B selectively inhibits IGF-1 R, resulting in inhibition of tumor cell proliferation and the induction of tumor cell apoptosis in IGF-1 R-overexpressing tumor cells. PL-225B and the other IGF-1R inhibitors described herein are predicted to have activity in the activity measures or assessments for the treatment of TED described herein.

Example 23

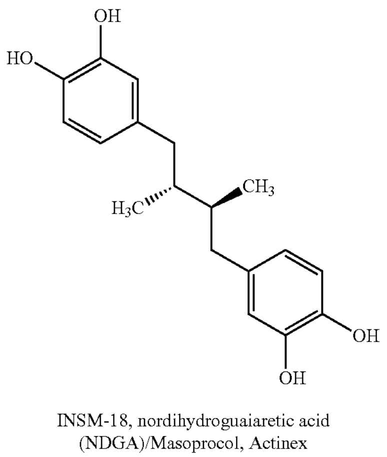 [SMILES: C[C@H](Cc1ccc(O)c(O)c1)[C@@H](C)Cc1ccc(O)c(O)c1]

INSM-18, nordihydroguaiaretic acid (NDGA)/Masoprocol, Actinex

INSM-18, nordihydroguaiaretic acid (NDGA) (shown above with relative stereochemistry, in which case it is also referred to as Masoprocol or Actinex, but not limited thereto) referred to in this Example as INSM-18, and other related IGF-1R inhibitor small molecules and their methods of preparation can be found at least in U.S. Pat. No. 2,373,192, which is hereby incorporated by reference in its entirety. INSM-18 directly inhibits activation of IGF-1 R and the c-erbB2/HER2/neu receptor, resulting in decreased proliferation of susceptible tumor cell populations. INSM-18 and the other IGF-1R inhibitors described herein are predicted to have activity in the activity measures or assessments for the treatment of TED described herein.

Example 24

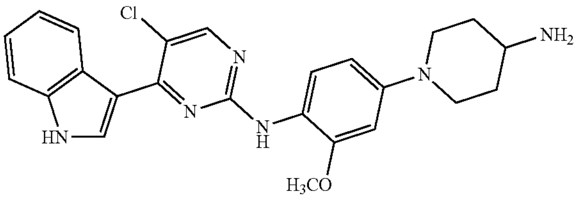

AZD3463

AZD3463 and other related IGF-1R inhibitor small molecules and their methods of preparation can be found in U.S. Pat. No. 8,461,170, which is hereby incorporated by reference in its entirety. AZD3463 is a potent ALK/IGF-1 R inhibitor, resulting in inhibition of neuroblastoma growth by overcoming crizotinib resistance and inducing apoptosis. AZD3463 and the other IGF-1R inhibitors described herein are predicted to have activity in the activity measures or assessments for the treatment of TED described herein.

Example 25

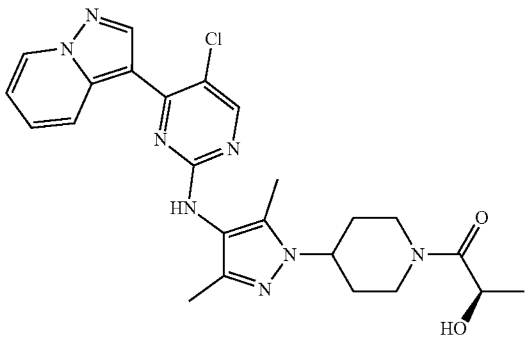

AZD9362

AZD9362 and other related IGF-1R inhibitor small molecules and their methods of preparation can be found in Degorce, S L et al., "Discovery of a Potent, Selective, Orally Bioavailable, and Efficacious Novel 2-(Pyrazol-4-ylamino)-pyrimidine Inhibitor of the Insulin-like Growth Factor-1 Receptor (IGF-1R)," J Med Chem (2016), 59(10), 4859-4866., which is hereby incorporated by reference in its entirety. AZD9362 is a dual inhibitor of IGF-1R/InsR. AZD9362 and the other IGF-1R inhibitors described herein are predicted to have activity in the activity measures or assessments for the treatment of TED described herein.

Example 26

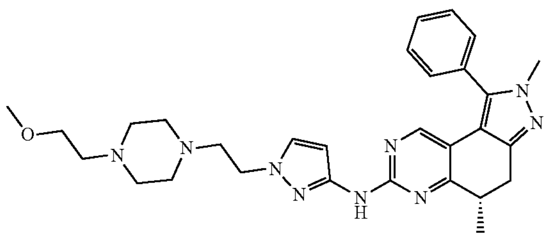

BI885578

BI885578 and other related IGF-1R inhibitor small molecules and their methods of preparation can be found in U.S. Ser. No. 10/414,769, U.S. Pat. No. 9,150,578, and Sanderson M P et al., “BI 885578, a Novel IGF1R/INSR Tyrosine Kinase Inhibitor with Pharmacokinetic Properties That Dissociate Antitumor Efficacy and Perturbation of Glucose Homeostasis,” Mol Cancer Ther 2015 December; 14(12): 2762-72, which are hereby incorporated by reference in its entirety. BI885578 is an IGF1R/INSR tyrosine kinase inhibitor distinguished by rapid intestinal absorption and a short in vivo half-life as a result of rapid metabolic clearance, resulting in inhibition of cell proliferation and induction of apoptosis in tumors. BI885578 and the other IGF-1R inhibitors described herein are predicted to have activity in the activity measures or assessments for the treatment of TED described herein.

Example 27

BI893923

BI893923 and other related IGF-1R inhibitor small molecules and their methods of preparation can be found in U.S. Pat. No. 8,546,443 and Titze MI et al., “An allometric pharmacokinetic/pharmacodynamics model for BI 893923, a novel IGF-1 receptor inhibitor,” Cancer Chemother Pharmacol 2017 March;79(3):545-558, which is hereby incorporated by reference in its entirety. BI893923 is an IGF1R/INSR tyrosine kinase inhibitor demonstrating anti-tumor efficacy and good tolerability. BI893923 and the other IGF-1R inhibitors described herein are predicted to have activity in the activity measures or assessments for the treatment of TED described herein.

Example 28

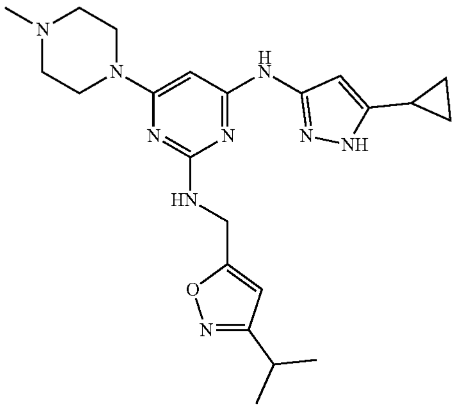

XL-228

XL-228 and other related IGF-1R inhibitor small molecules and their methods of preparation can be found in US20090232828, which is hereby incorporated by reference in its entirety. XL-228 is a broad protein kinase inhibitor that contributes to cell proliferation, cell survival, and resistance to cytotoxic agents. XL-228 and the other IGF-1R inhibitors described herein are predicted to have activity in the activity measures or assessments for the treatment of TED described herein.

Example 29

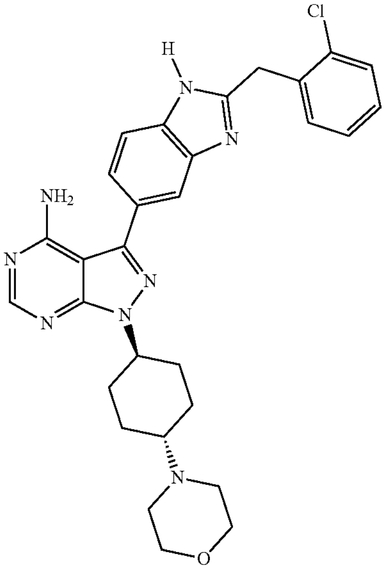

A-928605

A-928605 and other related IGF-1R inhibitor small molecules and their methods of preparation can be found in U.S. Pat. No. 7,772,231 and WO2007079164, which are hereby incorporated by reference in its entirety. A-928605 is a potent inhibitor of IGF-IR both on the purified enzyme and intracellular IGF-IR phosphorylation. A-928605 and the other IGF-1R inhibitors described herein are predicted to have activity in the activity measures or assessments for the treatment of TED described herein.

Example 30

Istiratumab (MM-141)

Istiratumab and other related IGF-1R inhibitor antibodies and their methods of preparation can be found in U.S. Pat. No. 8,476,409, which is hereby incorporated by reference in its entirety.

| Heavy Chain CDRs - Istiratumab | | |
|---|---|---|
| HCDR1 | HCDR2 | HCDR3 |
| GFMFSRYPMH (SEQ ID NO: 67) | ISGSGGATPYADSVKG (SEQ ID NO: 68) | DFYQILTGNAFDY (SEQ ID NO: 69) |

| Light Chain CDRs - Istiratumab | | |
|---|---|---|
| LCDR1 | LCDR2 | LCDR3 |
| RASQGISSYLA (SEQ ID NO: 70) | AKSTLQS (SEQ ID NO: 71) | QQYWTFPLT (SEQ ID NO: 72) |
| Heavy Chain (HC) | EVQLLQSGGGLVQPGGSLRLSCAASGFMFSRYPMHWVRQAPGKGLE<br>WVGSISGSGGATPYADSVKGRFTISRDNSKNTLYLQMNSLRAEDTAV<br>YYCAKDFYQILTGNAFDYWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQQ<br>GNVFSCSVMHEALHNHYTQKSLSLSPGGGGGSGGGGSGGGGSQVQL<br>VQSGGGLVQPGGSLRLSCAASGFTFDDYAMHWVRQAPGKGLEWVA<br>GISWDSGSTGYADSVKGRFTISRDNAKNSLYLQMNSLRAEDTALYYC<br>ARDLGAYQWVEGFDYWGQGTLVTVSSASTGGGGSGGGGSGGGGSG<br>GGGSSYELTQDPAVSVALGQTVRITCQGDSLRSYYASWYQQKPGQAP<br>VLVIYGKNNRPSGIPDRFSGSTSGNSASLTITGAQAEDEADYYCNSRD<br>SPGNQWVFGGGTKVTVLG<br>(SEQ ID NO: 73) | |
| Light Chain (LC) | DIQMTQSPSSLSASLGDRVTITCRASQGISSYLAWYQQKPGKAPKLLIY<br>AKSTLQSGVPSRFSGSGSGTDFTLTISSLQPEDSATYYCQQYWTFPLTF<br>GGGTKVEIKRTVAAPSVFIFPPSDEQLKSGTASVVCLLNNFYPREAKV<br>QWKVDNALQSGNSQESVTEQDSKDSTYSLSSTLTLSKADYEKHKVY<br>ACEVTHQGLSSPVTKSFNRGEC<br>(SEQ ID NO: 74) | |

Some embodiments of the disclosure are anti-IGF-1R inhibitor mAbs or antigen binding fragments thereof, comprising a heavy chain comprising a variable heavy chain CDR1, a variable heavy chain CDR2, and a variable heavy chain CDR3, wherein the variable heavy chain CDR1 comprises an amino acid sequence SEQ ID NO:67, the variable heavy chain CDR2 comprises an amino acid sequence SEQ ID NO:68; and the variable heavy chain CDR3 comprises an amino acid sequence SEQ ID NO:69 or at least a CDR with at least 80% f sequence identity after optimal alignment with SEQ ID NO:67, SEQ ID NO:68, and SEQ ID NO:69.

The anti-IGF-1R inhibitor mAbs or antibody or antigen binding fragment thereof may additionally comprise a light chain which is paired with the heavy chain to form an antigen binding domain. In some embodiments, the light chain comprises a variable light chain CDR1, a variable light chain CDR2, and a variable light chain CDR3, wherein the variable light chain CDR1 comprises an amino acid sequence SEQ ID NO:70, the variable light chain CDR2 comprises an amino acid sequence SEQ ID NO:71; and the variable light chain CDR3 comprises an amino acid sequence SEQ ID NO:72 or at least a CDR with at least 80% f homology after optimal alignment with SEQ ID NO:70, SEQ ID NO:71, and SEQ ID NO:72.

In some embodiments, the anti-IGF-1R inhibitor mAbs or antigen binding fragment thereof comprises a heavy chain amino acid sequence of SEQ ID NO:73 or at least a heavy chain with at least 85%, 90%, 95%, 97%, 98%, or 99% f sequence identity after optimal alignment with SEQ ID NO:73. Alternatively, or in addition, the anti-IGF-1R inhibitor mAbs or antigen binding fragment thereof may comprise a light chain having an amino acid sequence of SEQ ID NO:74 or at least a heavy chain with at least 85%, 90%, 95%, 97%, 98%, or 99% f sequence identity after optimal alignment with SEQ ID NO:74.

Example 31

Description of Randomized, Double-Masked, Placebo- and/or Active-Controlled, Parallel-Group, Multicenter Study Evaluating IGF-1R Inhibition in Subjects with Chronic/Inactive Thyroid Eye Disease (TED)

Overview. Multicenter, optionally double-masked, randomized, parallel-group, placebo- and/or active- (e.g., teprotumumab-) controlled clinical trials may be conducted to determine the efficacy and safety of any Study Drug disclosed herein in patients with either active/acute, or inactive/chronic, moderate-to-severe TED. The study may be conducted in male and non-pregnant female patients between the ages of 18 and 80 years, inclusive. Patients will be enrolled and randomly assigned on Day 1 in an appropriate ratio, (e.g., 1:1, 2:1, or 3:1) to receive placebo or active control or Study Drug administered as described herein. Subjects will be screened for the study within 4 weeks prior to the Baseline (Day 1) Visit. Subjects may be stratified by duration of disease, ≤2 years or >2 years.

Patient Population. The study may be designed to assess activity and safety in either 1) patients with moderate-to-severe active/acute TED or 2) moderate-to-severe inactive/chronic TED. Moderate to severe acute disease may be defined as: i) ≥3 mm proptosis beyond race/gender norms or beyond patient's pre-TED, ii) clinical activity score of at least 3, and iii) within 15 months of symptom onset. Moderate to severe chronic disease may be defined as: i) ≥3 mm proptosis beyond race/gender norms or beyond patient's pre-TED, ii) clinical activity score of 0 or 1, and iii) no significant progression or inflammatory symptoms within 1 year.

Treatment Period. The planned duration of the Treatment Period may be, e.g., 12, 24, or 48 weeks (3, 6, or 12 months), with an optional open-label extension study period. At the End of the Treatment Period—Week 12, Week 24, or week 48, as appropriate—primary endpoint responders, as well as non-responders who choose not to enroll in the open-label extension study, or will enter a safety Follow-Up Period. Subjects who are considered non-responders at the end of the treatment period may enroll in the open-label extension study.

All subjects will enter a Treatment Period of, e.g., 12-week or 24-week or 48-week. All study drug dosing or initial study drug dosing will be performed at the clinic under the supervision of clinic staff. On each dosing day, scheduled assessments (except for AE and concomitant medication use monitoring, which will be monitored throughout the clinic visit) will be completed prior to study drug dosing. Additional phone/email contacts and clinic visits may also be conducted for any subject experiencing a drug-related adverse event.

Study Endpoints. The primary end point may be either proptosis or diplopia, e.g. in the study eye. Proptosis may be assessed either as proportion of responders (where a responder is defined as a patient experiencing a ≥2 mm reduction from Baseline in the study eye without deterioration—≥2 mm increase—of proptosis in the fellow eye) or assessed as a continuous variable (i.e., average or median change from baseline), measured using a standardized exophthalmometer (e.g., Hertel). Diplopia may be assessed using any of the subject Gorman scale, the Goldman perimeter, or the cervical range of motion method, as long as the same assessment is used for all patients.

Secondary end points, measured as continuous variables, may include: proptosis, diplopia, orbital pain, MDI and PVR for inferior rectus, superior rectus, the medial rectus, lateral rectus and orbital fat, clinical activity score (CAS), circumference of calf and area of the lesion, inflammatory and fibrotic biomarkers, transcriptomics associated with IGF-1R inhibition, and results on the Graves' ophthalmopathy-specific quality-of-life questionnaire (GO-QoL) or appearance and functioning subscales thereof. Adverse events will also be assessed.

Subjects who prematurely discontinue study drug dosing will return to the clinic and undergo the scheduled End of Treatment Period assessments and will be encouraged to remain in the study and participate in the Follow-Up Period.

Inclusion Criteria. Major inclusion criteria will include the following:

- Written informed consent.
- Male or female subject between the ages of 18 and 80 years, inclusive, at Screening.
- For chronic/inactive TED:
  - Moderate-to-severe chronic/inactive TED (not sight-threatening but has an appreciable impact on daily life), usually associated with one or more of the following: lid retraction>2 mm, moderate or severe soft tissue involvement, and/or inconstant or constant diplopia.
  - Initial diagnosis of TED>2 years prior to Screening. Clinical diagnosis of stable, chronic/inactive TED as determined by patient medical records indicating a CAS≤1 in both eyes for at least 1 year prior to Screening or all of the following: (a) no progression in proptosis for at least 1 year prior to Screening; (b) if subject has history of diplopia due to TED, no progression in diplopia for at least 1 year prior to Screening; (c) no inflammatory symptoms for at least 1 year prior to Screening; and no new TED symptoms for at least 1 year prior to Screening.
  - CAS≤1 at Screening and Baseline visits.
- For acute/active TED:
  - Moderate-to-severe active TED (not sight-threatening but has an appreciable impact on daily life), usually associated with one or more of the following: lid retraction≥2 mm, moderate or severe soft tissue involvement, and/or inconstant or constant diplopia.
  - Onset of active TED symptoms (as determined by patient records) within 9 months prior to Baseline.
  - CAS≥3 or ≥4 (on the 7-item scale) for the most severely affected eye at Screening and Baseline.
  - Optionally, clinical diagnosis of Graves' disease associated with active TED.
- Exophthalmos≥3 mm above normal for race and gender or compared with the patient's pre-TED state, in the opinion of the investigator (e.g., according to pre-disease patient photos).
- Subjects must be euthyroid with the baseline disease under control, or have mild hypo- or hyperthyroidism (defined as free thyroxine [FT4] and free triiodothyronine [FT3] levels<50% above or below the normal limits) at Screening. Every effort should be made to correct the mild hypo- or hyperthyroidism promptly and to maintain the euthyroid state for the full duration of the clinical trial.
- Does not require immediate surgical ophthalmological intervention and is not planning corrective surgery/irradiation during the course of the study.
- Diabetic subjects must have HbA1c≤8.0%.

Exclusion Criteria. Patients may be ineligible for study participation if they meet any of the following criteria:

- Decreased best corrected visual acuity due to optic neuropathy as defined by a decrease in vision of 2 lines on the Snellen chart, new visual field defect, or color defect secondary to optic nerve involvement within the last 6 months.
- Corneal decompensation unresponsive to medical management.
- Decrease in CAS≥1 in either eye (for chronic/inactive TED) or of ≥2 points in the study eye (for acute/active TED) between Screening and Baseline.
- Decrease in proptosis of ≥2 mm in the study eye between Screening and Baseline.
- Prior orbital irradiation, orbital decompression, or strabismus surgery.

Intravenous (IV) or oral steroids for the treatment of TED or use of steroid eye drops for the treatment of TED within 6 months prior to Screening.

Corticosteroid use for conditions other than TED within 4 weeks prior to Screening (topical steroids for dermatological conditions and inhaled steroids are allowed).

Previous treatment with rituximab (Rituxan® or MabThera®).

Previous treatment with teprotumumab.

Treatment with tocilizumab (Actemra® or Roactemra®) or any other non-steroid immunosuppressive agent within 6 months prior to Screening.

Use of an investigational agent for any condition within 60 days prior to Screening or anticipated use during the course of the trial.

Identified pre-existing ophthalmic disease that, in the judgment of the Investigator, would preclude study participation or complicate interpretation of study results.

Malignant condition in the past 12 months (except successfully treated basal/squamous cell carcinoma of the skin).

Pregnant or lactating women.

Current drug or alcohol abuse, or history of either within the previous 2 years, in the opinion of the Investigator or as reported by the subject.

Biopsy-proven or clinically suspected inflammatory bowel disease (e.g., diarrhea with or without blood or rectal bleeding associated with abdominal pain or cramping/colic, urgency, tenesmus, or incontinence for more than 4 weeks without a confirmed alternative diagnosis OR endoscopic or radiologic evidence of enteritis/colitis without a confirmed alternative diagnosis).

Known hypersensitivity to any of the components of the Study Drug [or prior hypersensitivity reactions to mAbs]

Any other condition that, in the opinion of the Investigator, would preclude inclusion in the study.

Previous enrollment in this study or participation in a prior clinical trial for the Study Drug.

Human immunodeficiency virus, hepatitis C or hepatitis B infections.

Alanine aminotransferase (ALT) or aspartate aminotransferase (AST)>3 times the upper limit of normal (ULN) or estimated glomerular filtration rate of <30 mL/min/1.73m2 at Screening.

Study Objectives

The overall objective of the study will be to investigate the efficacy, safety, and tolerability of a monoclonal antibody (mAb) or small molecule inhibitor of the insulin-like growth factor-1 receptor (IGF-1R), in the treatment of subjects with acute or chronic TED.

The primary objective is to evaluate the effect of Study Drug versus placebo or teprotumumab on the mean change from Baseline to End of the Treatment Period (Week 12, Week 24, or Week 48) in proptosis measurement or diplopia (measured by improvement in subjective Gorman scale, Goldmann perimeter, or Cervical range of motion method) in the study eye in subjects with Chronic/inactive TED.

Other objectives include the following:

Evaluate the effect of Study Drug versus placebo or teprotumumab on the mean change from Baseline to Week 12, Week 24, and/or Week 48 in the Graves' Ophthalmopathy Quality of Life (GO-QoL) questionnaire appearance and visual functioning sub-scales.

Evaluate the effect of Study Drug versus placebo or teprotumumab on the proptosis responder rate (i.e., the percentage of subjects with a ≥2 mm reduction from Baseline in the study eye without deterioration [≥2 mm increase] of proptosis in the fellow eye) at Week 12, Week 24, and/or Week 48.

Evaluate the effect of Study Drug versus placebo or teprotumumab on the binocular diplopia responder rate (i.e., the percentage of subjects with baseline diplopia>0 who have a reduction of ≥1 grade) at Week 12, Week 24, and/or Week 48.

Evaluate the effect of Study Drug versus placebo or teprotumumab on the mean change from Baseline to Week 12, Week 24, and/or Week 48 in orbital pain (measured on a visual analog scale [VAS]).

Evaluate the effect of Study Drug versus placebo or teprotumumab on the mean change from Baseline to Week 12, Week 24, and/or Week 48 in the Muscle Diameter Index (MDI) and Pixel Value Ratio (PVR) for the inferior rectus, superior rectus, the medial rectus, lateral rectus and orbital fat (measured by magnetic resonance imaging [MRI]) on subjects where MRI is obtained.

Evaluate the effect of Study Drug versus placebo or teprotumumab on percentage of subjects with a Clinical Activity Score (CAS) of ≥3 in the study eye at Week 12, Week 24, and/or Week 48.

Evaluate the effect of Study Drug versus placebo or teprotumumab on the mean change from Baseline to Week 12, Week 24, and/or Week 48 in the circumference of calf and area of the lesion (maximum length and width of lesion) in subjects with baseline pretibial myxedema (PTM).

Evaluate the effect of Study Drug versus placebo or teprotumumab on changes from Baseline at Weeks 3, 12, 24, and/or 48 in inflammatory and fibrotic biomarkers.

Evaluate the effect of Study Drug versus placebo or teprotumumab on changes from Baseline at Weeks 3, 12, 24, and/or 48 in transcriptomics associated with IGF-1R inhibition.

Pharmacokinetic and Anti-drug Antibody (ADA) Objectives include the following:

Evaluate pharmacokinetics (PK) of Study Drug to estimate exposure.

Evaluate the immunogenicity of Study Drug.

Safety and Tolerability Objectives include the following:

Assess the safety and tolerability of Study Drug versus placebo or teprotumumab based on adverse event (AE) reports, adverse events of special interest (AESI; hyperglycemia, hearing impairment and muscle spasms), concomitant medication use, ophthalmic examinations, vital signs, clinical safety laboratory evaluations, electrocardiograms (ECGs) and immunogenicity.

Restrictions During Study

The trial will comprise three phases: screening (28 days prior to Day 1), treatment or intervention period (Day 1 to Week 12, Week 24, and/or Week 48), and follow-up for, e.g., 6 weeks of more after the nd of the treatment period. Screening involves one to three visits. During the treatment period, patients will be assessed at Day 1/Baseline and every 3 weeks for 12, 24, or 48 weeks. Efficacy may be assessed throughout the Treatment Period, e.g.:

CAS at Day 1/Baseline and weeks 12 and 24 for a study with a 24-week treatment period, or a similar schedule adjusted for a 12 or 48 week treatment period;

proptosis and diplopia at Day 1/Baseline and weeks 3, 6, 12, 18, and 24 for a study with a 24-week treatment period, or a similar schedule adjusted for a 12 or 48 week treatment period;

PTM at Day 1/Baseline and weeks 12 and 24 for a study with a 24-week treatment period, or a similar schedule adjusted for a 12 or 48 week treatment period; and orbital pain at Day 1/Baseline and weeks 3, 6, 12, 18, and 24 for a study with a 24-week treatment period, or a similar schedule adjusted for a 12 or 48 week treatment period.

Data from the end of the Treatment Period, i.e. week 12, 24, or 48, will be used to assess the primary and secondary end points. A change of 2 points in the 7-component CAS will be considered to be clinically relevant, as will achievement of a CAS of 0 or 1 in acute/active TED patients. Proptosis will be assessed with the use of a Hertel exophthalmometer. A change of 2 mm will be considered to be clinically relevant. Quality of life will be evaluated with the use of the Graves' ophthalmopathy-specific quality-of-life questionnaire (GO-QoL), comprising two subscales assessed separately or in combination; scores on each subscale as well as the score on the overall GO-QoL scale have a range of 0 to 100 points, with a change of 8 points being considered to be clinically relevant. Subjective diplopia will be assessed by improvement in subjective Gorman scale or Goldmann perimeter or Cervical range of motion method.

Institutional review and ethics committees of the participating centers and the investigators will approve the research protocol. Witnessed, written informed consent will be obtained from all patients. Data will be obtained by the investigators and their staff.

Moieties/Interventions Used in the Trial

Drugs for evaluation in TED in the present study may include any of the biologic or small molecule drugs listed in Examples 1-22. Teprotumumab may be provided according to its marketed formulation. Other study drugs will be provided as given below or as appropriate. The placebo will be appropriate to the given Study Drug, e.g. IV saline or buffer solution or matching placebo tablet/capsule. Patients will receive equivalent types and numbers of administrations of either a Study Drug listed in Table 1, or teprotumumab, or placebo. Dosages are provided below. For example, for subjects assigned to the teprotumumab group, the drug may be administered every 3 weeks starting with an initial dose of 10 mg per kilogram of body weight, followed by 20 mg per kilogram for the remaining infusions. Dosages or frequency of administration can be altered as deemed appropriate by a clinician or study coordinator.

As disclosed herein for the anti-IGF-R1 antibody drugs listed in Table 1, the lower end of the dose range appropriate for use in TED were estimated from the minimum concentration ($C_{min}$) that would achieve an in vitro $IC_{50}$ as disclosed in the art. The higher end of the dose range appropriate for use in TED was estimated as three-fold of the recommended phase 2 dose (RP2D) if it is not the maximum tolerated dose (MTD), or 2.5-fold of the RP2D if it is the MTD.

As disclosed herein for the anti-IGF-R1 small molecule drugs listed in Table 1, the lower end of the dose range appropriate for use in TED were estimated from the maximum concentration ($C_{max}$) that would achieve an in vitro $IC_{50}$ as disclosed in the art. The higher end of the dose range appropriate for use in TED was estimated as three-fold of the recommended phase 2 dose (RP2D) if it is not the maximum tolerated dose (MTD), or 2.5-fold of the RP2D if it is the MTD.

Dose ranges in Table 1 are given as total dose for a 3-week interval (antibodies) or daily (small molecules) unless otherwise specified.

TABLE 1

List of Study Drugs.

| Ex. | Drug Name(s) | Drug Type | Oncology RP2D | Dose (s): range and/or examples for TED | Route, $T_{1/2}$ |
|---|---|---|---|---|---|
| n/a | TEPEZZA (teprotumumab) | Antibody | * | 5-20 mg/kg Q3W; e.g. 10 or 20 mg/kg Q3W | IV; 8 days |
| 1 | Dalotuzumab (MK-0646) | antibody | 10 mg/kg QW, 20 mg/kg Q2W, 30 mg/kg Q3W | total dose 1-90 mg/kg or 75-6800 mg Q3W; or 0.6-60 mg/kg or 45-4500 mg Q2W; or 0.3-30 mg/kg or 22-2300 mg QW | IV; 5 days |
| 2 | Ganitumab (AMG 479) | antibody | 12 mg/kg Q2W | total dose 1-60 mg/kg or 75-4500 mg Q3W; 0.6-40 mg/kg or 45-3000 mg Q2W; 0.3-20 mg/kg; or 22-1500 QW | IV; 6-9 days |
| 3 | Xentuzumab (BI 836845) | antibody | 1000 mg/kg | 1-112 mg/kg or 75-8400 mg Q3W; or 0.6-75 mg/kg or 45-5700 mg Q2W; or 0.3-38 mg/kg or 22-2900 mg QW | IV |
| 4 | AVE1642 | antibody | 6 mg/kg Q3W | total dose 1-60 mg/kg or 75-4500 mg Q3W; or 0.6-40 mg/kg or 45-3000 mg Q2W; or 0.3-20 mg/kg or 22-1500 mg QW | IV, 8 days |
| 5 | Figitumumab (CP-751) | antibody | 20 mg/kg Q3W | total dose 1-60 mg/kg or 75-4500 mg Q3W; or 0.6-40 mg/kg or 45-3000 mg Q2W; or 0.3-20 mg/kg or 22-1500 mg QW | IV; 20 days |
| 6 | Dusigitumab (MEDI-573) | antibody | 30-45 mg/kg | total dose 1-75 mg/kg or 75-5700 mg Q3W; or 0.6-50 mg/kg or 45-3800 mg Q2W; or 0.3-25 mg/kg or 22-1900 mg QW | IV |
| 7 | Cixutumumab (IMC-A12) | antibody | 10 mg/kg Q2W | total dose 1-45 mg/kg or 75-3400 mg Q3W; or 0.6-30 mg + D2/kg or 45-2300 mg Q2W; or 0.3-15 mg/kg or 22-1200 mg QW | IV; 5 days |

TABLE 1-continued

List of Study Drugs.

| Ex. | Drug Name(s) | Drug Type | Oncology RP2D | Dose (s): range and/or examples for TED | Route, $T_{1/2}$ |
|---|---|---|---|---|---|
| 8 | BIIB022 | antibody | 30 mg/kg Q3W | total dose 1-75 mg/kg or 75-5700 mg Q3W; or 0.6-50 mg/kg; or 45-3800 mg Q2W; or 0.3-25 mg/kg or 22-1900 mg | IV; 15 days |
| 9 | Robatumumab (SCH 717454) | antibody | 10 mg/kg Q2W | total dose 1-75 mg/kg or 75-5700 mg Q3W; or 0.6-50 mg/kg or 45-3800 mg Q2W; or 0.3-25 mg/kg or 22-1900 mg QW | IV |
| 10 | Linsitinib (OSI-906) | Small molecule | 150 mg BID (tested in Ph2); or 600 mg QD for days 1-3 or 1-7 for every 14 days | QD: 10-750 mg/day for continuous dosing; or 10-1500 mg/day for intermittent dosing (for up to 7 days of every 14 days); BID: 6-500 mg for continuous dosing; 6-1000 mg for intermittent dosing (for up to 7 days of every 14 days); TID: 3-250 mg for continuous dosing; 3-500 mg for intermittent dosing (for up to 7 days of every 14 days) | oral; 2-4 hrs |
| 11 | Picropodophyllin (AXL1717) | small molecule | 390 mg BID (tested in Ph2 NSCLC) | QD: 20-2000 mg; BID: 13-1400 mg; or TID: 6-700 mg | oral, e.g. susp. |
| 12 | GTx-134 | small molecule | ** | 1-2000 mg QD; or 0.6-1400 mg BID; or 0.3-700 mg TID. | oral |
| 13 | AG1024 | small molecule | ** | 1-2000 mg QD; or 0.6-1400 mg BID; or 0.3-700 mg TID. | oral |
| 14 | BMS-536924 | small molecule | ** | 1-2000 mg QD; or 0.6-1400 mg BID; or 0.3-700 mg TID. | oral |
| 15 | NVP-AEW541 | small molecule | ** | 1-2000 mg QD; or 0.6-1400 mg BID; or 0.3-700 mg TID. | oral |
| 16 | BMS-754807 | small molecule | ** | 5-600 mg QD; 3-400 mg BID; 1-200 mg TID | oral |
| 17 | GSK1838705A | small molecule | ** | 1-2000 mg QD; or 0.6-1400 mg BID; or 0.3-700 mg TID. | oral |
| 18 | BMS-554417 | small molecule | ** | 1-2000 mg QD; or 0.6-1400 mg BID; or 0.3-700 mg TID. | oral |
| 19 | NVP-ADW742 | small molecule | ** | 1-2000 mg QD; or 0.6-1400 mg BID; or 0.3-700 mg TID. | oral |
| 20 | GSK1904529A | small molecule | ** | 1-2000 mg QD; or 0.6-1400 mg BID; or 0.3-700 mg TID. | oral |
| 21 | KW-2450 | small molecule | ** | 1-100 mg QD; 0.7-70 mg BID; 0.3-30 mg TID | oral |
| 22 | PL-2258 / PL-2256 | small molecule | ** | 1-2000 mg QD; or 0.6-1400 mg BID; or 0.3-700 mg TID. | Oral; 21d |
| 23 | INSM-18, nordihydroguaiaretic acid (NDGA)/ Masoprocol, Actinex, TT-100 | small molecule | ** | 1-2000 mg QD; or 0.6-1400 mg BID; or 0.3-700 mg TID. | oral |
| 24 | AZD3463 | small molecule | ** | 1-2000 mg QD; or 0.6-1400 mg BID; or 0.3-700 mg TID. | oral |
| 25 | AZD9362 | small molecule | ** | 1-2000 mg QD; or 0.6-1400 mg BID; or 0.3-700 mg TID. | oral |
| 26 | BI885578 | small molecule | ** | 1-2000 mg QD; or 0.6-1400 mg BID; or 0.3-700 mg TID. | oral |
| 27 | BI893923 | small molecule | ** | 1-2000 mg QD; or 0.6-1400 mg BID; or 0.3-700 mg TID. | oral |
| 28 | XL-228 | small molecule | ** | 1-2000 mg QD; or 0.6-1400 mg BID; or 0.3-700 mg TID. | oral |
| 29 | A-928605 | small molecule | ** | 1-2000 mg QD; or 0.6-1400 mg BID; or 0.3-700 mg TID. | oral |
| 30 | Istiratumab (MM-141) | antibody | 2.8 g IV q2w | 1-112 mg/kg or 75-8400 mg Q3W; or 0.7-75 mg/kg or 45-5700 mg Q2W; or 0.3-38 mg/kg or 22-2900 mg QW | IV |

In Table 1 above, * indicates that RP21D is known in the art; and ** indicates that prior clinical experience with the IGF-1R inhibitor is not known to be published.

In some embodiments, other IGF-1R antibodies may be useful as described herein and are encompassed within the present disclosure. In some embodiments, if prior clinical experience with an anti-IGF-R1 antibody is not published, a dosage appropriate for use for the present disclosure may be 1-112 mg/kg or 75-8400 mg every 3 weeks (Q3W); or 0.6-75 mg/kg or 45-5700 mg every 2 weeks (Q2W); or 0.3-38 mg/kg or 22-2900 mg weekly (QW).

In some embodiments, other IGF-1R small molecule drugs may be useful as described herein and are encompassed within the present disclosure. In some embodiments, if prior clinical experience with a small molecule IGF-1R inhibitor drug is not published, a dosage appropriate for use for the present disclosure may be 1-2000 mg for once daily administration (QD); or 0.6-1400 mg for twice daily administration (BID); or 0.3-700 mg for three-times daily administration (TID).

On Day 1 of the Treatment Period, subjects will be randomized in an appropriate (e.g., a 2:1 or 1:1 ratio, optionally stratified by duration of disease) to the Study Drug. Placebo doses (IV saline or buffer solution or matching placebo tablet/capsule) will be used to maintain the blind due to differing administration schedules and/or methods of administration with the active comparator.

Detailed Study Procedures

At the Baseline (Day 1) Visit, the eye with the more significant proptosis may be defined as the "study eye." If both eyes are affected equally, the Investigator may choose the "study eye." Both eyes will be assessed for efficacy but the study eye may be used to assess the primary outcome measure.

Efficacy will be assessed by proptosis (measured as exophthalmos evaluation of the Clinical Measures of Severity using a Hertel instrument provided by the Sponsor for consistency in measurement), quality of life (using GO-QoL questionnaire), diplopia (measured as part of the Clinical Measures of Severity or using Goldmann perimeter or cervical range of motion method), CAS (7-item or 10-item scale), orbital pain (using a 10-cm VAS), orbital MRI, and/or PTM (calf circumference and area of lesion).

Blood samples for Study Drug PK assessment will be collected prior to dosing on Day 1 and at End of Treatment Period, e.g., Week 12, Week 24, or Week 48. Blood samples may be collected and analyzed for inflammatory and fibrotic biomarkers and evaluated for transcriptomics associated with IGF-1R inhibition prior to treatment on Day 1 and after treatment throughout the study, e.g. for a 24-week treatment period, at Weeks 3, 12, and 24.

Safety will be assessed via AE and concomitant medication use monitoring, immunogenicity testing, ophthalmic examinations, vital signs, clinical safety laboratory evaluations (complete blood count and chemistry (including thyroid panel and HbA1c), pregnancy testing (if applicable), and ECGs.

A summary of the study procedures, including the timing for each, is provided in the Schedule of Assessments (Table 2).

Informed Consent: Informed consent will be obtained from each subject during Screening.

Inclusion/Exclusion Criteria: Inclusion/exclusion criteria will be reviewed with each subject at Screening and on the Day 1/Baseline visit.

Demographics: Demographic data may be obtained from each subject during Screening.

Medical History: Medical history, including thyroid disease history and treatment, TED history and treatment, and tobacco use history, will be obtained from each subject at Screening and on the Day 1/Baseline visit. TED must be either i) acute/active TED (onset of symptoms within 9 months prior to Baseline) or ii) stable, chronic/inactive (not progressing, non-sight threatening but appreciable impact on daily life) with TED diagnosed>2 years, but no longer than 7 years prior to Screening.

Weight: Weight may be recorded at Screening, and throughout the study, e.g. for a 24-week treatment period, Week 12/Month 3, and Week 24/Month 6. Dosing may be adjusted if there is a change in weight during the Treatment Period. The weight obtained mid-study can be used in dose calculations for later doses.

Randomization: On Day 1 (Baseline), subjects will be randomized and receive the first dose of study drug. Baseline assessments will be performed prior to dosing.

Subjects will be randomized as described herein to receive: (a) Study Drug; or (b) placebo or (c) teprotumumab—i.e., the study may be designed with two arms to compare Study Drug to either placebo or teprotumumab, or may be designed with three arms to compare Study Drug, placebo, and teprotumumab. Study Drug will be given as described herein. Teprotumumab Infusion: Infusions will take place on Day 1 (Baseline), and per marketed dosing thereafter. Placebo administration will match that of Study Drug or teprotumumab as appropriate.

Phone (email) contact for safety—day after infusion: Phone (or email) contact by research staff focusing on safety and tolerability aspects will be made the day after infusion for the first and second infusions (Day 1/Baseline and Day 3), and thereafter as deemed appropriate. In addition, subjects who experience an infusion-associated event after any subsequent infusion will also be contacted by phone (or email) by research staff the day after the infusion, and thereafter as deemed appropriate.

Efficacy Assessments

Clinical Activity Score (CAS): CAS will be obtained from each subject at Screening, Day 1/Baseline, and throughout the study, e.g. for a 24-week treatment period, Week 12/Month 3, and Week 24/Month 6. For patients entering a chronic/inactive study, CAS must be ≤1 in both eyes at the Screening and Baseline visits.

Clinical Measures of Severity—includes proptosis and diplopia: Clinical measures of severity will be obtained at Screening; at Day 1/Baseline, and throughout the study, e.g. for a 24-week treatment period, Week 3, Week 6, Week 12/Month 3, Week 18, and Week 24/Month 6 of the Treatment Period; and Week 30 of the Follow-up Period.

Subjects who have a ≥2 mm decrease in proptosis in the study eye from Screening are not eligible for randomization.

Pretibial myxedema (PTM) assessment: PTM assessment may optionally be performed at Day 1/Baseline and throughout the study, e.g. for a 24-week treatment period, Week 12/Month 3, and Week 24/Month 6.

Orbital pain by 10 cm visual analog scale: Orbital pain may be assessed on Day 1/Baseline and throughout the study, e.g. for a 24-week treatment period, Week 3, Week 6, Week 12/Month 3, Week 18, and Week 24/Month 6.

Safety Assessments

Pregnancy test: Pregnancy tests will be administered at all visits. Serum pregnancy test at Screening and Week 48 (or 6 months after last infusion if withdrawn early from treatment). Urine pregnancy tests prior to dosing at all other visits, as applicable. Perform for female subjects of childbearing potential (including those with an onset of menopause <2 years prior to Screening, non-therapy-induced amenorrhea for <12 months prior to Screening, or not surgically sterile [absence of ovaries and/or uterus]).

Ophthalmic exam: Ophthalmic exam will be performed at Screening, Day 1/Baseline, and throughout the study, e.g. for a 24-week treatment period, Week 6, Week 12/Month 3, Week 18, and Week 24/Month 6.

Best corrected visual acuity, pupil exam, color vision assessment, Ishihara color plates (or equivalent) or related red desaturation, intraocular pressure, and slit lamp exam. If significant abnormalities are noted compared to previous visits, including a loss of 2 lines or more of vision, development of pupil abnormalities including afferent pupillary defect, rise in intraocular pressure, development of corneal infiltrates or other abnormalities not here specified but of concern to the ophthalmologist, further investigations of visual function will be conducted according to the ophthalmologist decision.

Subjects who have decreased best-corrected visual acuity due to optic neuropathy (defined by a decrease in vision of 2 lines on the Snellen chart, new visual field defect, or color defect secondary to optic nerve involvement within the last 6 months) are not eligible for randomization.

Vital signs: Vital signs (blood pressure, heart rate, respiratory rate, temperature) will be measured at all clinic visits. Vital signs will be measured pre- and post-dose on Day 1, and pre-dose on other dose/infusion days. Additional vital signs will be monitored if infusion-associated AEs occur.

12-Lead ECG: Electrocardiogram (ECG) will be performed at Screening, Day 1/Baseline, and throughout the study, e.g. for a 24-week treatment period, Week 3, Week 6, Week 12/Month 3, and Week 24/Month 6.

Clinical Laboratory Tests

Chemistry: Chemistry may be assessed at Screening, Day 1/Baseline, and throughout the study, e.g. for a 24-week treatment period, Week 3, Week 6, Week 12/Month 3, Week 18, Week 24/Month 6, Week 30, and Week 36.

Thyroid (FT3, FT4, THS): Thyroid levels may be assessed at Screening, Day 1/Baseline, and throughout the study, e.g. for a 24-week treatment period, Week 3, Week 6, Week 12/Month 3, Week 18, Week 24/Month 6, Week 30, and Week 36. Subjects must be euthyroid with the baseline disease under control or have mild hypo- or hyperthyroidism (defined as FT4 and FT3 levels<50% above or below the normal limits). Every effort should be made to correct the mild hypo- or hyperthyroidism promptly and to maintain the euthyroid state for the full duration of the clinical trial.

Hematology: Hematology may be assessed at Screening, Day 1/Baseline, and throughout the study, e.g. for a 24-week treatment period, Week 3, Week 6, Week 12/Month 3, Week 18, Week 24/Month 6, Week 30, and Week 36.

HbA1c: HbA1c levels may be assessed at Screening, and throughout the study, e.g. for a 24-week treatment period, Week 12/Month 3, and Week 24/Month 6. HbA1c must be ≤8.0% for randomization. If the HbA1c is elevated and considered clinically significant at any time point after Screening, it will be repeated approximately every 90 days until it returns to normal or baseline value.

ADA/Nab samples: Anti-drug antibody (ADA)/neutralizing antibody (Nab) levels may be obtained on Day 1/Baseline, and throughout the study, e.g. for a 24-week treatment period, Week 3, Week 12/Month 3, and Week 24/Month 6. If a sample is positive in the ADA test, after confirmatory and reactive titer testing, the sample will then be tested for NAb. If the subject tests positive for NAb, he/she may be followed until levels either revert to Baseline or the subject's value decreases or remains stable. Any subject with a positive NAb test at the end of the Treatment Period (or PW) may continue to be followed until the subject's value decreases or remains stable.

AE/SAE Assessment: AEs/SAEs will be assessed periodically, up to and including at every visit. AEs that occur within 2 weeks prior to Day 1 and prior to dosing on Day 1 will be considered baseline signs/symptoms. AEs occurring or worsening after the dose on Day 1 through the end of the Treatment Period will be considered treatment-emergent AEs (TEAEs). AEs occurring or worsening during the Follow-Up Period will be considered post-dose AEs. All SAEs that occur from the signing of informed consent through 30 days after study discontinuation will be recorded.

Concomitant medications: Concomitant medications will be assessed periodically, up to and including at every visit.

Graves' Ophthalmopathy Quality of Life (GO-QoL) Questionnaire: GO-QoL may be assessed at Day 1/Baseline, and periodically throughout the study, e.g. for a 24-week treatment period, Week 6, Week 12/Month 3, and Week 24/Month 6.

PK Samples: PK samples may be collected prior to, and at the end of, the dosing or infusion on Day 1, and periodically throughout the study, e.g. for a 24-week treatment period, Week 3 and Week 12/Month 3 of the Treatment Period, and a single sample may be collected at the end of the Treatment Period. PK samples will not be collected for subjects who prematurely discontinue from the Treatment Period.

Biomarker Samples: Biomarker samples may be collected on Day 1 and throughout the study, e.g. for a 24-week treatment period, Week 3 and Week 12/Month 3 of the Treatment Period, and a single sample may be collected at the end of the Treatment Period.

Magnetic Resonance Imaging (MRI): Subjects may undergo MRI on Day 1 and at the visit at the end of the Treatment Period.

Randomization and Masking the Trial

The randomized trial is designed to assess efficacy and safety. For a study of chronic/inactive TED, patients will be randomly assigned in the (optionally) double-masked Treatment Period to one of three treatment groups in, e.g., a 1:1, 2:1, or 3:1 ratio in blocks of two, stratified by duration of chronic/inactive disease, ≤2 years or >2 years.

Study pharmacists who are aware of the trial-group assignments may prepare masked doses and/or infusions if needed. The on-site principal investigators will identify a patient's intervention or Treatment Group (Study Drug, active control, or placebo) only in the case of an emergency.

Calculation of Clinical Activity Score (CAS)

The clinical activity score consists of seven components: spontaneous retrobulbar pain, pain on attempted eye movements (upward, side-to-side, and downward gazes), conjunctival redness, redness of the eyelids, chemosis, swelling of the caruncle/plica, and swelling of the eyelids. Each component will be scored as present or absent, 1 or 0. The score at each efficacy assessment will be the sum of all items present to give a range of 0-γ, where 0 or 1 constitutes inactive disease and 7 constitutes severe active ophthalmopathy. A change of ≥2 points will be considered clinically meaningful, as would achievement of a CAS score of 0 or 1 in patients with acute/active disease.

Evaluation of Graves' Ophthalmopathy Quality of Life (GO-QoL)

Quality of life will be evaluated with the use of the GO quality of life questionnaire. The questionnaire has two self-assessment subscales; one covering impact of visual function on daily activities, the other assesses the impact of self-perceived appearance. The visual function subscale covers activities such as driving, walking outdoors, reading, watching television, etc. The appearance subscale asks the subject questions such as whether ophthalmopathy has altered the subject's appearance, caused other people to have a negative reaction to the subject, caused social isolation, and caused the subject to try to mask his or her appearance. Each subscale has 8 questions which are answered with: yes—very much so; yes—a little; or no—not at all. Each question is scored 0-2, respectively, and the total raw score is then mathematically transformed to a 0-100 scale, where 0 represents the most negative impact on quality of life, and 100 represents no impact. A change of ≥8 points on the 0-100 scale has been shown to be clinically meaningful. The combined score takes raw scores from both subscales and again transforms them to a single 0-100 scale.

Assessment of Gorman Grading of Diplopia

The Gorman assessment of subjective diplopia includes four categories: no diplopia (absent), diplopia when the patient is tired or awakening (intermittent), diplopia at extremes of gaze (inconstant), and continuous diplopia in the primary or reading position (constant). Patients are scored according to which grade of diplopia they are experiencing. An improvement of ≥1 grade is considered clinically meaningful.

Electrocardiogram

A 12-lead ECG may be performed as described in the Schedule of Events (Table 2) for all subjects or at the discretion of the Investigator. When a subject experiences an AE suspected to be an IR, a 12-lead ECG may also be performed.

Single 12-lead ECG recordings may be made at Screening, Baseline (Day 1), and periodically throughout the study, e.g. for a 24-week treatment period, Week 3, Week 6, Week 12/Month 3, and Week 24/Month 6, after the subject has been in the supine position for at least 5 minutes. A single repeat measurement is permitted at Screening for eligibility determination. Measurements of the following intervals may be recorded and reported: RR interval, PR interval, QRS width, QT interval, and QTcF. Assessments should include comments on clinical significance, whether the tracings are normal or abnormal; rhythm; presence of arrhythmia or conduction defects; morphology; any evidence of myocardial infarction; or ST-segment, T-Wave, and U-Wave abnormalities.

Clinical Laboratory Safety Tests

Blood (for hematology, clinical chemistry, thyroid measurements) may be collected at Screening; at Day 1, and periodically throughout the study, e.g. for a 24-week treatment period, Week 3, Week 6, Week 12/Month 3, Week 18, and Week 24/Month 6 of the Treatment Period, and Week 30 and Week 36 of the Follow-up Period.

HbA1c may be measured at Screening and periodically throughout the study, e.g. for a 24-week treatment period, Week 12/Month 3 of the Treatment Period, and Week 24/Month 6 of the Follow-up Period. HbA1c must be ≤8.0% for randomization. If the HbA1c is elevated and considered clinically significant at any time point after Screening, it will be repeated approximately every 90 days until it returns to normal or baseline value.

Anti-drug antibodies (ADA)/neutralizing antibodies (Nab) may be measured at Day 1, and periodically throughout the study, e.g. for a 24-week treatment period, Week 3, Week 12/Month 3, and Week 24/Month 6 of the Treatment Period. If a sample is positive in the ADA test, after confirmatory and reactive titer testing, the sample will then be tested for NAb. If the subject tests positive for NAb, he/she may be followed until levels either revert to Baseline or the subject's value decreases or remains stable. Any subject with a positive NAb test at the end of the Treatment Period (or PW) may continue to be followed until the subject's value decreases or remains stable.

Safety laboratory assessments may include:

Pregnancy Test: Serum pregnancy test at Screening and Week 48 (or 6 months after last dose or infusion). Urine pregnancy tests prior to dosing at all other visits, as applicable. Perform for female subjects of childbearing potential (including those with an onset of menopause <2 years prior to Screening, non-therapy-induced amenorrhea for <12 months prior to Screening, or not surgically sterile [absence of ovaries and/or uterus]).

Ophthalmic exam: best corrected visual acuity, pupil exam, color vision assessment, Ishihara color plates (or equivalent) or related red desaturation, intraocular pressure, and slit lamp exam. If significant abnormalities are noted compared to previous visits, including a loss of 2 lines or more of vision, development of pupil abnormalities including afferent pupillary defect, rise in intraocular pressure, development of corneal infiltrates or other abnormalities not here specified but of concern to the ophthalmologist, further investigations of visual function will be conducted according to the ophthalmologist decision Vital Signs: blood pressure, heart rate, respiratory rate, and temperature will be measured at all clinic visits. Vital signs will be measured pre- and post-infusion on Day 1 and Week 3, and pre-dose on all other infusion days. Additional vital signs will be monitored if infusion-associated AEs occur.

Outcomes of Trial

Patients who have a response may be defined as those who meet the primary end point at week 24. This end point may comprise a reduction of 2 mm or more in proptosis in the study eye in the absence of a corresponding amount of worsening in the non-study eye, or average or median change from baseline in proptosis, or a reduction in diplopia of ≥1 grade in subjects with baseline diplopia>0. Secondary end points may include proptosis, diplopia, and the CAS (both measured as continuous variables over time), orbital pain, MDI and PVR for the inferior rectus, superior rectus, the medial rectus, lateral rectus and orbital fat, circumference of calf and area of the lesion in subjects with baseline PTM, inflammatory and fibrotic biomarkers, transcriptomics associated with IGF-1R inhibition, and assessment of the patient's quality of life with the use of the GO-QOL instrument (which includes two subscales that measure limitations in visual functioning and psychosocial functioning as a consequence of changed physical appearance). Patients may also be categorized according to their level of response. Safety will be assessed according to the incidence of adverse events, serious adverse events, and withdrawals due to adverse events.

RESULTS

It is expected that IGF-1R inhibitors described herein will, when tested as Study Drugs in a clinical study as disclosed herein for either acute/active or chronic/inactive TED, have efficacy in the outcome measures of TED described herein or as modified by one of skill in the art.

Table 2 below sets forth an example of a schedule of assessments assuming a 24-week Treatment Period and either using teprotumumab as an active control or mimicking it, i.e., dosing on a 3-week cycle by infusion. This table is presented as an example for illustrative purposes, and is not mean to be inconsistent with the guidance above. Those of skill in the art will understand how to modify such a schedule in the event of a different dosing schedule or route of administration ad might be expected with, e.g., a study of an orally bioavailable small molecule drug dosed QD and compared to placebo as opposed to active teprotumumab control.

TABLE 2

Schedule of Assessments

| | Screening[1] S1/S2/S3 | Treatment Period[2] | | | | | | | | | Follow-Up Period[3] | | | Follow-Up Contact |
|---|---|---|---|---|---|---|---|---|---|---|---|---|---|---|
| | Study Visit | | | | | | | | | | | | | |
| | | 1 | 2 | 3 | 4 | 5 | 6 | 7 | 8 | 9/PW1[4] | 10/PW2[5] | 11[6] | | 12[7] |
| | Week (W)/Month (M) | | | | | | | | | | | | | |
| | −28 days | Day 1[8] | W3 | W6 | W9 | W12/ M3 | W15 | W18 | W21 | W24/M6 | W30 | W36 visit | W36 contact | W48 |
| | Visit Window (± days) | | | | | | | | | | | | | |
| | | (±3) | (±3) | (±3) | (±3) | (±3) | (±3) | (±3) | (±3) | (±7) | (±7) | (±7) | (±7) | (±7) |
| Informed consent | X | | | | | | | | | | | | | |
| Review inc/exc criteria | X | X | | | | | | | | | | | | |
| Demographics | X | | | | | | | | | | | | | |
| Medical history[9] | X[10] | X | | | | | | | | | | | | |
| Weight[11] | X | | | | | X | | | | X | | | | |
| Randomization[12] | | X[8] | | | | | | | | | | | | |
| Teprotumumab, study drug, or placebo infusion | | X | X | X | X | X | X | X | X | | | | | |
| Phone (email) contact for safety - day after infusion[13] | | X | X | | | | | | | | | | | |
| Efficacy assessments | | | | | | | | | | | | | | |
| CAS[14] | X | X | | | | X | | | | X | | | | |
| Clinical Measures of Severity - includes proptosis and diplopia | X | X[15] | X | X | | X | | X | | X | X | | | |
| PTM assessment[16] | | X | | | | X | | | | X | | | | |
| Orbital pain by 10 cm visual analog scale | | X | X | X | | X | | X | | X | | | | |
| Safety assessments | | | | | | | | | | | | | | |
| Pregnancy test[17] | X | X | X | X | X | X | X | X | X | X | X | X | | X |
| Ophthalmic exam[18] | X[19] | X | | X | | X | | X | | X | | | | |
| Vital signs[20] | X | X[20] | X[20] | X | X | X | X | X | X | X | X | X | | |
| 12-Lead ECG | X | X | X | X | | X | | | | X | | | | |
| Clinical laboratory tests | | | | | | | | | | | | | | |
| Chemistry | X | X | X | X | | X | | X | | X | X | X | | |
| Thyroid (FT3, FT4, TSH)[21] | X | X | X | X | | X | | X | | X | X | X | | |
| Hematology | X | X | X | X | | X | | X | | X | X | X | | |
| HbA1c[22] | X | | | | | X | | | | X | | | | |
| ADA/NAb samples[23] | | X | X | | | X | | | | X[24] | | | | |
| AE, SAE assessment[25] | X | X | X | X | X | X | X | X | X | X | X | X | X | |
| Concomitant medications | X | X | X | X | X | X | X | X | X | X | X | X | | |
| GO-QoL Questionnaire | | X | | X | | X | | | | X | | | | |

TABLE 2-continued

Schedule of Assessments

| | Screening[1] S1/S2/S3 | Treatment Period[2] | | | | | | | | | Follow-Up Period[3] | | | Follow-Up Contact |
|---|---|---|---|---|---|---|---|---|---|---|---|---|---|---|
| | | Study Visit | | | | | | | | | | | | |
| | | 1 | 2 | 3 | 4 | 5 | 6 | 7 | 8 | 9/PW1[4] | 10/PW2[5] | 11[6] | | 12[7] |
| | | Week (W)/Month (M) | | | | | | | | | | | | |
| | −28 days | Day 1[8] | W3 | W6 | W9 | W12/ M3 | W15 | W18 | W21 | W24/M6 | W30 | W36 visit | W36 contact | W48 |
| | | Visit Window (± days) | | | | | | | | | | | | |
| | | (±3) | (±3) | (±3) | (±3) | (±3) | (±3) | (±3) | (±3) | (±7) | (±7) | (±7) | (±7) | (±7) |
| PK samples[26] | | X | X | | | X | | | | X[24] | | | | |
| Biomarker samples | | X | X | | | X | | | | X | | | | |
| MRI[27] | | X | | | | | | | | X | | | | |

ADA = anti-drug antibody;
AE = adverse event;
AESI = adverse event of special interest;
CAS = Clinical Activity Score;
ECG = electrocardiogram;
FT3 = free triiodothyronine;
FT4 = free thyroxine;
FU = Follow-Up;
GO-QoL = Graves' Ophthalmopathy Quality of Life Questionnaire;
HbA1c = glycated hemoglobin;
M = month;
MRI = magnetic resonance imaging;
NAb = neutralizing antibody;
PK = pharmacokinetic;
PTM = pretibial myxedema;
PW = premature withdrawal;
q3W = once every 3 weeks;
SAE = serious adverse event;
TEAE = treatment-emergent adverse event;
TED = thyroid eye disease;
TSH = thyroid stimulating hormone;
W = week.

Footnotes:

[1]Screening procedures can take place over more than 1 day/clinic visit provided consent is obtained first and all assessments are completed within the desginated window.

[2]Double-masked Treatment Period. Subjects who are proptosis non-responders at Week 24 are eligible to enroll in an open-label extension study in which all subjects will receive Study Drug (10 mg/kg for the first infusion and 20 mg/kg for the remaining 7 infusions).

[3]Proptosis responders and non-responders who choose not to enroll in the open-label extension study will participate in a 12-week Follow-Up Period.

[4]If a subject prematurely discontinues study drug during the Treatment Period, they will return for a clinic visit and undergo the Week 24 assessments, with the exception of the collection of blood samples for PK and ADA evaluations. Subjects will be encouraged to continue study participation in the Follow-Up Period.

[5] If a subject prematurely discontinues from the study between Week 24 and Week 30 of the Follow-Up Period, they will return for a clinic visit and undergo the Week 30 assessments prior to discharge.

[6]All subjects will be contacted via phone or email at Week 36, except subjects who have an ongoing SAE or AESI at the Week 30 visit. Subjects who have an ongoing SAE or AESI at the Week 30 visit will return to the clinic at Week 36.

[7]Woman of childbearing potential will be contacted via phone or email at Week 48 to inquire if they have missed a menstrual cycle and will return to the clinic for a serum pregnancy test if required.

[8]On Day 1 (Baseline), subjects will be randomized and receive the first dose of study drug; however, Baseline assessments will be performed prior to dosing.

[9]Medical history including thyroid disease history and treatment, TED history and treatment and tobacco use history.

[10]TED must be stable, chronic/inactive (not progressing, non-sight threatening but appreciable impact on daily life) with TED diagnosed >2 years, but no longer than 7 years prior to Screening.

[11]Dosing will be adjusted if there is a change in weight during the Treatment Period. The weight obtained at Week 12 can be used in dose calculations beginning at Week 12 or Week 15.

[12]Subjects will be randomized in a 1:1 ratio (stratified by duration of chronic/inactive disease) to receive either: a) Study Drug (10 mg/kg on Day 1 followed by 20 mg/kg q3W for the remianing 7 infusions) or b) placebo or teprotumumab (q3W for all 8 infusions).

[13]Phone (or email) contact by research staff focusing on safety and tolerability aspects will be made the day after infusion for the first and second infusions, and thereafter as deemed appropriate. In addition, subjects who experience an infusion-associated event after any subsequent infusion will also be contacted by phone (or email) by research staff the day after the infusion, and thereafter as deemed appropriate.

[14]CAS must be ≤1 in both eyes at the Screening and Baseline visits.

[15]Subjects who have a ≥2 mm decrease in proptosis in the study eye from Screening are not eligible for randomization.

[16]Assess for presence or absence of PTM on Day 1, Week 12, and Week 24. If present, measurements of calf and lesion will be taken.

[17]Serum pregnancy test at Screening and Week 48 (or 6 months after last infusion if withdrawn early from treatment). Urine pregnancy tests prior to dosing at all other visits, as applicable. Perform for female subjects of childbearing potential (including those with an onset of menopause <2 years prior to Screening, non-therapy-induced amenorrhea for <12 months prior to Screening, or not surgically sterile [absence of ovaries and/or uterus]).

[18]Ophthalmic exam: best corrected visual acuity, pupil exam, color vision assessment, Ishihara color plates (or equivalent) or related red desaturation, intraocular pressure, and slit lamp exam. If significant abnormalites are noted compared to previous visits, including a loss of 2 lines or more of vision, development of pupil abnormalities including afferent pupillary defect, rise in intraocular pressure, development of corneal infiltrates or other abnormalities not here specified but of concern to the ophthalmologist, further investigations of visual function will be conducted according to the ophthalmologist decision.

[19]Subjects who have decreased best-corrected visual acuity due to optic neuropathy (defined by a decrease in vision of 2 lines on the Snellen chart, new visual field defect, or color defect secondary to optic nerve involvement within the last 6 months) are not eligible for randomization.

[20]Vital signs (blood pressure, heart rate, respiratory rate, temperature) will be measured at all clinic visits. Vital signs will be measured pre- and post-infusion on Day 1 and Week 3, and pre-dose on all other infusion days. Additional vital signs will be monitored if infusion-associated AEs occur.

[21]Subjects must be euthyroid with the baseline disease under control or have mild hypo- or hyperthyroidism (defined as FT4 and FT3 levels <50% above or below the normal limits). Every effort should be made to correct the mild hypo- or hyperthyroidism promptly and to maintain the euthyroid state for the full duration of the clinical trial.

[22]HbA1c must be ≤8.0% for randomization. If the Hb1Ac is elevated and considered clinically significant at any time point after Screening, it will be repeated approximately every 90 days until it returns to normal or baseline value.

[23]If a sample is positive in the ADA test, after confirmatory and reactive titer testing, the sample will then be tested for NAb. If the subject tests positive for NAb, he/she may be followed until levels either revert to Baseline or the subject's value decreases or remains stable. Any subject with a positive NAb test at Week 24 (or PW) may continue to be followed until the subject's value decreases or remains stable.

[24]Not collected for subjects who prematurely discontinue from the Treatment Period.

[25]AEs that occur within 2 weeks prior to Day 1 and prior to dosing on Day 1 will be considered baseline signs/symptoms. AEs occurring or worsening after the dose on Day 1 through the end of the Treatment Period will be considered treatment-emergent AWs (TEAEs). AEs occurring or worsening during the Follow-Up Period will be considered postdose AEs. All SAEs that occur from the signing of informed consent through 30 days after study discontinuation will be recorded.

TABLE 2-continued

Schedule of Assessments

| Screening[1] S1/S2/S3 | Treatment Period[2] | | | | | | | | | Follow-Up Period[3] | | | Follow-Up Contact |
|---|---|---|---|---|---|---|---|---|---|---|---|---|---|
| | Study Visit | | | | | | | | | | | | |
| | 1 | 2 | 3 | 4 | 5 | 6 | 7 | 8 | 9/PW1[4] | 10/PW2[5] | 11[6] | | 12[7] |
| | Week (W)/Month (M) | | | | | | | | | | | | |
| −28 days | Day 1[8] | W3 | W6 | W9 | W12/ M3 | W15 | W18 | W21 | W24/M6 | W30 | W36 visit | W36 contact | W48 |
| | Visit Window (± days) | | | | | | | | | | | | |
| | (±3) | (±3) | (±3) | (±3) | (±3) | (±3) | (±3) | (±3) | (±7) | (±7) | (±7) | (±7) | (±7) |

[26]PK samples will be collected prior to, and at the end of, the infusion on Day 1 and Weeks 3 and 12 of the Treatment Period and a single sample will be collected at Week 24.

[27]Subjects at one clinical investigative site will undergo MRI on Day 1 and at the Week 24 visit.

Example 32

Half-Life Extended AVE1642

The AVE1642 monoclonal antibody (humanized form of murine antibody EM164) is described in Example 4. A half-life extended version, using amino acid substitutions in the Fc portion of the antibody (i.e., an Fc variant), can also be used for the treatment of TED, as described in Example 31.

For instance, an AVE1642 humanized monoclonal antibody with an HCDR1 comprising SYWMH (SEQ ID NO:25), an HCDR2 comprising EINPSNGRTN (SEQ ID NO:76), an HCDR3 comprising GRPDYYGSSKWYFDV (SEQ ID NO:27), an LCDR1 comprising RSSQ-SIVHSNVNTYLE (SEQ ID NO:28), an LCDR2 comprising KVSNRFS (SEQ ID NO:29), and an LCDR3 comprising FQGSHVPPT (SEQ ID NO:30), can further comprise a variant Fc region comprising mutations that substitute a methionine at position 428 with a leucine (Met428Leu) and substitute an asparagine at position 434 with a serine (Asn434Ser), wherein the amino acid substitution numbering is EU as in Kabat.

Such a half-life extended AVE1642 antibody, comprising M428L/N434S substitutions, would be expected to be effective at a reduced dose and/or frequency than similar antibodies described in Example 4 alone. For instance, treatment of a subject with TED and/or symptoms of proptosis and/or diplopia would be expected to be treated at a dose of about 1-5 mg/kg, or about 1-10 mg/kg, or about 1-20 mg/kg, or about 1-50 mg/kg. In some embodiments, treatment of TED with this half-life extended antibody would be expected to occur as described herein at a dose of 1 mg/kg, or 2 mg/kg, or 3 mg/kg, or 4 mg/kg, or 5 mg/kg, or 6 mg/kg, or 7 mg/kg, or 8 mg/kg, or 9 mg/kg, or 10 mg/kg.

Likewise, the AVE1642 half-life extended antibody comprising the above CDRs and M428L/N434S Fc variant would also be expected to be suitable for administration via intravenous (IV) or even subcutaneous (SC) injection.

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method of reducing proptosis in a subject with moderate-to-severe inactive/chronic thyroid eye disease (TED), comprising administering to the subject an effective amount of an insulin-like growth factor-I receptor (IGF-1R) inhibitor, wherein the IGF-1R inhibitor is an antibody that specifically binds to IGF-1R and inhibits the binding of IGF-I and IGF-II to IGF-1R, and wherein the subject with moderate-to-severe inactive/chronic TED has all of the following characteristics:

(i) an increase of ≥3 mm proptosis relative to the subject's value prior to diagnosis of TED or an increase of ≥3 mm proptosis above the normal values for the subject's race and gender;

(ii) a clinical activity score (CAS) of 0 or 1 in both eyes as determined by the seven-item scale; and (iii) no inflammatory symptoms for at least one year prior to administration of the antibody.

2. The method of claim 1, wherein the method reduces proptosis by at least 2 mm in the subject.

3. The method of claim 1, wherein the antibody is administered intravenously (IV) or subcutaneously (SC).

4. The method of claim 3, wherein the antibody is administered IV.

5. The method of claim 1, wherein said antibody is ganitumab, figitumumab, cixutumumab, dalotuzumab, robatumumab, AVE1642, BIIB022, or istiratumab.

6. The method of claim 1, wherein the method reduces proptosis by at least 3 mm in the subject.

7. The method of claim 1, wherein the method reduces proptosis by at least 4 mm in the subject.

8. The method of claim 1, wherein the antibody comprises a heavy chain variable domain comprising the sequence of SEQ ID NO: 78 and a light chain variable domain comprising the sequence of SEQ ID NO: 80.

9. The method of claim 1, wherein the antibody is teprotumumab.

10. The method of claim 9, wherein teprotumumab is administered intravenously at an initial dose of 10 mg/kg followed by doses of 20 mg/kg every three weeks.

11. The method of claim 1, wherein the subject with moderate-to-severe inactive/chronic TED has a CAS of 0 or 1 in both eyes as determined by the seven-item scale for at least one year prior to administration of the antibody.

12. The method of claim 1, wherein the subject with moderate-to-severe inactive/chronic TED has inconstant or constant diplopia.

13. The method of claim 1, wherein the antibody is AVE1642.

14. A method of reducing proptosis in a subject with moderate-to-severe inactive/chronic TED, comprising administering to the subject teprotumumab, wherein the subject with moderate-to-severe inactive/chronic TED has all of the following characteristics:

(i) an increase of ≥3 mm proptosis relative to the subject's value prior to diagnosis of TED or an increase of ≥3 mm proptosis above the normal values for the subject's race and gender;

(ii) a CAS of 0 or 1 in both eyes as determined by the seven-item scale; and (iii) no inflammatory symptoms for at least one year prior to administration of teprotumumab, wherein proptosis is reduced in the subject by at least 2 mm.

15. The method of claim 14, wherein proptosis is reduced in the subject by at least 3 mm.

16. The method of claim 14, wherein proptosis is reduced in the subject by at least 4 mm.

17. The method of claim 14, wherein teprotumumab is administered intravenously at an initial dose of 10 mg/kg followed by doses of 20 mg/kg every three weeks.

18. The method of claim 14, wherein the subject with moderate-to-severe inactive/chronic TED has a CAS of 0 or 1 in both eyes as determined by the seven-item scale for at least one year prior to administration of teprotumumab.

19. The method of claim 14, wherein the subject with moderate-to-severe inactive/chronic TED has inconstant or constant diplopia.

* * * * *

SEQUENCE LISTING

<160> NUMBER OF SEQ ID NOS: 95

<210> SEQ ID NO 1
<211> LENGTH: 6
<212> TYPE: PRT
<213> ORGANISM: Artificial Sequence
<220> FEATURE:
<223> OTHER INFORMATION: HCDR1 for Dalotuzumab

<400> SEQUENCE: 1

Gly Gly Tyr Leu Trp Asn
1 5

<210> SEQ ID NO 2
<211> LENGTH: 16
<212> TYPE: PRT
<213> ORGANISM: Artificial Sequence
<220> FEATURE:
<223> OTHER INFORMATION: HCDR2 for Dalotuzumab

<400> SEQUENCE: 2

Tyr Ile Ser Tyr Asp Gly Thr Asn Asn Tyr Lys Pro Ser Leu Lys Asp
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: HCDR3 for Dalotuzumab

<400> SEQUENCE: 3

Tyr Gly Arg Val Phe Phe Asp Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: LCDR1 for Dalotuzumab

<400> SEQUENCE: 4

Arg Ser Ser Gln Ser Ile Val His Ser Asn Gly Asn Thr Tyr Leu Gln
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: LCDR2 for Dalotuzumab

<400> SEQUENCE: 5

Lys Val Ser Asn Arg Leu Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3 for Dalotuzumab

<400> SEQUENCE: 6

Phe Gln Gly Ser His Val Pro Trp Thr
1               5

<210> SEQ ID NO 7
<211> LENGTH: 447
<212> TYPE: PRT
<213> ORGANISM: Artificial Sequence
<220> FEATURE:
<223> OTHER INFORMATION: Heavy Chain of Dalotuzumab

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Gly Gly
            20                  25                  30

Tyr Leu Trp Asn Trp Ile Arg Gln Pro Pro Gly Lys Gly Leu Glu Trp
        35                  40                  45

Ile Gly Tyr Ile Ser Tyr Asp Gly Thr Asn Asn Tyr Lys Pro Ser Leu
    50                  55                  60

-continued

Lys Asp Arg Val Thr Ile Ser Arg Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Tyr Gly Arg Val Phe Phe Asp Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 8
<211> LENGTH: 219
<212> TYPE: PRT
<213> ORGANISM: Artificial Sequence
<220> FEATURE:

<223> OTHER INFORMATION: Light Chain of Dalotuzumab

<400> SEQUENCE: 8

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Ile Val His Ser
20 25 30

Asn Gly Asn Thr Tyr Leu Gln Trp Tyr Leu Gln Lys Pro Gly Gln Ser
35 40 45

Pro Gln Leu Leu Ile Tyr Lys Val Ser Asn Arg Leu Tyr Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Trp Thr Phe Gly Gln Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 9
<211> LENGTH: 6
<212> TYPE: PRT
<213> ORGANISM: Artificial Sequence
<220> FEATURE:
<223> OTHER INFORMATION: HCDR1 of Ganitumab

<400> SEQUENCE: 9

Ser Ser Asn Trp Trp Ser
1 5

<210> SEQ ID NO 10
<211> LENGTH: 16
<212> TYPE: PRT
<213> ORGANISM: Artificial Sequence
<220> FEATURE:
<223> OTHER INFORMATION: HCDR2 of Ganitumab

<400> SEQUENCE: 10

Glu Ile Tyr His Ser Gly Ser Thr Asn Tyr Asn Pro Ser Leu Lys Ser
1 5 10 15

<210> SEQ ID NO 11
<211> LENGTH: 10
<212> TYPE: PRT
<213> ORGANISM: Artificial Sequence
<220> FEATURE:
<223> OTHER INFORMATION: HCDR3 of Ganitumab

<400> SEQUENCE: 11

Trp Thr Gly Arg Thr Asp Ala Phe Asp Ile
1 5 10

<210> SEQ ID NO 12
<211> LENGTH: 19
<212> TYPE: PRT
<213> ORGANISM: Artificial Sequence
<220> FEATURE:
<223> OTHER INFORMATION: LCDR1 of Ganitumab

<400> SEQUENCE: 12

Ile Ser Cys Arg Ser Ser Gln Ser Leu Leu His Ser Asn Gly Tyr Asn
1 5 10 15

Tyr Leu Asp

<210> SEQ ID NO 13
<211> LENGTH: 7
<212> TYPE: PRT
<213> ORGANISM: Artificial Sequence
<220> FEATURE:
<223> OTHER INFORMATION: LCDR2 for Ganitumab

<400> SEQUENCE: 13

Leu Gly Ser Asn Arg Ala Ser
1 5

<210> SEQ ID NO 14
<211> LENGTH: 9
<212> TYPE: PRT
<213> ORGANISM: Artificial Sequence
<220> FEATURE:
<223> OTHER INFORMATION: LCDR3 of Ganitumab

<400> SEQUENCE: 14

Met Gln Gly Thr His Trp Pro Leu Thr
1 5

<210> SEQ ID NO 15
<211> LENGTH: 448
<212> TYPE: PRT
<213> ORGANISM: Artificial Sequence
<220> FEATURE:
<223> OTHER INFORMATION: Heavy Chain of Ganitumab

<400> SEQUENCE: 15

Gln Val Gln Leu Gln Glu Ser Gly Pro Gly Leu Val Lys Pro Ser Gly
1 5 10 15

Thr Leu Ser Leu Thr Cys Ala Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ser Val Asp Lys Ser Lys Asn Gln Phe Ser Leu
65 70 75 80

Lys Leu Ser Ser Val Thr Ala Ala Asp Thr Ala Val Tyr Tyr Cys Ala
85 90 95

Arg Trp Thr Gly Arg Thr Asp Ala Phe Asp Ile Trp Gly Gln Gly Thr
100 105 110

Met Val Thr Val Ser Ser Ala Ser Thr Lys Gly Pro Ser Val Phe Pro 115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 16
<211> LENGTH: 219
<212> TYPE: PRT
<213> ORGANISM: Artificial Sequence
<220> FEATURE:
<223> OTHER INFORMATION: Light Chain of Ganitumab

<400> SEQUENCE: 16

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser

```
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 17
<211> LENGTH: 5
<212> TYPE: PRT
<213> ORGANISM: Artificial Sequence
<220> FEATURE:
<223> OTHER INFORMATION: HCDR1 of Xentuzumab

<400> SEQUENCE: 17

Ser Tyr Trp Met Ser
1               5


<210> SEQ ID NO 18
<211> LENGTH: 15
<212> TYPE: PRT
<213> ORGANISM: Artificial Sequence
<220> FEATURE:
<223> OTHER INFORMATION: HCDR2 of Xentuzumab

<400> SEQUENCE: 18

Ser Ile Thr Ser Tyr Gly Ser Phe Thr Tyr Ala Asp Ser Val Lys
1               5                   10                  15


<210> SEQ ID NO 19
<211> LENGTH: 8
<212> TYPE: PRT
<213> ORGANISM: Artificial Sequence
<220> FEATURE:
<223> OTHER INFORMATION: HCDR3 of Xentuzumab

<400> SEQUENCE: 19

Asn Met Tyr Thr His Phe Asp Ser
1               5


<210> SEQ ID NO 20
<211> LENGTH: 13
<212> TYPE: PRT
<213> ORGANISM: Artificial Sequence
```

```
<220> FEATURE:
<223> OTHER INFORMATION: LCDR1 of Xentuzumab

<400> SEQUENCE: 20

Ser Gly Ser Ser Ser Asn Ile Gly Ser Asn Ser Val Ser
1               5                   10


<210> SEQ ID NO 21
<211> LENGTH: 7
<212> TYPE: PRT
<213> ORGANISM: Artificial Sequence
<220> FEATURE:
<223> OTHER INFORMATION: LCDR2 of Xentuzumab

<400> SEQUENCE: 21

Asp Asn Ser Lys Arg Pro Ser
1               5


<210> SEQ ID NO 22
<211> LENGTH: 11
<212> TYPE: PRT
<213> ORGANISM: Artificial Sequence
<220> FEATURE:
<223> OTHER INFORMATION: LCDR3 of Xentuzumab

<400> SEQUENCE: 22

Gln Ser Arg Asp Thr Tyr Gly Tyr Tyr Trp Val
1               5                   10


<210> SEQ ID NO 23
<211> LENGTH: 400
<212> TYPE: PRT
<213> ORGANISM: Artificial Sequence
<220> FEATURE:
<223> OTHER INFORMATION: Heavy Chain of Xentuzumab

<400> SEQUENCE: 23

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Trp Met Ser Trp Val Arg Gln Ala Pro Gly Lys Gly Leu Glu Leu Val
        35                  40                  45

Ser Ser Ile Thr Ser Tyr Gly Ser Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Met Tyr Thr His Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400


<210> SEQ ID NO 24
<211> LENGTH: 216
<212> TYPE: PRT
<213> ORGANISM: Artificial Sequence
<220> FEATURE:
<223> OTHER INFORMATION: Light Chain of Xentuzumab

<400> SEQUENCE: 24

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Asp Asn Ser Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Arg Asp Thr Tyr Gly
                85                  90                  95

Tyr Tyr Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Gly Asp Ser Ser Pro Val Lys
145                 150                 155                 160
```

```
Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 25
<211> LENGTH: 5
<212> TYPE: PRT
<213> ORGANISM: Artificial Sequence
<220> FEATURE:
<223> OTHER INFORMATION: HCDR1 of AVE1642

<400> SEQUENCE: 25

Ser Tyr Trp Met His
1               5


<210> SEQ ID NO 26
<211> LENGTH: 17
<212> TYPE: PRT
<213> ORGANISM: Artificial Sequence
<220> FEATURE:
<223> OTHER INFORMATION: HCDR2 of AVE1642

<400> SEQUENCE: 26

Glu Ile Asn Pro Ser Asn Gly Arg Thr Asn Tyr Asn Glu Lys Phe Lys
1               5                   10                  15

Arg


<210> SEQ ID NO 27
<211> LENGTH: 15
<212> TYPE: PRT
<213> ORGANISM: Artificial Sequence
<220> FEATURE:
<223> OTHER INFORMATION: HCDR3 of AVE1642

<400> SEQUENCE: 27

Gly Arg Pro Asp Tyr Tyr Gly Ser Ser Lys Trp Tyr Phe Asp Val
1               5                   10                  15


<210> SEQ ID NO 28
<211> LENGTH: 16
<212> TYPE: PRT
<213> ORGANISM: Artificial Sequence
<220> FEATURE:
<223> OTHER INFORMATION: LCDR1 of AVE1642

<400> SEQUENCE: 28

Arg Ser Ser Gln Ser Ile Val His Ser Asn Val Asn Thr Tyr Leu Glu
1               5                   10                  15


<210> SEQ ID NO 29
<211> LENGTH: 7
<212> TYPE: PRT
<213> ORGANISM: Artificial Sequence
<220> FEATURE:
<223> OTHER INFORMATION: LCDR2 of AVE1642

<400> SEQUENCE: 29

Lys Val Ser Asn Arg Phe Ser
1               5
```

<210> SEQ ID NO 30
<211> LENGTH: 9
<212> TYPE: PRT
<213> ORGANISM: Artificial Sequence
<220> FEATURE:
<223> OTHER INFORMATION: LCDR3 of AVE1642

<400> SEQUENCE: 30

Phe Gln Gly Ser His Val Pro Pro Thr
1               5

<210> SEQ ID NO 31
<211> LENGTH: 124
<212> TYPE: PRT
<213> ORGANISM: Artificial Sequence
<220> FEATURE:
<223> OTHER INFORMATION: Heavy Chain ofAVE1642

<400> SEQUENCE: 31

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Arg Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Ala Gly Thr Thr Val Thr Val Ser Ser
        115                 120

<210> SEQ ID NO 32
<211> LENGTH: 113
<212> TYPE: PRT
<213> ORGANISM: Artificial Sequence
<220> FEATURE:
<223> OTHER INFORMATION: Light Chain of AVE1642

<400> SEQUENCE: 32

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 33
<211> LENGTH: 10
<212> TYPE: PRT
<213> ORGANISM: Artificial Sequence
<220> FEATURE:
<223> OTHER INFORMATION: HCDR1 of Figitumumab

<400> SEQUENCE: 33

Gly Phe Thr Phe Ser Ser Tyr Ala Met Asn
1 5 10

<210> SEQ ID NO 34
<211> LENGTH: 17
<212> TYPE: PRT
<213> ORGANISM: Artificial Sequence
<220> FEATURE:
<223> OTHER INFORMATION: HCDR2 of Figitumumab

<400> SEQUENCE: 34

Ala Ile Ser Gly Ser Gly Gly Thr Thr Phe Tyr Ala Asp Ser Val Lys
1 5 10 15

Gly

<210> SEQ ID NO 35
<211> LENGTH: 16
<212> TYPE: PRT
<213> ORGANISM: Artificial Sequence
<220> FEATURE:
<223> OTHER INFORMATION: HCDR3 of Figitumumab

<400> SEQUENCE: 35

Asp Leu Gly Trp Ser Asp Ser Tyr Tyr Tyr Tyr Tyr Gly Met Asp Val
1 5 10 15

<210> SEQ ID NO 36
<211> LENGTH: 11
<212> TYPE: PRT
<213> ORGANISM: Artificial Sequence
<220> FEATURE:
<223> OTHER INFORMATION: LCDR1 of Figitumumab

<400> SEQUENCE: 36

Arg Ala Ser Gln Gly Ile Arg Asn Asp Leu Gly
1 5 10

<210> SEQ ID NO 37
<211> LENGTH: 7
<212> TYPE: PRT
<213> ORGANISM: Artificial Sequence
<220> FEATURE:
<223> OTHER INFORMATION: LCDR2 of Figitumumab

<400> SEQUENCE: 37

Ala Ala Ser Arg Leu His Arg
1 5

<210> SEQ ID NO 38
<211> LENGTH: 9
<212> TYPE: PRT
<213> ORGANISM: Artificial Sequence
<220> FEATURE:
<223> OTHER INFORMATION: LCDR3 of Figitumumab

<400> SEQUENCE: 38

```
Leu Gln His Asn Ser Tyr Pro Cys Ser
1               5


<210> SEQ ID NO 39
<211> LENGTH: 451
<212> TYPE: PRT
<213> ORGANISM: Artificial Sequence
<220> FEATURE:
<223> OTHER INFORMATION: Heavy Chain of Figitumumab

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Thr Thr Phe Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Trp Ser Asp Ser Tyr Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350
```

```
Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 40
<211> LENGTH: 214
<212> TYPE: PRT
<213> ORGANISM: Artificial Sequence
<220> FEATURE:
<223> OTHER INFORMATION: Light Chain of Figitumumab

<400> SEQUENCE: 40

Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 41
<211> LENGTH: 5
<212> TYPE: PRT
<213> ORGANISM: Artificial Sequence
<220> FEATURE:
```

<223> OTHER INFORMATION: HCDR1 of Dusigitumab

<400> SEQUENCE: 41

Ser Tyr Asp Ile Asn
1 5

<210> SEQ ID NO 42
<211> LENGTH: 17
<212> TYPE: PRT
<213> ORGANISM: Artificial Sequence
<220> FEATURE:
<223> OTHER INFORMATION: HCDR2 of Dusigitumab

<400> SEQUENCE: 42

Trp Met Asn Pro Asn Ser Gly Asn Thr Gly Tyr Ala Gln Lys Phe Gln
1 5 10 15

Gly

<210> SEQ ID NO 43
<211> LENGTH: 11
<212> TYPE: PRT
<213> ORGANISM: Artificial Sequence
<220> FEATURE:
<223> OTHER INFORMATION: HCDR3 of Dusigitumab

<400> SEQUENCE: 43

Asp Pro Tyr Tyr Tyr Tyr Tyr Gly Met Asp Val
1 5 10

<210> SEQ ID NO 44
<211> LENGTH: 13
<212> TYPE: PRT
<213> ORGANISM: Artificial Sequence
<220> FEATURE:
<223> OTHER INFORMATION: LCDR1 of Dusigitumab

<400> SEQUENCE: 44

Ser Gly Ser Ser Ser Asn Ile Glu Asn Asn His Val Ser
1 5 10

<210> SEQ ID NO 45
<211> LENGTH: 7
<212> TYPE: PRT
<213> ORGANISM: Artificial Sequence
<220> FEATURE:
<223> OTHER INFORMATION: LCDR2 of Dusigitumab

<400> SEQUENCE: 45

Asp Asn Asn Lys Arg Pro Ser
1 5

<210> SEQ ID NO 46
<211> LENGTH: 12
<212> TYPE: PRT
<213> ORGANISM: Artificial Sequence
<220> FEATURE:
<223> OTHER INFORMATION: LCDR3 of Dusigitumab

<400> SEQUENCE: 46

Glu Thr Trp Asp Thr Ser Leu Ser Ala Gly Arg Val
1 5 10

<210> SEQ ID NO 47
<211> LENGTH: 446
<212> TYPE: PRT
<213> ORGANISM: Artificial Sequence
<220> FEATURE:
<223> OTHER INFORMATION: Heavy Chain of Dusigitumab

<400> SEQUENCE: 47

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Tyr Tyr Tyr Tyr Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 48
<211> LENGTH: 217
<212> TYPE: PRT
<213> ORGANISM: Artificial Sequence
<220> FEATURE:
<223> OTHER INFORMATION: Light Chain of Dusigitumab

<400> SEQUENCE: 48

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Glu Asn Asn
            20                  25                  30

His Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Thr Ser Leu
                85                  90                  95

Ser Ala Gly Arg Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 49
<211> LENGTH: 5
<212> TYPE: PRT
<213> ORGANISM: Artificial Sequence
<220> FEATURE:
<223> OTHER INFORMATION: HCDR1 of Cixutumumab

<400> SEQUENCE: 49

Ser Tyr Ala Ile Ser
1               5


<210> SEQ ID NO 50
<211> LENGTH: 16
<212> TYPE: PRT
```

-continued

```
<213> ORGANISM: Artificial Sequence
<220> FEATURE:
<223> OTHER INFORMATION: HCDR2 of Cixutumumab

<400> SEQUENCE: 50

Gly Ile Ile Pro Ile Phe Gly Thr Ala Asn Tyr Ala Gln Lys Phe Gln
1               5                   10                  15


<210> SEQ ID NO 51
<211> LENGTH: 21
<212> TYPE: PRT
<213> ORGANISM: Artificial Sequence
<220> FEATURE:
<223> OTHER INFORMATION: HCDR3 of Cixutumumab

<400> SEQUENCE: 51

Ala Pro Leu Arg Phe Leu Glu Trp Ser Thr Gln Asp His Tyr Tyr Tyr
1               5                   10                  15

Tyr Tyr Met Asp Val
            20


<210> SEQ ID NO 52
<211> LENGTH: 11
<212> TYPE: PRT
<213> ORGANISM: Artificial Sequence
<220> FEATURE:
<223> OTHER INFORMATION: LCDR1 of Cixutumumab

<400> SEQUENCE: 52

Gln Gly Asp Ser Leu Arg Ser Tyr Tyr Ala Thr
1               5                   10


<210> SEQ ID NO 53
<211> LENGTH: 7
<212> TYPE: PRT
<213> ORGANISM: Artificial Sequence
<220> FEATURE:
<223> OTHER INFORMATION: LCDR2 of Cixutumumab

<400> SEQUENCE: 53

Gly Glu Asn Lys Arg Pro Ser
1               5


<210> SEQ ID NO 54
<211> LENGTH: 11
<212> TYPE: PRT
<213> ORGANISM: Artificial Sequence
<220> FEATURE:
<223> OTHER INFORMATION: LCDR3 of Cixutumumab

<400> SEQUENCE: 54

Lys Ser Arg Asp Gly Ser Gly Gln His Leu Val
1               5                   10


<210> SEQ ID NO 55
<211> LENGTH: 460
<212> TYPE: PRT
<213> ORGANISM: Artificial Sequence
<220> FEATURE:
<223> OTHER INFORMATION: Heavy Chain of Cixutumumab

<400> SEQUENCE: 55

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

-continued

```
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445
```

Tyr Thr Gln Lys Ser Leu Ser Leu Ser Pro Gly Lys
    450                 455                 460

<210> SEQ ID NO 56
<211> LENGTH: 214
<212> TYPE: PRT
<213> ORGANISM: Artificial Sequence
<220> FEATURE:
<223> OTHER INFORMATION: Light Chain of Cixutumumab

<400> SEQUENCE: 56

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Ala Glu Cys Ser
    210

<210> SEQ ID NO 57
<211> LENGTH: 5
<212> TYPE: PRT
<213> ORGANISM: Artificial Sequence
<220> FEATURE:
<223> OTHER INFORMATION: HCDR1 of BIIB022

<400> SEQUENCE: 57

Ile Tyr Arg Met Gln
1               5

<210> SEQ ID NO 58
<211> LENGTH: 17
<212> TYPE: PRT
<213> ORGANISM: Artificial Sequence
<220> FEATURE:
<223> OTHER INFORMATION: HCDR2 of BIIB022

<400> SEQUENCE: 58

Gly Ile Ser Pro Ser Gly Gly Thr Thr Trp Tyr Ala Asp Ser Val Lys

```
1               5                   10                  15

Gly


<210> SEQ ID NO 59
<211> LENGTH: 11
<212> TYPE: PRT
<213> ORGANISM: Artificial Sequence
<220> FEATURE:
<223> OTHER INFORMATION: HCDR3 of BIIB022

<400> SEQUENCE: 59

Trp Ser Gly Gly Ser Gly Tyr Ala Phe Asp Ile
1               5                   10


<210> SEQ ID NO 60
<211> LENGTH: 10
<212> TYPE: PRT
<213> ORGANISM: Artificial Sequence
<220> FEATURE:
<223> OTHER INFORMATION: LCDR1 of BIIB022

<400> SEQUENCE: 60

Gln Ala Ser Arg Asp Ile Arg Asn Tyr Asn
1               5                   10


<210> SEQ ID NO 61
<211> LENGTH: 7
<212> TYPE: PRT
<213> ORGANISM: Artificial Sequence
<220> FEATURE:
<223> OTHER INFORMATION: LCDR2 of BIIB022

<400> SEQUENCE: 61

Asp Ala Ser Ser Leu Gln Thr
1               5


<210> SEQ ID NO 62
<211> LENGTH: 9
<212> TYPE: PRT
<213> ORGANISM: Artificial Sequence
<220> FEATURE:
<223> OTHER INFORMATION: LCDR3 of BIIB022

<400> SEQUENCE: 62

Gln Gln Phe Asp Ser Leu Pro His Thr
1               5


<210> SEQ ID NO 63
<211> LENGTH: 120
<212> TYPE: PRT
<213> ORGANISM: Artificial Sequence
<220> FEATURE:
<223> OTHER INFORMATION: Heavy Chain of BIIB022

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Arg Met Gln Trp Val Arg Gln Ala Pro Gly Lys Gly Leu Glu Trp Val
        35                  40                  45

Ser Gly Ile Ser Pro Ser Gly Gly Thr Thr Trp Tyr Ala Asp Ser Val
    50                  55                  60

Lys Gly Arg Phe Thr Ile Ser Arg Asp Asn Ser Lys Asn Thr Leu Tyr
```

65 70 75 80

Leu Gln Met Asn Ser Leu Arg Ala Glu Asp Thr Ala Val Tyr Tyr Cys
85 90 95

Ala Arg Trp Ser Gly Gly Ser Gly Tyr Ala Phe Asp Ile Trp Gly Gln
100 105 110

Gly Thr Met Val Thr Val Ser Ser
115 120

<210> SEQ ID NO 64
<211> LENGTH: 107
<212> TYPE: PRT
<213> ORGANISM: Artificial Sequence
<220> FEATURE:
<223> OTHER INFORMATION: Light Chain of BIIB022

<400> SEQUENCE: 64

Asp Ile Gln Met Thr Gln Ser Pro Leu Ser Leu Ser Ala Ser Val Gly
1 5 10 15

Asp Arg Val Thr Ile Thr Cys Gln Ala Ser Arg Asp Ile Arg Asn Tyr
20 25 30

Leu Asn Trp Tyr Gln Gln Lys Pro Gly Lys Ala Pro Lys Leu Leu Ile
35 40 45

Tyr Asp Ala Ser Ser Leu Gln Thr Gly Val Pro Ser Arg Phe Gly Gly
50 55 60

Ser Gly Ser Gly Thr Asp Phe Ser Phe Thr Ile Gly Ser Leu Gln Pro
65 70 75 80

Glu Asp Ile Ala Thr Tyr Tyr Cys Gln Gln Phe Asp Ser Leu Pro His
85 90 95

Thr Phe Gly Gln Gly Thr Lys Leu Glu Ile Lys
100 105

<210> SEQ ID NO 65
<211> LENGTH: 448
<212> TYPE: PRT
<213> ORGANISM: Artificial Sequence
<220> FEATURE:
<223> OTHER INFORMATION: HCDR1 of Robatumumab

<400> SEQUENCE: 65

Glu Val Gln Leu Val Gln Ser Gly Gly Gly Leu Val Lys Pro Gly Gly
1 5 10 15

Ser Leu Arg Leu Ser Cys Ala Ala Ser Gly Phe Thr Phe Ser Ser Phe
20 25 30

Ala Met His Trp Val Arg Gln Ala Pro Gly Lys Gly Leu Glu Trp Ile
35 40 45

Ser Val Ile Asp Thr Arg Gly Ala Thr Tyr Tyr Ala Asp Ser Val Lys
50 55 60

Gly Arg Phe Thr Ile Ser Arg Asp Asn Ala Lys Asn Ser Leu Tyr Leu
65 70 75 80

Gln Met Asn Ser Leu Arg Ala Glu Asp Thr Ala Val Tyr Tyr Cys Ala
85 90 95

Arg Leu Gly Asn Phe Tyr Tyr Gly Met Asp Val Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

-continued

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 66
<211> LENGTH: 214
<212> TYPE: PRT
<213> ORGANISM: Artificial Sequence
<220> FEATURE:
<223> OTHER INFORMATION: HCDR2 of Robatumumab

<400> SEQUENCE: 66

Glu Ile Val Leu Thr Gln Ser Pro Gly Thr Leu Ser Val Ser Pro Gly
1               5                   10                  15

Glu Arg Ala Thr Leu Ser Cys Arg Ala Ser Gln Ser Ile Gly Ser Ser
            20                  25                  30

Leu His Trp Tyr Gln Gln Lys Pro Gly Gln Ala Pro Arg Leu Leu Ile
        35                  40                  45

Lys Tyr Ala Ser Gln Ser Leu Ser Gly Ile Pro Asp Arg Phe Ser Gly
    50                  55                  60
```

-continued

```
Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Ser Ser Arg Leu Pro His
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 67
<211> LENGTH: 10
<212> TYPE: PRT
<213> ORGANISM: Artificial Sequence
<220> FEATURE:
<223> OTHER INFORMATION: HCDR1of Istiratumab

<400> SEQUENCE: 67

Gly Phe Met Phe Ser Arg Tyr Pro Met His
1               5                   10


<210> SEQ ID NO 68
<211> LENGTH: 16
<212> TYPE: PRT
<213> ORGANISM: Artificial Sequence
<220> FEATURE:
<223> OTHER INFORMATION: HCDR2 of Istiratumab

<400> SEQUENCE: 68

Ile Ser Gly Ser Gly Gly Ala Thr Pro Tyr Ala Asp Ser Val Lys Gly
1               5                   10                  15


<210> SEQ ID NO 69
<211> LENGTH: 13
<212> TYPE: PRT
<213> ORGANISM: Artificial Sequence
<220> FEATURE:
<223> OTHER INFORMATION: HCDR3 of Istiratumab

<400> SEQUENCE: 69

Asp Phe Tyr Gln Ile Leu Thr Gly Asn Ala Phe Asp Tyr
1               5                   10


<210> SEQ ID NO 70
<211> LENGTH: 11
<212> TYPE: PRT
<213> ORGANISM: Artificial Sequence
<220> FEATURE:
<223> OTHER INFORMATION: LCDR1 of Istiratumab

<400> SEQUENCE: 70
```

-continued

```
Arg Ala Ser Gln Gly Ile Ser Ser Tyr Leu Ala
1               5                   10


<210> SEQ ID NO 71
<211> LENGTH: 7
<212> TYPE: PRT
<213> ORGANISM: Artificial Sequence
<220> FEATURE:
<223> OTHER INFORMATION: LCDR2 of Istiratumab

<400> SEQUENCE: 71

Ala Lys Ser Thr Leu Gln Ser
1               5


<210> SEQ ID NO 72
<211> LENGTH: 9
<212> TYPE: PRT
<213> ORGANISM: Artificial Sequence
<220> FEATURE:
<223> OTHER INFORMATION: LCDR3 of Istiratumab

<400> SEQUENCE: 72

Gln Gln Tyr Trp Thr Phe Pro Leu Thr
1               5


<210> SEQ ID NO 73
<211> LENGTH: 720
<212> TYPE: PRT
<213> ORGANISM: Artificial Sequence
<220> FEATURE:
<223> OTHER INFORMATION: Heavy Chain  of Istiratumab

<400> SEQUENCE: 73

Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Pro Met His Trp Val Arg Gln Ala Pro Gly Lys Gly Leu Glu Trp Val
        35                  40                  45

Gly Ser Ile Ser Gly Ser Gly Gly Ala Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Tyr Gln Ile Leu Thr Gly Asn Ala Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
```

-continued

```
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Gly Gly Gly Gly Ser Gly Gly Gly Gly Ser Gly Gly Gly
    450                 455                 460

Gly Ser Gln Val Gln Leu Val Gln Ser Gly Gly Gly Leu Val Gln Pro
465                 470                 475                 480

Gly Gly Ser Leu Arg Leu Ser Cys Ala Ala Ser Gly Phe Thr Phe Asp
                485                 490                 495

Asp Tyr Ala Met His Trp Val Arg Gln Ala Pro Gly Lys Gly Leu Glu
            500                 505                 510

Trp Val Ala Gly Ile Ser Trp Asp Ser Gly Ser Thr Gly Tyr Ala Asp
        515                 520                 525

Ser Val Lys Gly Arg Phe Thr Ile Ser Arg Asp Asn Ala Lys Asn Ser
    530                 535                 540

Leu Tyr Leu Gln Met Asn Ser Leu Arg Ala Glu Asp Thr Ala Leu Tyr
545                 550                 555                 560

Tyr Cys Ala Arg Asp Leu Gly Ala Tyr Gln Trp Val Glu Gly Phe Asp
                565                 570                 575

Tyr Trp Gly Gln Gly Thr Leu Val Thr Val Ser Ser Ala Ser Thr Gly
            580                 585                 590

Gly Gly Gly Ser Gly Gly Gly Gly Ser Gly Gly Gly Gly Ser Gly Gly
        595                 600                 605

Gly Gly Ser Ser Tyr Glu Leu Thr Gln Asp Pro Ala Val Ser Val Ala
    610                 615                 620

Leu Gly Gln Thr Val Arg Ile Thr Cys Gln Gly Asp Ser Leu Arg Ser
625                 630                 635                 640
```

-continued

```
Tyr Tyr Ala Ser Trp Tyr Gln Gln Lys Pro Gly Gln Ala Pro Val Leu
                645                 650                 655

Val Ile Tyr Gly Lys Asn Asn Arg Pro Ser Gly Ile Pro Asp Arg Phe
            660                 665                 670

Ser Gly Ser Thr Ser Gly Asn Ser Ala Ser Leu Thr Ile Thr Gly Ala
        675                 680                 685

Gln Ala Glu Asp Glu Ala Asp Tyr Tyr Cys Asn Ser Arg Asp Ser Pro
    690                 695                 700

Gly Asn Gln Trp Val Phe Gly Gly Gly Thr Lys Val Thr Val Leu Gly
705                 710                 715                 720


<210> SEQ ID NO 74
<211> LENGTH: 214
<212> TYPE: PRT
<213> ORGANISM: Artificial Sequence
<220> FEATURE:
<223> OTHER INFORMATION: Light Chain of Istiratumab

<400> SEQUENCE: 74

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Lys Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Trp Thr Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 75
<211> LENGTH: 10
<212> TYPE: PRT
<213> ORGANISM: Artificial Sequence
<220> FEATURE:
<223> OTHER INFORMATION: HCDR1 of AVE1642 (Humanized form of murine
      antibody EM164)

<400> SEQUENCE: 75
```

-continued

```
Gly Tyr Thr Phe Thr Ser Tyr Trp Met His
1               5                   10


<210> SEQ ID NO 76
<211> LENGTH: 10
<212> TYPE: PRT
<213> ORGANISM: Artificial Sequence
<220> FEATURE:
<223> OTHER INFORMATION: HCDR2 of AVE1642 (Humanized form of murine
      antibody EM164)

<400> SEQUENCE: 76

Glu Ile Asn Pro Ser Asn Gly Arg Thr Asn
1               5                   10


<210> SEQ ID NO 77
<211> LENGTH: 17
<212> TYPE: PRT
<213> ORGANISM: Artificial Sequence
<220> FEATURE:
<223> OTHER INFORMATION: HCDR2 of AVE1642 (Humanized form of murine
      antibody EM164)

<400> SEQUENCE: 77

Glu Ile Asn Pro Ser Asn Gly Arg Thr Asn Tyr Asn Gln Lys Phe Gln
1               5                   10                  15

Gly


<210> SEQ ID NO 78
<211> LENGTH: 124
<212> TYPE: PRT
<213> ORGANISM: Artificial Sequence
<220> FEATURE:
<223> OTHER INFORMATION: VH2 Domain of AVE1642

<400> SEQUENCE: 78

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Gln Lys Phe
    50                  55                  60

Gln Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser Ser
        115                 120


<210> SEQ ID NO 79
<211> LENGTH: 123
<212> TYPE: PRT
<213> ORGANISM: Artificial Sequence
<220> FEATURE:
<223> OTHER INFORMATION: VH3 domain of AVE1642

<400> SEQUENCE: 79

Gln Val Gln Leu Val Gln Ser Gly Ala Glu Val Val Lys Pro Gly Ala
1               5                   10                  15
```

Ser Val Lys Leu Ser Cys Lys Ala Ser Gly Tyr Thr Phe Thr Ser Tyr
20 25 30

Trp Met His Trp Val Lys Gln Arg Pro Gly Gln Gly Leu Glu Trp Ile
35 40 45

Gly Glu Ile Asn Pro Ser Asn Gly Arg Thr Asn Tyr Asn Gln Lys Phe
50 55 60

Gln Gly Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Phe
85 90 95

Ala Arg Gly Arg Pro Asp Tyr Tyr Gly Ser Ser Lys Trp Tyr Phe Asp
100 105 110

Val Trp Gly Gln Gly Thr Thr Val Thr Val Ser
115 120

<210> SEQ ID NO 80
<211> LENGTH: 113
<212> TYPE: PRT
<213> ORGANISM: Artificial Sequence
<220> FEATURE:
<223> OTHER INFORMATION: VL2 domain of AVE1642

<400> SEQUENCE: 80

Asp Val Val Met Thr Gln Thr Pro Leu Ser Leu Pro Val Ser Leu Gly
1 5 10 15

Asp Pro Ala Ser Ile Ser Cys Arg Ser Ser Gln Ser Ile Val His Ser
20 25 30

Asn Val Asn Thr Tyr Leu Glu Trp Tyr Leu Gln Lys Pro Gly Gln Ser
35 40 45

Pro Arg Leu Leu Ile Tyr Lys Val Ser Asn Arg Phe Ser Gly Val Pro
50 55 60

Asp Arg Phe Ser Gly Ser Gly Ala Gly Thr Asp Phe Thr Leu Arg Ile
65 70 75 80

Ser Arg Val Glu Ala Glu Asp Leu Gly Ile Tyr Tyr Cys Phe Gln Gly
85 90 95

Ser His Val Pro Pro Thr Phe Gly Gly Gly Thr Lys Leu Glu Ile Lys
100 105 110

Arg

<210> SEQ ID NO 81
<211> LENGTH: 113
<212> TYPE: PRT
<213> ORGANISM: Artificial Sequence
<220> FEATURE:
<223> OTHER INFORMATION: VL3 domain of AVE1642

<400> SEQUENCE: 81

Asp Val Leu Met Thr Gln Thr Pro Leu Ser Leu Pro Val Ser Leu Gly
1 5 10 15

Asp Pro Ala Ser Ile Ser Cys Arg Ser Ser Gln Ser Ile Val His Ser
20 25 30

Asn Val Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ala Gly Thr Asp Phe Thr Leu Arg Ile
65 70 75 80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 82
<211> LENGTH: 113
<212> TYPE: PRT
<213> ORGANISM: Artificial Sequence
<220> FEATURE:
<223> OTHER INFORMATION: VL4 of AVE1642

<400> SEQUENCE: 82

Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 83
<211> LENGTH: 113
<212> TYPE: PRT
<213> ORGANISM: Artificial Sequence
<220> FEATURE:
<223> OTHER INFORMATION: VL5 domain of AVE1642

<400> SEQUENCE: 83

Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 84
<211> LENGTH: 5
<212> TYPE: PRT

<213> ORGANISM: Artificial Sequence
<220> FEATURE:
<223> OTHER INFORMATION: CDRH1 of Teprotumumab and Antibody 2

<400> SEQUENCE: 84

Ser Tyr Gly Met His
1 5

<210> SEQ ID NO 85
<211> LENGTH: 17
<212> TYPE: PRT
<213> ORGANISM: Artificial Sequence
<220> FEATURE:
<223> OTHER INFORMATION: CDRH2 of Teprotumumab

<400> SEQUENCE: 85

Ile Ile Trp Phe Asp Gly Ser Ser Thr Tyr Tyr Ala Asp Ser Val Arg
1 5 10 15

Gly

<210> SEQ ID NO 86
<211> LENGTH: 9
<212> TYPE: PRT
<213> ORGANISM: Artificial Sequence
<220> FEATURE:
<223> OTHER INFORMATION: CDRH3 of Teprotumumab and Antibody 2

<400> SEQUENCE: 86

Glu Leu Gly Arg Arg Tyr Phe Asp Leu
1 5

<210> SEQ ID NO 87
<211> LENGTH: 11
<212> TYPE: PRT
<213> ORGANISM: Artificial Sequence
<220> FEATURE:
<223> OTHER INFORMATION: CDRL1 of Teprotumumab and Antibody 2

<400> SEQUENCE: 87

Arg Ala Ser Gln Ser Val Ser Ser Tyr Leu Ala
1 5 10

<210> SEQ ID NO 88
<211> LENGTH: 7
<212> TYPE: PRT
<213> ORGANISM: Artificial Sequence
<220> FEATURE:
<223> OTHER INFORMATION: CDRL2 of Teprotumumab

<400> SEQUENCE: 88

Asp Ala Ser Lys Arg Ala Thr
1 5

<210> SEQ ID NO 89
<211> LENGTH: 10
<212> TYPE: PRT
<213> ORGANISM: Artificial Sequence
<220> FEATURE:
<223> OTHER INFORMATION: CDRL3 of Teprotumumab and Antibody 2

<400> SEQUENCE: 89

Gln Gln Arg Ser Lys Trp Pro Pro Trp Thr
1 5 10

<210> SEQ ID NO 90
<211> LENGTH: 118

<212> TYPE: PRT
<213> ORGANISM: Artificial Sequence
<220> FEATURE:
<223> OTHER INFORMATION: VH of Teprotumumab

<400> SEQUENCE: 90

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
        115
```

<210> SEQ ID NO 91
<211> LENGTH: 108
<212> TYPE: PRT
<213> ORGANISM: Artificial Sequence
<220> FEATURE:
<223> OTHER INFORMATION: VL of Teprotumumab

<400> SEQUENCE: 91

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
            100                 105
```

<210> SEQ ID NO 92
<211> LENGTH: 17
<212> TYPE: PRT
<213> ORGANISM: Artificial Sequence
<220> FEATURE:
<223> OTHER INFORMATION: CDRH2 of Antibody 2

<400> SEQUENCE: 92

```
Ile Ile Trp Phe Asp Gly Ser Ser Lys Tyr Tyr Gly Asp Ser Val Lys
1               5                   10                  15

Gly
```

<210> SEQ ID NO 93

-continued

<211> LENGTH: 7
<212> TYPE: PRT
<213> ORGANISM: Artificial Sequence
<220> FEATURE:
<223> OTHER INFORMATION: CDRL2 of Antibody 2

<400> SEQUENCE: 93

Asp Ala Ser Asn Arg Ala Thr
1               5

<210> SEQ ID NO 94
<211> LENGTH: 118
<212> TYPE: PRT
<213> ORGANISM: Artificial Sequence
<220> FEATURE:
<223> OTHER INFORMATION: VH of Antibody 2

<400> SEQUENCE: 94

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

Ala Ile Ile Trp Phe Asp Gly Ser Ser Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Glu Leu Gly Arg Arg Tyr Phe Asp Leu Trp Gly Arg Gly Thr
            100                 105                 110

Leu Val Thr Val Ser Ser
        115

<210> SEQ ID NO 95
<211> LENGTH: 108
<212> TYPE: PRT
<213> ORGANISM: Artificial Sequence
<220> FEATURE:
<223> OTHER INFORMATION: VL of Antibody 2

<400> SEQUENCE: 95

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ile Lys
            100                 105